US012584145B2

(12) United States Patent (10) Patent No.: US 12,584,145 B2

Curiel et al. (45) Date of Patent: Mar. 24, 2026

(54) CONJUGATE SYSTEMS AND METHODS OF USE THEREOF

(71) Applicants:David Curiel, St. Louis, MO (US); Zhi Hong Lu, St. Louis, MO (US)

(72) Inventors: David Curiel, St. Louis, MO (US); Zhi Hong Lu, St. Louis, MO (US)

(73) Assignee: Washington University, St. Louis, MO (US)

( * ) Notice: Subject to any disclaimer, the term of this patent is extended or adjusted under 35 U.S.C. 154(b) by 524 days.

(21) Appl. No.: 18/301,228

(22) Filed: Apr. 15, 2023

(65) Prior Publication Data

US 2023/0332181 A1　　Oct. 19, 2023

Related U.S. Application Data

(60) Provisional application No. 63/331,279, filed on Apr. 15, 2022.

(51) Int. Cl.
| | |
|---|---|
| *C12N 15/86* | (2006.01) |
| *A61P 35/00* | (2006.01) |
| *C07K 14/47* | (2006.01) |
| *C12N 9/22* | (2006.01) |

(52) U.S. Cl.
CPC .............. *C12N 15/86* (2013.01); *A61P 35/00* (2018.01); *C07K 14/4748* (2013.01); *C12N 9/22* (2013.01); *C12N 2710/10343* (2013.01)

(58) Field of Classification Search
CPC .................................................... C12N 15/86
See application file for complete search history.

(56) References Cited

U.S. PATENT DOCUMENTS

| | | |
|---|---|---|
| 2018/0163188 A1 | 6/2018 | Xie et al. |
| 2020/0140492 A1 | 5/2020 | Sabin et al. |

| | | | |
|---|---|---|---|
| 2020/0407708 A1 | 12/2020 | McKnight | |
| 2020/0407751 A1* | 12/2020 | Byrne ................... | C12N 15/11 |
| 2022/0372514 A1* | 11/2022 | Dicks ................ | A61K 39/0011 |

FOREIGN PATENT DOCUMENTS

| | | |
|---|---|---|
| WO | 2019169144 A1 | 9/2019 |
| WO | 2021084282 A1 | 5/2021 |

OTHER PUBLICATIONS

Chevillard et al. Elicitation of potent SARS-CoV-2 neutralizing antibody responses through immunization with a versatile adenovirus-inspired multimerization platform, Mol Ther, May 2022, pp. 1913-1925, vol. 30, No. 5.

Kasaraneni et al. Retargeting Lentiviruses via SpyCatcher-SpyTag Chemistry for Gene Delivery into Specific Cell Types, mBio, 2017, pp. 10-1128, vol. 8, No. 6.

Tan et al. A COVID-19 vaccine candidate using SpyCatcher multimerization of the SARS-COV-2 spike protein receptor-binding domain induces potent neutralising antibody responses, Nat Commun, 2021, vol. 12, article No. 542.

Hartzell et al. Modular Hepatitis B Virus-Like Particle Platform for Biosensing and Drug Delivery, ACS Nano, 2020, pp. 12642-12651, vol. 14, No. 10.

* cited by examiner

*Primary Examiner* — Mark L Shibuya

(57) ABSTRACT

Among the various aspects of the present disclosure is the provision of conjugate systems and methods of use thereof. In an aspect, the conjugate system includes an adenovirus comprising an exterior surface, and at least one polypeptide comprising a first domain and a second domain, and wherein the exterior surface comprises a peptide tag capable of binding to a binding partner.

25 Claims, 35 Drawing Sheets

(31 of 35 Drawing Sheet(s) Filed in Color)

Specification includes a Sequence Listing.

SpTMBP-SpC conjugate

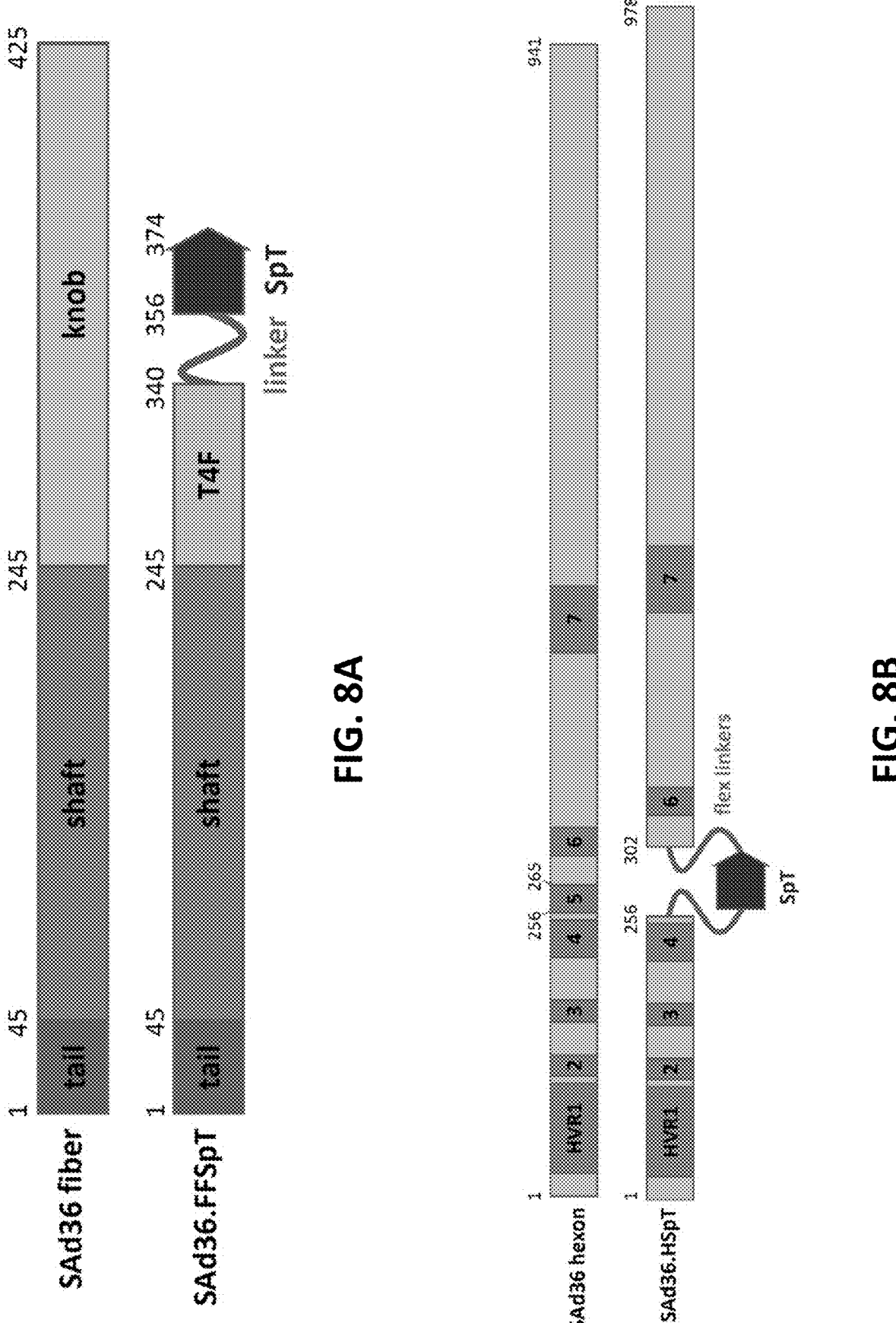

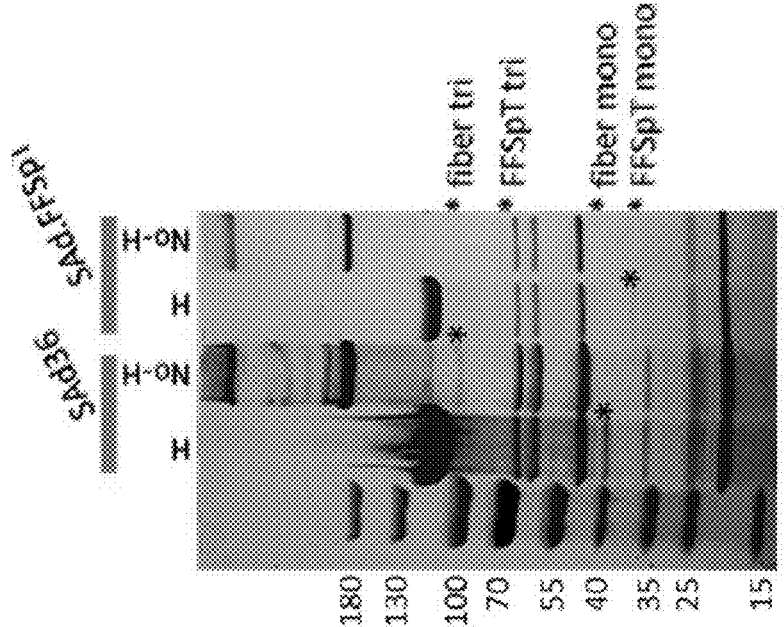
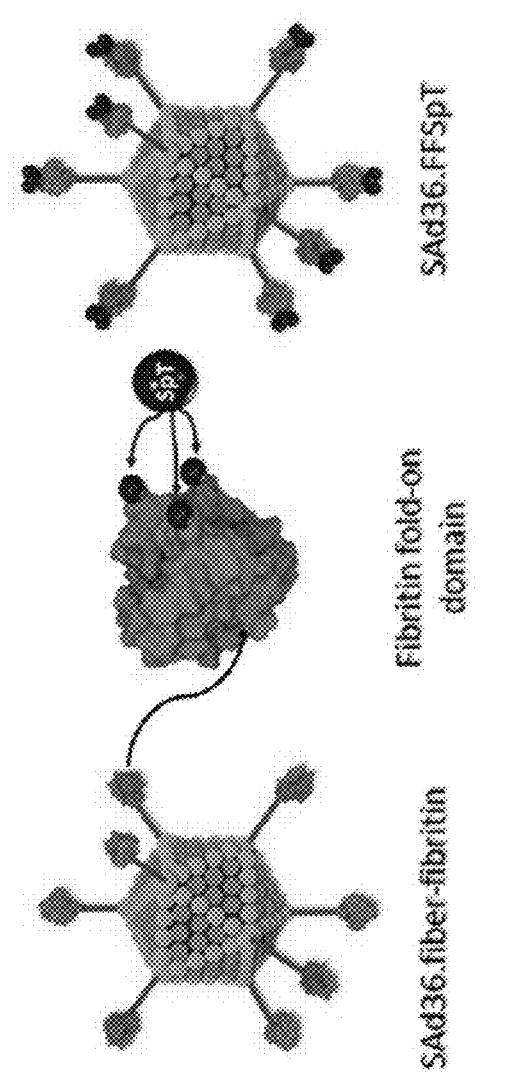
FIG. 9A

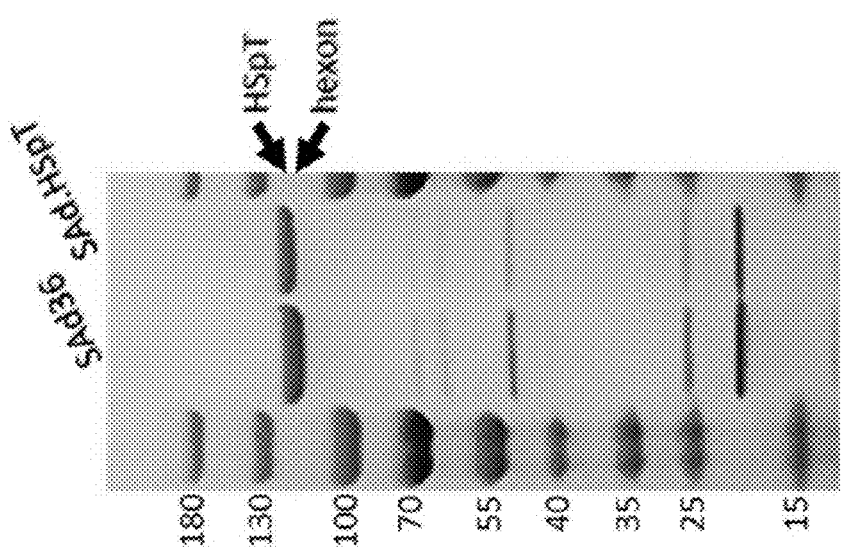
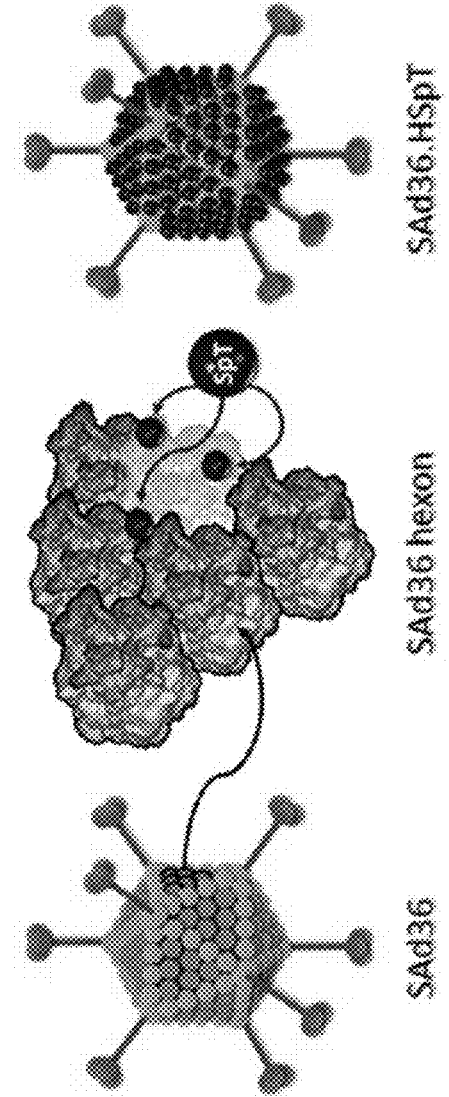
FIG. 9B

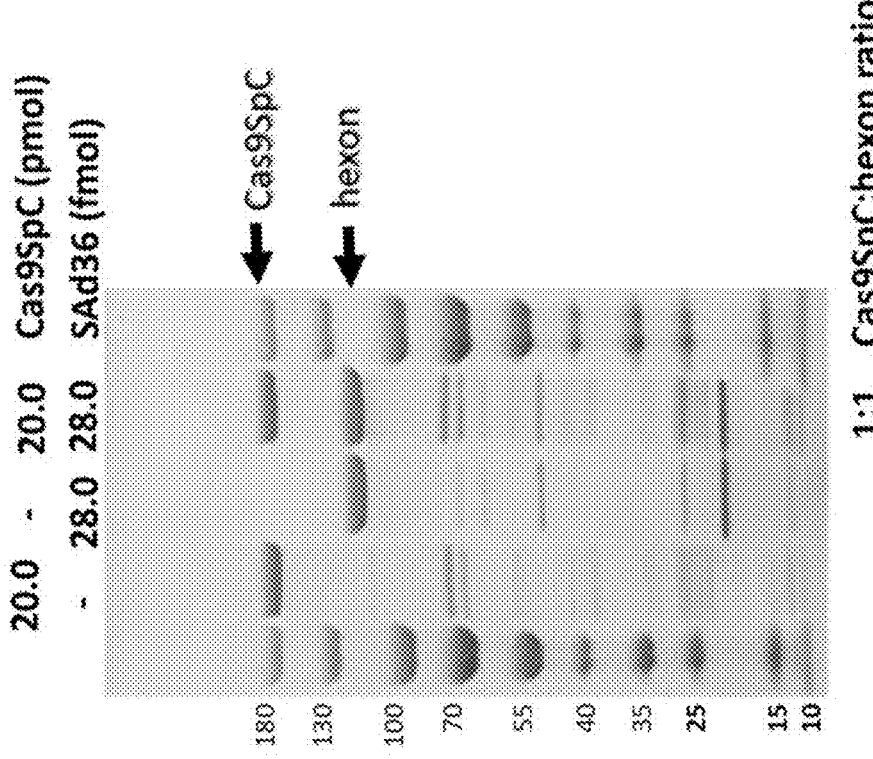
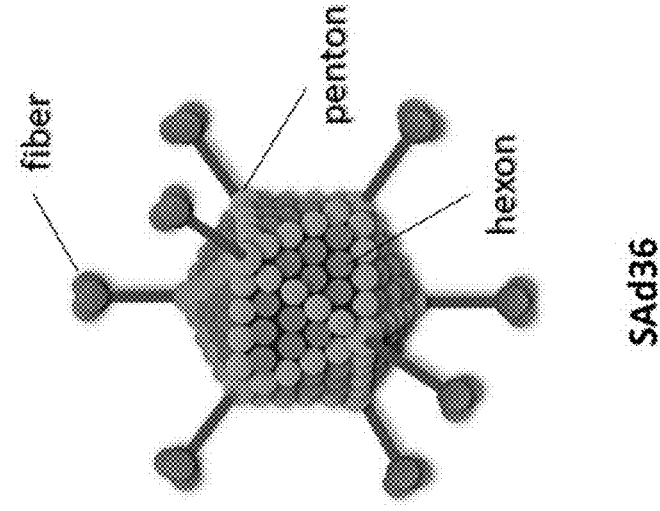
FIG. 10

CONJUGATE SYSTEMS AND METHODS OF USE THEREOF

CROSS-REFERENCE TO RELATED APPLICATIONS

This application claims priority from U.S. Provisional Application Ser. No. 63/331,279 filed on 15 Apr. 2022, which is incorporated herein by reference in its entirety.

STATEMENT REGARDING FEDERALLY SPONSORED RESEARCH OR DEVELOPMENT

This invention was made with government support under TR002851 awarded by the National Institutes of Health. The government has certain rights in the invention.

MATERIAL INCORPORATED-BY-REFERENCE

The Sequence Listing, which is a part of the present disclosure, includes a computer-readable form comprising nucleotide and/or amino acid sequences of the present invention (file name 020048-US-NP_Sequence_Listing.xml created on 10 Apr. 2023; 9,694 bytes). The subject matter of the Sequence Listing is incorporated herein by reference in its entirety.

FIELD

The present disclosure generally relates to conjugate systems comprising an adenovirus.

SUMMARY

Among the various aspects of the present disclosure is the provision of conjugate systems and methods of use thereof.

One aspect of the present disclosure provides for a conjugate system comprising: (i) an adenovirus comprising an exterior surface, wherein the exterior surface comprises a hexon protein surface and a fiber knob surface; and (ii) at least one polypeptide comprising a first domain and a second domain, wherein the first domain comprises a binding partner and the second domain comprises a Cas protein; and wherein the hexon protein surface and/or the fiber knob surface comprises a peptide tag capable of binding to the binding partner.

In some embodiments, the peptide tag is a SpyTag and the binding partner is a SpyCatcher. In some embodiments, the at least one polypeptide further comprises at least one nuclear localization signal (NLS), affinity tag, or flexible peptide linker. In some embodiments, the binding partner and the peptide tag are covalently bound. In some embodiments, the adenovirus is a simian adenovirus or simian adenovirus species E serotype 36 (Sad36). In some embodiments, the fiber knob surface comprises a fibritin T4 fold-on domain. In some embodiments, the peptide tag is associated with a hypervariable region of the hexon protein surface. In some embodiments, the peptide tag is fused to a flexible linker. In some embodiments, the adenovirus comprises at least about 30 fiber knob surfaces comprising the peptide tag. In some embodiments, the adenovirus comprises at least about 300 hexon protein surfaces comprising the peptide tag. In some embodiments, the conjugate system further comprises a guide RNA (gRNA). In some embodiments, the at least one polypeptide or the peptide tag further comprises a protease-cleavable linker, a protease-cleavable linker comprises an adenovirus L3 protease (AVP) preferential cleavage site, or a biodegradable linker. In some embodiments, the adenovirus does not comprise viral DNA. In some embodiments, the conjugate system further comprises targeting peptides or targeting adapters.

Another aspect of the present disclosure provides for a method of genetically engineering a cell, the method comprising delivering the conjugate system to the cell.

Yet another aspect of the present disclosure provides for a conjugate system comprising: (i) an adenovirus comprising an exterior surface comprising a hexon protein surface and a protein IX surfacer; and (ii) at least one polypeptide comprising a first domain and a second domain, wherein the first domain comprises a binding partner and the second domain comprises an mRNA-binding domain; and wherein the hexon protein surface and/or the protein IX surface comprises a peptide tag capable of binding to the binding partner.

In some embodiments, the peptide tag is a SpyTag and the binding partner is a SpyCatcher; the peptide tag is a DogTag and the binding partner is a DogCatcher; or the peptide tag is a SnoopTag and the binding partner is a SnoopCatcher. In some embodiments, the conjugate system further comprises an mRNA, a linear mRNA, a circular mRNA, or a self-replicating mRNA. In some embodiments, the mRNA-binding domain comprises polylysine, protamine, or RALA.

In some embodiments, the mRNA encodes a cancer neoantigen, such that the present disclosure further provides for a method of treating cancer in a subject in need thereof, the method comprising administering to the subject the conjugate system.

Yet another aspect of the present disclosure provides for a method of providing gene therapy to a subject in need thereof, the method comprising administering to the subject the conjugate system.

Other objects and features will be in part apparent and in part pointed out hereinafter.

DESCRIPTION OF THE DRAWINGS

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

FIG. 3 contains images showing Cas9 and Cas9SpC with the indicated amounts were resolved on an SDS-PAGE gel followed by Coomassie blue staining (left) or by immunoblotting with anti-SpCas9 and anti-6× His antibodies (middle and right).

FIG. 5 contains a schematic diagram of the Rosa26:Ai9-SauSpyCas9-tdTomato (mAi9) locus without or with gene editing. Three SV40 polyadenylation signals (STOP) function as a potent transcription inhibition element to the downstream tdTomato gene. Endonuclease cleavage at both upstream and downstream sites by Cas9/lox gRNA can lead to a subset of alleles with deletion of the STOP cassette and activation of the tdTomato gene expression. The locations of duplicate lox gRNA sites and PCR genotyping primers are illustrated.

FIG. 6A-FIG. 6B contain representative bright-field and tdTomato fluorescence microscopy images of mAi9 cells on day 4 following lipofectamine CRISPRMAX transfection with lox gRNA and Cas9 or with lox gRNA and Cas9SpC. The numbers above micrographs indicate the amount of reagents in pmol added to $1 \times 10^5$ mAi9 cells in 500 µl of culture media in 24-well format.

FIG. 7A and FIG. 7B contain scatter plots with a bar graph showing the percentage of tdTomato-positive cells by fluorescence microscopy analysis of mAi9 cells on day 4 following lipofectamine CRISPRMAX transfection with Cas9/lox gRNA or with Cas9SpC/lox gRNA. The numbers below the graphs indicate the amount of reagents in picomoles added to $1 \times 10^5$ mAi9 cells in 500 µL of culture media in a 24-well format. FIG. 7C contains a flow cytometry analysis of the percentage of tdTomato-positive mAi9 cells on day 4 following transfection with 7.5 pmol of Cas9/lox gRNA or with 7.5 pmol of Cas9SpC/lox gRNA to $5 \times 10^4$ mAi9 cells in 500 µL of culture media in a 24-well format. Cells a receiving mock treatment with phosphate-buffered saline were used to set the gate for detection of tdTomato-positive cells. FIG. 7D contains a scatter plot with a bar graph showing flow cytometry analysis of the percentage of tdTomato-positive cells on day 4 following transfection with Cas9/lox gRNA or with Cas9SpC/lox gRNA to mAi9 cells seeded at varying seeding cell densities in a 24-well format. Two replicate experiments were performed for FIG. 7A-7D. Data are represented as mean±standard deviation from six wells of two replicate experiments for parts FIG. 7A and FIG. 7B and as three wells of one representative experiment for FIG. 7C-7D.

FIG. 8A-FIG. 8B is an exemplary embodiment showing placement of SpT on SAd36 surface capsid proteins in accordance with the present disclosure. FIG. 8A contains diagrams comparing wild type SAd36 fiber and the SpT-incorporated fiber. The knob domain is removed and replaced with the trimerization fold-on region from the T4 phage fibritin protein (T4F) fused to the SpT peptide via a flexible linker (4×GGGS). FIG. 8B contains diagrams comparing wild type SAd36 hexon and the SpT hexon. A hypervariable region (HVR) 5 of hexon likely adopting an outward flexible loop morphology is replaced with SpT flanked by two 15-residue flexible linkers.

FIG. 9A-FIG. 9B is an exemplary embodiment showing generation of SAd36 vectors with SpT incorporated into the fiber and hexon in accordance with the present disclosure. FIG. 9A is a schema illustrating the SAd36 vector with the fiber knob domain replaced by the bacteriophage T4 fibritin fold-on domain which allows the outward display of SpT on the virus surface. The fiber-T4 fibritin-SpT (FFSpT) trimer is proportionally enlarged compared with the body of the virion for a clear presentation of the location of SpT. $2.5 \times 10^{10}$ viral particles of SAd36 and SAd36.FFSpT were denatured in SDS sample buffer with or without boiling (H or No—H) for 8 min. Proteins were resolved by 4-15% gradient SDS-PAGE followed by Coomassie blue staining. The presence of FFSpT trimer (FFSpT tri) in the SAd36.FFSpT virus was detected in the sample treated without heating. FIG. 9B is a schema illustrating the SAd36 vector with hexon hypervariable region 5 replaced by SpT. SAd36 and SAd36.HSpT viral particles were analyzed by SDS-PAGE and Coomassie blue staining with heating as described in FIG. 9A.

FIG. 10 contains an image showing lack of non-specific crosslinking of Cas9SpC to unmodified SAd36 viral proteins in accordance with the present disclosure. 20.0 pmol of Cas9SpC and 28.0 fmol of SAd36 viral particles were mixed (1:1 SpC:hexon monomer molar ratio) in phosphate-buffered saline and incubated at 37° C. for two hours. The reaction mixtures were boiled in SDS sample buffer and resolved by SDS-PAGE with Coomassie blue staining.

FIG. 14A is a scatter plot with a bar graph showing the percentage of tdTomato-positive cells by fluorescence microscopy analysis of mAi9 cells on day 4 following virus infection. For this, $2 \times 10^5$ modified Ai9 cells in 500 μL of culture media in a 24-well format were incubated with SAd36, SAd36.FFSpT, and SAd36.HSpT at a $1.6 \times 10^4$ viral particles per cell ratio without or with a 2-h preincubation of 7.5 pmol of Cas9SpC/lox gRNA. Two replicate experiments were performed, and data are represented as mean±standard deviation from six wells of the two experiments. FIG. 14B is an image showing genotyping PCR analysis of the ROSA26-tdTomato locus using DNA samples derived from cells in one of the experiments shown in FIG. 14A. The locations of the PCR primers (F and R) are illustrated in FIG. 14B top row, predicted nontruncated PCR band, bottom row, truncated PCR fragments.

FIG. 15 contains a schematic showing next-generation sequencing analysis of truncated Rosa26-tdTomato PCR fragment amplified with genomic DNA derived from cells infected with SAd36.FFSpT-Cas9SpC/lox gRNA, indicated by truncated row in FIG. 14B. DNA was isolated 4 days post-virus infection. The location of various deletion species (boxed dash lines) and corresponding number of times of detection are provided. The numbers in parenthesis report the frequency of detection of a particular deletion species from all sequencing reads.

FIG. 16 contains a schematic showing next-generation sequencing analysis of the truncated Rosa26-tdTomato PCR fragment amplified with genomic DNA derived from cells infected with SAd36.HSpT-Cas9SpC/lox gRNA, indicated by the truncated row in FIG. 14B. The location of various deletion species (boxed dash lines) and the corresponding number of times of detection are provided. The numbers in parentheses report the frequency of detection of a particular deletion species from all sequencing reads.

FIG. 17 contains a schematic showing ICE analysis of non-truncated Rosa26-tdTomato PCR fragment amplified using genomic DNA derived from cells infected with SAd36.FFSpT-Cas9SpC/lox gRNA. DNA was isolated 4 days post-virus infection, and the overall indel frequency and list of indel patterns and corresponding frequencies at both upstream and downstream lox gRNA sites are provided.

FIG. 18 contains a schematic showing ICE analysis of the nontruncated Rosa26-tdTomato PCR fragment amplified using genomic DNA derived from cells infected with SAd36.HSpT-Cas9SpC/lox gRNA. DNA was isolated 4 days post virus infection. The overall indel frequencies at both upstream and downstream lox gRNA sites are provided, and a detailed report of the assay is provided in FIG. 19.

FIG. 19 contains a schematic showing ICE analysis of non-truncated Rosa26-tdTomato PCR fragment amplified using genomic DNA derived from cells infected with SAd36.HSpT-Cas9SpC/lox gRNA. DNA was isolated 4 days post-virus infection, and the overall indel frequency and list of indel patterns and corresponding frequencies at both upstream and downstream lox gRNA sites are provided.

FIG. 21A is a scatter plot with a bar graph showing the percentage of tdTomato-positive cells by fluorescence microscopy analysis of mAi9 cells on day 4 following virus infection. Specifically, $2 \times 10^5$ modified Ai9 cells were incubated with varying amounts of SAd36, SAd36.FFSpT, and SAd36.HSpT in the presence of 7.5 pmol of Cas9SpC/lox gRNA. The viral particle versus cell ratios are provided at the bottom of the plot. FIG. 21B contains a flow cytometry analysis of the percentage of tdTomato-positive cells on day 4 following infection of $1.0 \times 10^5$ mAi9 cells with SAd36.FFSpT-Cas9SpC/lox gRNA or SAd36.HSpT-Cas9SpC/lox gRNA at a $1.6 \times 10^4$ VP/C ratio (left). Cells receiving mock treatment with phosphate-buffered saline were used to set the gate for detection of tdTomato-positive cells. FIG. 21B also contains a scatter plot with a bar graph showing flow cytometry analysis of the percentage of tdTomato-positive cells on day 4 following infection with SAd36.FFSpT-Cas9SpC/lox gRNA or SAd36.HSpT-Cas9SpC/lox gRNA at a $1.6 \times 10^4$ VP/C ratio to cells with three different seeding densities: $2.0 \times 10^5$, $1.5 \times 10^5$, and $1.0 \times 10^5$ per well in a 24-well format (right). FIG. 21C contains an ICE analysis of the CDK4 locus PCR fragment amplified using genomic DNA derived from A549 cells ($5.0 \times 10^4$/well) infected with SAd36.HSpT-Cas9SpC/CDK4 gRNA at a $2.0 \times 10^4$ VP/C ratio (left). Genomic DNA was purified on day 2 post virus infection. FIG. 21C also contains a scatter plot with a bar graph showing ICE analysis of the percentage of CDK4 alleles harboring Cas9SpC-mediated indels on day 2 following infection with SAd36.HSpT-Cas9SpC/CDK4 gRNA at a $1.0 \times 10^4$ or $2.0 \times 10^4$ VP/C ratio to cells with two different seeding densities of $1.0 \times 10^5$ or $0.5 \times 10^4$ per well in a 24-well format. Two replicate experiments were performed for parts FIG. 21A-FIG. 21C. Data are represented as mean±standard deviation from six wells of two replicate experiments for FIG. 21A and three wells of one representative experiment for FIG. 21B-FIG. 21C.

FIG. 22A contains an immunoblot analysis (left) of free Cas9SpC, Cas9SpC conjugated on SAd36.FFSpT, and the fate of the Cas9SpC-FFSpT conjugate in mAi9 cells following infection with SAd36.FFSpT-Cas9SpC/tdT gRNA at a 1.6×10⁴ VP/C ratio. FIG. 22A also contains an immunoblot analysis (right) of free Cas9SpC, Cas9SpC conjugated on SAd36. HSpT, and the fate of Cas9SpC-HSpT in mAi9 cells following infection with SAd36.HSpT-Cas9SpC/tdT gRNA at a 1.6×10⁴ VP/C ratio. The tdT gRNA sequence is 5'-ggccacgagttcgagatcga-3' (SEQ ID NO: 3) followed by a PAM sequence of 5'-ggg-3'. The tdT gRNA recognizes two sites in tdTomato gene as this gene itself is a genetic fusion of two copies of a dTomato gene. FIG. 22B contains an immunofluorescence microscopy analysis of subcellular localization of the Cas9 moiety in virus-infected mAi9 cells. Strikingly, robust GFP fluorescence signals without antibody staining were readily detectable in a small number of cells by 6 h post virus infection. Magnification, ×40. Red, Cas9 moiety; green, GFP; blue, DAPI. Right panel: DAPI staining revealed the nucleus of each cell, and subcellular localization of the Cas9 moiety versus the nucleus location in all assayed cells was scored. The bar graph illustrates the percentage of cells showing nuclear Cas9 detection, cytoplasm-only Cas9 staining, or no cellular Cas9 detection in individual virus/time groups. FIG. 22C contains images showing co-immunofluorescence staining of the Cas9 moiety and SAd36 hexon in cells at 6 h post virus infection detected colocalization of the two protein moieties. Cas9 and hexon were revealed in the Texas Red and Cy5 (far-red)-channels, respectively, and the hexon staining was pseudocolored in green. Magnifications, ×100. Red, Cas9; green, hexon; blue, DAPI.

FIG. 23A is a map of Rosa26-tdTomato locus with the locations of PCR primers, lox gRNA, and mAi9 gRNA2 illustrated. Fragments a, b, c, d, e1, e2, and f generated from endonuclease cleavage are indicated. FIG. 23B and FIG. 23C contain images showing 1231 bp Rosa26-tdTomato genomic DNA fragment was amplified by PCR, and gRNA-directed Cas9- and Cas9SpC-mediated cleavage assay was performed with lox gRNA (FIG. 23B) or with mAi9 gRNA2 (FIG. 23C). In lanes 4 and 5 of both FIG. 23B and FIG. 23C, the SpT viruses were provided with an excess of viral SpT to titrate free Cas9SpC into FFSpT- or HSpT-conjugated forms before the assay.

FIG. 25A is a schematic showing various combinations of specific and nonspecific complex components of the Ad-pL-mRNA construct were evaluated for the capacity to mediate mRNA gene transfer to CHO cells. The mRNA encoding the firefly luciferase gene was used as a reporter complexed with biotinylated adenovirus-polylysine [(B)-labelled Ad5PK4]. Ad5PK4 expresses GFP. The reporter gene expression in the cell lysates was determined 48 hours after infection by luciferase assay. FIG. 25B includes images showing evaluation of in vivo gene transfer mediated by AdPK4-STAPIys-mRNA complexes via intramuscular injection to mice. Immunohistochemical staining analysis was performed to evaluate in vivo gene transfer mediated by AdPK4-STAPIys-mRNA complexes via intramuscular injection in mice. In vivo gene delivery and gene expression were verified and analyzed by co-localization of the GFP and Luc signals in images taken from sections of muscle tissue. Indicated signals as follows: Green: GFP reporter gene in adenoviral vector (AdPK4.CMV.eGFP), Red: firefly luciferase gene expressed via mRNA delivery using anti-firefly luciferase antibody capture, and Yellow, representing co-localization of both signals. Blue (DAPI) indicates nuclear staining.

FIG. 27A is a bar graph showing Ad.hexon.SpyT/SpyC-protamine-mRNA complex mediates mRNA delivery in vitro. The contribution of each component to effective mRNA delivery is examined by setting the groups, Col 1: wild type; Col 2: mRNA=0.5 μg, protamine/mRNA=8:1; Col 3: Ad MOI=8,000, mRNA=0.5 μg; Col 4: Ad MOI=8,000, mRNA=0.5 μg, protamine/mRNA=8:1; Col 5: Ad.SpT MOI=8,000, mRNA=0.5 μg, SpyC-protamine/mRNA=8:1. FIG. 27B is a bar graph showing optimization of mRNA delivery efficiency of Ad.hexon.SpyT/SpyC-protamine-mRNA complex by varying components dose. mRNA encodes mCherry fluorescent protein gene and the percentage of mCherry-positive cells is measured by flow cytometry.

DETAILED DESCRIPTION

Figure 1:
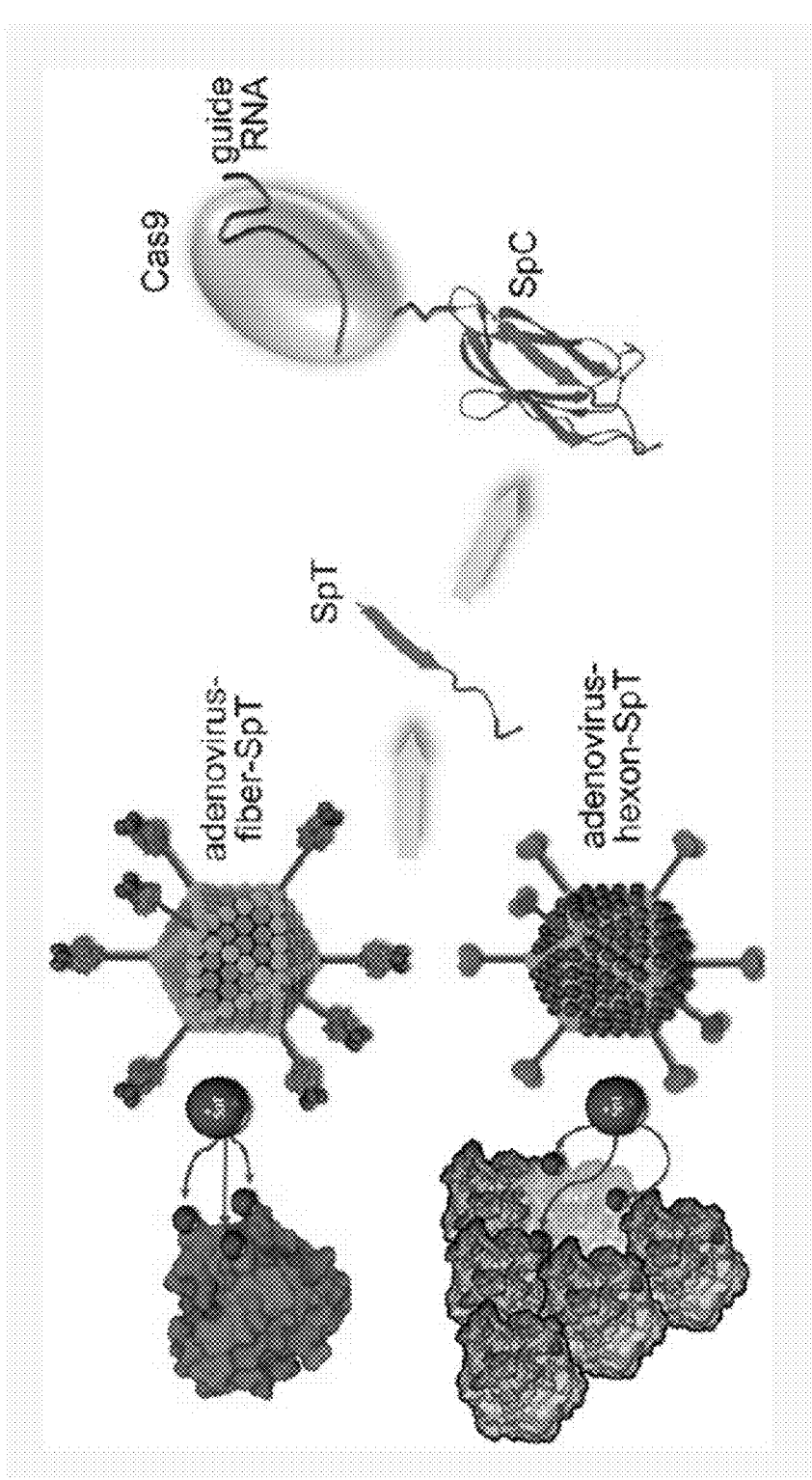
FIG. 1 is a schematic showing the repurposing of a simian adenoviral vector for DNA delivery in accordance with the present disclosure.

The present disclosure is based, at least in part, on the discovery that adenoviral vectors (Ad) can be employed to achieve cellular delivery of Cas9 protein to achieve gene editing. Modification of Ad capsid protein provides the functional basis for conjugating Cas9 protein to Ad surface. As shown herein, the process provides a delivery method to achieve efficient gene editing. In addition, Cas9 expression as a protein limits duration of gene editing and thus minimizes off-target effects.

The present disclosure provides for methods and compositions for Piggyback gene editing. The plug-and-play adenoviral platform can piggyback transport Cas9/gRNA complex on the viral capsid surface into the nucleus of target cells, leading to robust genome editing.

Cas-mediated gene editing strategies rely on introducing DNA sequences encoding an editor and guide g(RNA) to the nucleus of target cells via viral or non-viral methods. There are a number of complications that can occur using these methods including: insertional mutagenesis, undesired persistent Cas expression, and off-targeting editing. Emerging mRNA delivery circumvents these concerns but may trigger innate immunogenicity against cells taking up exogenous mRNA, and mRNA is susceptible to enzymatic degradation in blood and periphery.

A protein-based formulation offers one-time hit-and-run editing and has less tendency to induce an immune response thereby inferring improved safety over nucleic acid approaches. To date, gene editor ribonucleoprotein (RNP) enzyme complexes have been delivered by non-viral methods.

Herein, a gene therapy viral vector, simian adenovirus, is repurposed for DNA delivery to intracellularly deliver RNPs. The adenovirus can efficiently deliver viral DNA and its major capsid proteins into the cytoplasm of host cells. Using this strategy, preassembled Cas RNP complex was complexed to the surface of adenovirus (piggyback) and highly efficient gene editing was demonstrated in cells infected with the virus carrying Cas9/gRNA on its capsid proteins.

The system described herein is unique in that an adenoviral capsid conjugate approach is utilized to deliver an intracellularly-acting molecule, the cas9/gRNA RNP complex, the efficiency was comparable to that of a commercial CRISPR/Cas transfection reagent, and an off-the-shelf engineered virus and a Cas9/gRNA complex exploiting Spy-Tag003/Spycatcher003 coupling chemistry were utilized.

Additional advantages of the system described herein are i) adenovirus is the most efficient gene delivery system in a broad range of cell and tissue types; (ii) adenoviruses are widely used in clinical trials for gene delivery; (iii) the efficacy of this system is comparable to commercially available systems; (iv) this technology overcomes several limitations common to non-viral delivery methods: triggering innate immunity, degradation, insertional mutagenesis, and others; and (v) Ad-based delivery is expected to become increasingly popular.

Further, the system may potentially be used commercially for research purposes or to develop therapies.

Viral Capsid Conjugate Systems

The present disclosure provides for viral capsid conjugate systems and the synthesis and use thereof. As described herein, the conjugate systems may be used to deliver intracellularly acting macromolecules, such as a protein and/or a nucleic acid, via an adenoviral "piggyback" delivery route.

In one embodiment, the conjugate system comprises an engineered adenovirus conjugated to a Cas9 protein. Such a conjugate system may be administered to a cell, for example, in the presence of a guide RNA (gRNA), to form a Cas9/gRNA ribonucleoprotein (RNP) complex and deliver gene-editing functions to the cell.

In another embodiment, the conjugate system comprises an engineered adenovirus conjugated to a polypeptide comprising an mRNA-binding domain. Such a conjugate system may be administered to a subject, for example, in the presence of an mRNA encoding a cancer neoantigen to elicit neoantigen-specific T cell responses in the subject.

In some embodiments, the conjugate system comprises a "releasable function", whereby the intracellularly acting molecule may be released from the conjugate system within, for example, the cytoplasm or nucleus of a cell. For example, the conjugate system may comprise a protease-cleavable linker or a biodegradable linker, such as an adenovirus L3 protease (AVP) preferential cleavage site.

In some embodiments, the conjugate system comprises targeting peptides or adapters to target the conjugate system to specific tissues or cell types. Such targeting peptides or adapters, for example, may be genetically incorporated into a capsid protein of the adenovirus.

Adenovirus

As described herein, the conjugate systems of the present disclosure comprise an adenovirus. Adenoviruses as they naturally occur are characterized as non-enveloped viruses having an icosahedral protein capsid and an evolved infection pathway that efficiently delivers viral DNA and major capsid proteins to the cytoplasm of host cells. This viral infection pathway may be used as a "piggyback" route, wherein the adenovirus is engineered or modified to deliver, for example, a macromolecule such as Cas9 or mRNA to a cell or subject.

As described herein, the adenovirus is engineered such that a peptide tag capable of binding to a binding partner is genetically incorporated into an exterior surface of the adenovirus. The peptide tag may be incorporated into any exterior surface of the adenovirus, provided that the peptide tag is displayed on the surface in a manner that allows for binding of the peptide tag to the binding partner. For example, the exterior surface may be a hexon protein surface, a fiber knob surface, or a protein IX surface. As another example, the exterior surface may be a penton base surface, a protein IIIa surface, a protein VI surface, or a protein VIII surface. Preferably, the peptide tag is incorporated into an exterior surface of the adenovirus such that negative impacts on infectivity are minimized.

In some embodiments, incorporation of the peptide tag into an exterior surface of the adenovirus may replace, remove, or render nonfunctional a domain or region that is endogenous to the adenovirus. For example, incorporation of the peptide tag into a fiber knob surface may replace an inward C-terminus endogenous to the fiber knob surface. As another example, incorporation of the peptide tag into a hexon protein surface may replace an outward, 9-residue hypervariable region 5 loop endogenous to the adenovirus.

In some embodiments, the adenovirus of the present disclosure does not comprise viral DNA (e.g., an empty capsid or adenoviral-like particle). Formation of empty capsids precedes genome packaging into the empty capsids to form mature full virons; the empty capsids are a lower density and thus readily detectable and separable from capsids containing viral DNA during routine virus purification procedures.

There are a number of adenovirus species and/or variants known in the art that may be engineered for use in the conjugate systems of the present disclosure. In a preferred embodiment, the adenovirus is a simian (chimpanzee) adenovirus. Simian adenoviruses do not typically elicit pre-existing immunity in human populations, and thus may be particularly advantageous for vaccine or therapeutic applications involving administration to a human subject or cell. For example, the adenovirus may be a simian adenovirus species E serotype 36 (SAd36), which has been shown to have a favorable safety profile in humans.

Peptide Tags

As described herein, the conjugate systems of the present disclosure comprise a peptide tag, wherein the peptide tag is comprised in an exterior surface of an adenovirus as discussed above. The peptide tag may be any polypeptide or fragment thereof capable of binding to a binding partner. For example, the peptide tag may be capable of forming a covalent bond with the binding partner, preferably under physiological conditions. Examples of suitable peptide tags include SpyTag, SnoopTag, DogTag, or any variant thereof. In some embodiments, the peptide tag is flanked by at least one flexible linker.

Binding Partners

As described herein, the conjugate systems of the present disclosure comprise a binding partner. The binding partner may be any polypeptide or fragment thereof capable of binding to the peptide tag. For example, the binding partner may be capable of forming a covalent bond with the peptide tag, preferably under physiological conditions. Examples of suitable binding partners include SpyCatcher, Snoop-Catcher, DogCatcher or any variant thereof.

In some embodiments, the binding partner is comprised in a polypeptide comprising both the binding partner and a Cas protein (e.g., a fusion polypeptide). The Cas protein may be any Cas protein or variant thereof known in the art, the selection of which may depend on the desired application or use of the conjugate system. For example, the Cas protein may be Cas9, Cas12a, or Cas3.

In some embodiments, the binding partner is comprised in a polypeptide comprising both the binding partner and an mRNA binding protein. For example, the mRNA binding protein may be polylysine, protamine, or RALA.

The polypeptide may further comprise additional elements to facilitate desired localization, purification, or other characteristics of the polypeptide and/or conjugate system. For example, the polypeptide may comprise at least one nuclear localization signature (NLS), an affinity tag (such as a His tag), or a flexible peptide linker.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The term "transfection," as used herein, refers to the process of introducing nucleic acids into cells by non-viral methods. The term "transduction," as used herein, refers to the process whereby foreign DNA is introduced into another cell via a viral vector.

The terms "heterologous DNA sequence", "exogenous DNA segment", or "heterologous nucleic acid", "transgene", "exogenous polynucleotide" as used herein, each refers to a sequence that originates from a source foreign (e.g., non-native) to the particular host cell or, if from the same source, is modified from its original form. Thus, a heterologous gene in a host cell includes a gene that is endogenous to the particular host cell but has been modified through, for example, the use of DNA shuffling or cloning. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Sequences described herein can also be the reverse, the complement, or the reverse complement of the nucleotide sequences described herein. The RNA goes in the reverse direction compared to the DNA, but its base pairs still match (e.g., G to C). The reverse complementary RNA for a positive strand DNA sequence will be identical to the corresponding negative strand DNA sequence. Reverse complement converts a DNA sequence into its reverse, complement, or reverse-complement counterpart.

| Base | Name | Bases Represented | Complementary Base |
|------|------|-------------------|---------------------|
| A | Adenine | A | T |
| T | Thymidine | T | A |
| U | Uridine (RNA only) | U | A |
| G | Guanidine | G | C |
| C | Cytidine | C | G |
| Y | pYrimidine | C T | R |
| R | puRine | A G | Y |
| S | Strong (3Hbonds) | G C | S* |
| W | Weak (2Hbonds) | A T | W* |
| K | Keto | T/U G | M |
| M | aMino | A C | K |
| B | not A | C G T | V |
| D | not C | A G T | H |
| H | not G | A C T | D |
| V | not T/U | A C G | B |
| N | Unknown | A C G T | N |

Complementarity is a property shared between two nucleic acid sequences (e.g., RNA, DNA), such that when they are aligned antiparallel to each other, the nucleotide bases at each position will be complementary. Two bases are complementary if they form Watson-Crick base pairs.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

An "expression vector", otherwise known as an "expression construct", is generally a plasmid or virus designed for gene expression in cells. The vector is used to introduce a specific gene into a target cell, and can commandeer the cell's mechanism for protein synthesis to produce the protein encoded by the gene. Expression vectors are the basic tools in biotechnology for the production of proteins. The vector is engineered to contain regulatory sequences that act as enhancer and/or promoter regions and lead to efficient transcription of the gene carried on the expression vector. The goal of a well-designed expression vector is the efficient production of protein, and this may be achieved by the production of significant amount of stable messenger RNA, which can then be translated into protein. The expression of a protein may be tightly controlled, and the protein is only produced in significant quantity when necessary through the use of an inducer, in some systems however the protein may be expressed constitutively. As described herein, *Escherichia coli* is used as the host for protein production, but other cell types may also be used.

In molecular biology, an "inducer" is a molecule that regulates gene expression. An inducer can function in two ways, such as:

(i) By disabling repressors. The gene is expressed because an inducer binds to the repressor. The binding of the inducer to the repressor prevents the repressor from binding to the operator. RNA polymerase can then begin to transcribe operon genes. An operon is a cluster of genes that are transcribed together to give a single messenger RNA (mRNA) molecule, which therefore encodes multiple proteins.

(ii) By binding to activators. Activators generally bind poorly to activator DNA sequences unless an inducer is present. An activator binds to an inducer and the complex binds to the activation sequence and activates target gene. Removing the inducer stops transcription. Because a small inducer molecule is required, the increased expression of the target gene is called induction.

Repressor proteins bind to the DNA strand and prevent RNA polymerase from being able to attach to the DNA and synthesize mRNA. Inducers bind to repressors, causing them to change shape and preventing them from binding to DNA. Therefore, they allow transcription, and thus gene expression, to take place.

For a gene to be expressed, its DNA sequence (or polynucleotide sequence) must be copied (in a process known as transcription) to make a smaller, mobile molecule called messenger RNA (mRNA), which carries the instructions for making a protein to the site where the protein is manufactured (in a process known as translation). Many different types of proteins can affect the level of gene expression by promoting or preventing transcription. In prokaryotes (such as bacteria), these proteins often act on a portion of DNA known as the operator at the beginning of the gene. The promoter is where RNA polymerase, the enzyme that copies the genetic sequence and synthesizes the mRNA, attaches to the DNA strand.

Some genes are modulated by activators, which have the opposite effect on gene expression as repressors. Inducers can also bind to activator proteins, allowing them to bind to the operator DNA where they promote RNA transcription. Ligands that bind to deactivate activator proteins are not, in the technical sense, classified as inducers, since they have the effect of preventing transcription.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "ribosome binding site", or "ribosomal binding site (RBS)", refers to a sequence of nucleotides upstream of the start codon of an mRNA transcript that is responsible for the recruitment of a ribosome during the initiation of translation. Generally, RBS refers to bacterial sequences, although internal ribosome entry sites (IRES) have been described in mRNAs of eukaryotic cells or viruses that infect eukaryotes. Ribosome recruitment in eukaryotes is generally mediated by the 5' cap present on eukaryotic mRNAs.

A ribosomal skipping sequence (e.g., 2A sequence such as furin-GSG-T2A) can be used in a construct to prevent covalently linking translated amino acid sequences.

A "transcribable nucleic acid molecule" as used herein refers to any nucleic acid molecule capable of being transcribed into an RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A construct of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal, or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using self-replicating primers, paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above-required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123;

Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2, or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A. For example, the percent identity can be at least 80% or about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

Substitution refers to the replacement of one amino acid with another amino acid in a protein or the replacement of one nucleotide with another in DNA or RNA. Insertion refers to the insertion of one or more amino acids in a protein or the insertion of one or more nucleotides with another in DNA or RNA. Deletion refers to the deletion of one or more amino acids in a protein or the deletion of one or more nucleotides with another in DNA or RNA. Generally, substitutions, insertions, or deletions can be made at any position so long as the required activity is retained.

"Point mutation" refers to when a single base pair is altered. A point mutation or substitution is a genetic mutation where a single nucleotide base is changed, inserted, or deleted from a DNA or RNA sequence of an organism's genome. Point mutations have a variety of effects on the downstream protein product-consequences that are moderately predictable based upon the specifics of the mutation. These consequences can range from no effect (e.g., synonymous mutations) to deleterious effects (e.g., frameshift mutations), with regard to protein production, composition, and function. Point mutations can have one of three effects. First, the base substitution can be a silent mutation where the altered codon corresponds to the same amino acid. Second, the base substitution can be a missense mutation where the altered codon corresponds to a different amino acid. Or third, the base substitution can be a nonsense mutation where the altered codon corresponds to a stop signal. Silent mutations result in a new codon (a triplet nucleotide sequence in RNA) that codes for the same amino acid as the wild type codon in that position. In some silent mutations the codon codes for a different amino acid that happens to have the same properties as the amino acid produced by the wild type codon. Missense mutations involve substitutions that result in functionally different amino acids; these can lead to alteration or loss of protein function. Nonsense mutations, which are a severe type of base substitution, result in a stop codon in a position where there was not one before, which causes the premature termination of protein synthesis and can result in a complete loss of function in the finished protein.

Generally, conservative substitutions can be made at any position so long as the required activity is retained. So-called conservative exchanges can be carried out in which the amino acid which is replaced has a similar property as the original amino acid, for example, the exchange of Glu by Asp, Gln by Asn, Val by lie, Leu by lie, and Ser by Thr. For example, amino acids with similar properties can be Aliphatic amino acids (e.g., Glycine, Alanine, Valine, Leucine, Isoleucine); hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. An amino acid sequence can be modulated with the help of art-known computer simulation programs that can produce a polypeptide with, for example, improved activity or altered regulation. On the basis of these artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m = 81.5° \text{C.} + 16.6(\log_{10}[\text{Na}^+]) + 0.41$ (fraction G/C content) $- 0.63$(% formamide) $- (600/I)$. Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transformed cells can be selected and propagated to provide recombinant host cells that comprise the expression vector stably integrated in the host cell genome.

| Conservative Substitutions I | |
| --- | --- |
| Side Chain Characteristic | Amino Acid |
| Aliphatic Non-polar | G A P I L V |
| Polar-uncharged | C S T M N Q |
| Polar-charged | D E K R |
| Aromatic | H F W Y |
| Other | N Q D E |

| Conservative Substitutions II | |
| --- | --- |
| Side Chain Characteristic | Amino Acid |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

| Conservative Substitutions III | |
| --- | --- |
| Original Residue | Exemplary Substitution |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met(M) | Leu, Phe, Ile |
| Phe (F) | Leu, Val, Ile, Ala |
| Pro (P) | Gly |
| Ser (S) | Thr |
| Thr (T) | Ser |
| Trp(W) | Tyr, Phe |
| Tyr (Y) | Trp, Phe, Tur, Ser |
| Val (V) | Ile, Leu, Met, Phe, Ala |

Exemplary nucleic acids that may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides (ASOs), protein aptamers, nucleotide aptamers, and RNA interference (RNAi) (e.g., small interfering RNAs (siRNA), short hairpin RNA (shRNA), single guide RNA (sgRNA), and micro RNAs (miRNA) (see e.g., Rinaldi and Wood (2017) Nature Reviews Neurology 14, describing ASO therapies; Fanning and Symonds (2006) Handb Exp Pharmacol. 173, 289-303G, describing hammerhead ribozymes and small hairpin RNA; Helene, et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinformatics & Research Computing). Traits influential in defining optimal siRNA sequences include G/C content at the termini of the siRNAs, $T_m$ of specific internal domains of the siRNA, siRNA length, position of the target sequence within the CDS (coding region), and nucleotide content of the 3' overhangs.

Genome Editing

As described herein, signals can be modulated (e.g., reduced, eliminated, or enhanced) using genome editing.

As described herein, activity, signals, expression, or function can be modulated (e.g., reduced, eliminated, or enhanced) using genome editing (e.g., upregulate, downregulate, overexpress, underexpress, express (e.g., transgenic expression), knock in, knock out, knockdown).

Processes for genome editing are well known; see e.g., Aldi 2018 Nature Communications 9(1911). Except as otherwise noted herein, therefore, the process of the present disclosure can be carried out in accordance with such processes.

For example, genome editing can comprise CRISPR/Cas9, CRISPR-Cpf1, TALEN, or ZNFs.

As an example, clustered regularly interspaced short palindromic repeats (CRISPR)/CRISPR-associated (Cas) systems are a new class of genome-editing tools that target desired genomic sites in mammalian cells. Recently published type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus, a $(N)_{20}NGG$ target DNA sequence). This results in a double-strand break three nucleotides upstream of the NGG motif. The double strand break instigates either non-homologous end-joining, which is error-prone and conducive to frameshift mutations that knock out gene alleles, or homology-directed repair, which can be exploited with the use of an exogenously introduced double-strand or single-strand DNA repair template to knock in or correct a mutation in the genome. Thus, genomic editing, for example, using CRISPR/Cas systems could be useful tools for therapeutic applications to target cells by the removal or addition of signals (e.g., activate (e.g., CRISPRa), upregulate, overexpress, downregulate).

For example, the methods as described herein can comprise a method for altering a target polynucleotide sequence in a cell comprising contacting the polynucleotide sequence with a clustered regularly interspaced short palindromic repeats-associated (Cas) protein.

Gene Therapy and Genome Editing

Gene therapies can include inserting a functional gene with a viral vector. Gene therapies for many diseases are rapidly advancing.

There has recently been an improved landscape for gene therapies. For example, in the first quarter of 2019, there were 372 ongoing gene therapy clinical trials (*Alliance for Regenerative Medicine*, 5/9/19).

Any vector known in the art can be used. For example, the vector can be a viral vector selected from retrovirus, lentivirus, herpes, adenovirus, adeno-associated virus (AAV), rabies, Ebola, lentivirus, or hybrids thereof.

| Gene therapy strategies. | |
|---|---|
| Strategy | |
| Viral Vectors | |
| Retroviruses | Retroviruses are RNA viruses transcribing their single-stranded genome into a double-stranded DNA copy, which can integrate into host chromosome |
| Adenoviruses (Ad) | Ad can transfect a variety of quiescent and proliferating cell types from various species and can mediate robust gene expression |
| Adeno-associated Viruses (AAV) | Recombinant AAV vectors contain no viral DNA and can carry ~4.7 kb of foreign transgenic material. They are replication defective and can replicate only while coinfecting with a helper virus |

-continued

| Gene therapy strategies. | |
|---|---|
| Strategy | |
| Non-viral vectors | |
| plasmid DNA (pDNA) | pDNA has many desired characteristics as a gene therapy vector; there are no limits on the size or genetic constitution of DNA, it is relatively inexpensive to supply, and unlike viruses, antibodies are not generated against DNA in normal individuals |
| RNAi | RNAi is a powerful tool for gene specific silencing that could be useful as an enzyme reduction therapy or means to promote read-through of a premature stop codon |

Gene therapy can allow for the constant delivery of the enzyme directly to target organs and eliminates the need for weekly infusions. Also, correction of a few cells could lead to the enzyme being secreted into the circulation and taken up by their neighboring cells (cross-correction), resulting in widespread correction of the biochemical defects. As such, the number of cells that must be modified with a gene transfer vector is relatively low.

Genetic modification can be performed either ex vivo or in vivo. The ex vivo strategy is based on the modification of cells in culture and transplantation of the modified cell into a patient. Cells that are most commonly considered therapeutic targets for monogenic diseases are stem cells. Advances in the collection and isolation of these cells from a variety of sources have promoted autologous gene therapy as a viable option.

The use of endonucleases for targeted genome editing can solve the limitations presented by the usual gene therapy protocols. These enzymes are custom molecular scissors, allowing cutting DNA into well-defined, perfectly specified pieces, in virtually all cell types. Moreover, they can be delivered to the cells by plasmids that transiently express the nucleases, or by transcribed RNA, avoiding the use of viruses.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutically active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic, or other physical forces.

Controlled-release (or sustained-release) preparations may be formulated to extend the activity of the agent(s) and reduce dosage frequency. Controlled-release preparations can also be used to affect the time of onset of action or other characteristics, such as blood levels of the agent, and consequently, affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided are processes of providing gene therapy and/or treating, preventing, or reversing cancer in a subject in need thereof by administration of a conjugate system comprising mRNA as disclosed herein. In some embodiments, the mRNA encodes a cancer neoantigen, so as to elicit neoantigen-specific T cell responses in the subject, reduce tumor size, or increase survival.

Methods described herein are generally performed on a subject in need thereof. A subject in need of the therapeutic methods described herein can be a subject having, diagnosed with, suspected of having, or at risk for developing cancer. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans or chickens. For example, the subject can be a human subject.

Generally, a safe and effective amount of a conjugate system comprising mRNA encoding a cancer neoantigen is, for example, an amount that would cause the desired therapeutic effect in a subject while minimizing undesired side effects. In various embodiments, an effective amount of a conjugate system comprising mRNA encoding a cancer neoantigen described herein can substantially inhibit tumor growth, slow the progress of tumor growth, or limit the development of tumors.

According to the methods described herein, administration can be parenteral, pulmonary, oral, topical, intradermal, intramuscular, intraperitoneal, intravenous, intratumoral, intrathecal, intracranial, intracerebroventricular, subcutaneous, intranasal, epidural, ophthalmic, buccal, or rectal administration.

When used in the treatments described herein, a therapeutically effective amount of a conjugate system comprising mRNA encoding a cancer neoantigen can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to elicit neoantigen-specific T cell responses in the subject, reduce tumor size, or increase survival.

The amount of a composition described herein that can be combined with a pharmaceutically acceptable carrier to produce a single dosage form will vary depending upon the subject or host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4$^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes reversing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or a physician.

Administration of a conjugate system comprising mRNA encoding a cancer neoantigen can occur as a single event or over a time course of treatment. For example, a conjugate system comprising mRNA encoding a cancer neoantigen can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to or before, concurrent with, or after conventional treatment modalities for cancer.

A conjugate system comprising mRNA encoding a cancer neoantigen can be administered simultaneously or sequentially with another agent, such as an antibiotic, an anti-inflammatory, or another agent. For example, a conjugate system comprising mRNA encoding a cancer neoantigen can be administered simultaneously with another agent, such as an antibiotic or an anti-inflammatory. Simultaneous administration can occur through administration of separate compositions, each containing one or more of a conjugate system comprising mRNA encoding a cancer neoantigen, an antibiotic, an anti-inflammatory, or another agent. Simultaneous administration can occur through administration of one composition containing two or more of a conjugate system comprising mRNA encoding a cancer neoantigen, an anti-biotic, an anti-inflammatory, or another agent. A conjugate system comprising mRNA encoding a cancer neoantigen can be administered sequentially with an antibiotic, an anti-inflammatory, or another agent. For example, a conjugate system comprising mRNA encoding a cancer neoantigen can be administered before or after administration of an antibi-otic, an anti-inflammatory, or another agent.

Active compounds are administered at a therapeutically effective dosage sufficient to treat a condition associated with a condition in a patient. For example, the efficacy of a compound can be evaluated in an animal model system that may be predictive of efficacy in treating the disease in a human or another animal, such as the model systems shown in the examples and drawings.

An effective dose range of a therapeutic can be extrapo-lated from effective doses determined in animal studies for a variety of different animals. In general, a human equivalent dose (HED) in mg/kg can be calculated in accordance with the following formula (see e.g., Reagan-Shaw et al., *FASEB J.,* 22(3):659-661, 2008, which is incorporated herein by reference):

$$\text{HED (mg/kg)} = \text{Animal dose(mg/kg)} \times (\text{Animal}K_m / \text{Human}K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment, and the potency, stability, and toxicity of the particular therapeutic formulation.

The actual dosage amount of a compound of the present disclosure or composition comprising a compound of the present disclosure administered to a subject may be deter-mined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for adminis-tration will typically determine the concentration of active ingredient(s) in a composition and appropriate dose(s) for the individual subject. The dosage may be adjusted by the individual physician in the event of any complication.

In some embodiments, the conjugate system comprising mRNA encoding a cancer neoantigen may be administered in an amount from about 1 mg/kg to about 100 mg/kg, or about 1 mg/kg to about 50 mg/kg, or about 1 mg/kg to about 25 mg/kg, or about 1 mg/kg to about 15 mg/kg, or about 1 mg/kg to about 10 mg/kg, or about 1 mg/kg to about 5 mg/kg, or about 3 mg/kg. In some embodiments, a conjugate system comprising mRNA encoding a cancer neoantigen as described herein may be administered in a range of about 1 mg/kg to about 200 mg/kg, or about 50 mg/kg to about 200 mg/kg, or about 50 mg/kg to about 100 mg/kg, or about 75 mg/kg to about 100 mg/kg, or about 100 mg/kg.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day.

In other non-limiting examples, a dose may also comprise from about 1 microgram/kg/body weight, about 5 micro-gram/kg/body weight, about 10 microgram/kg/body weight, about 50 microgram/kg/body weight, about 100 microgram/kg/body weight, about 200 microgram/kg/body weight, about 350 microgram/kg/body weight, about 500 micro-gram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 micro-gram/kg/body weight to about 500 milligram/kg/body weight, etc., can be administered, based on the numbers described above.

Administration

Agents and compositions described herein can be admin-istered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufac-tured inside the body by some type of device (biologic or other) for delivery within or to other organs in the body.

As discussed above, administration can be parenteral, pulmonary, oral, topical, intradermal, intratumoral, intrana-sal, inhalation (e.g., in an aerosol), implanted, intramuscular, intraperitoneal, intravenous, intrathecal, intracranial, intrac-erebroventricular, subcutaneous, intranasal, epidural, intrathecal, ophthalmic, transdermal, buccal, and rectal.

Agents and compositions described herein can be admin-istered in a variety of methods well known in the arts. Administration can include, for example, methods involving oral ingestion, direct injection (e.g., systemic or stereotac-tic), implantation of cells engineered to secrete the factor of interest, drug-releasing biomaterials, polymer matrices, gels, permeable membranes, osmotic systems, multilayer coat-ings, microparticles, implantable matrix devices, mini-os-motic pumps, implantable pumps, injectable gels and hydro-gels, liposomes, micelles (e.g., up to 30 μm), nanospheres (e.g., less than 1 μm), microspheres (e.g., 1-100 μm), res-ervoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or com-position in a manner similar to that used for delivering insulin or chemotherapy to specific organs or tumors. Typi-cally, using such a system, an agent or composition can be administered in combination with a biodegradable, biocom-patible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency; improve taste of the product; or improve shelf life of the product.

Screening

Also provided are screening methods.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 MW, or less than about 1000 MW, or less than about 800 MW) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl, or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example, ChemBridge, Princeton BioMolecular, Ambinter SARL, Enamine, ASDI, Life Chemicals, etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character xlogP of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character xlogP of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical success if it is drug-like.

Several of these "drug-like" characteristics have been summarized into the four rules of Lipinski (generally known as the "rules of fives" because of the prevalence of the number 5 among them). While these rules generally relate to oral absorption and are used to predict the bioavailability of a compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to adenovirus, peptide tags, binding partners, gRNA, mRNA, linkers, targeting peptides or adapters, or cells. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline each of which has been packaged under a neutral non-reacting gas, such as nitrogen. Ampules may consist of any suitable material, such as glass, organic polymers, such as polycarbonate, polystyrene, ceramic, metal, or any other material typically employed to hold reagents. Other examples of suitable containers include bottles that may be fabricated from similar substances as ampules and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or another substrate, and/or may be supplied as an electronic-readable medium or video. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Efficient Genome Editing Achieved Via Plug-and-Play Adenovirus Piggyback Transport of Cas9/Grna Complex on Viral Capsid Surface This Example describes a modular synthetic approach to efficiently derive adenoviral vectors carrying a large and complex functionality on virus surface.

The capacity to efficiently deliver the gene-editing enzyme complex to target cells is favored over other forms of gene delivery as it offers one-time hit-and-run gene editing, thus improving precision and safety and reducing potential immunogenicity against edited cells in clinical applications. Herein is described a proof-of-mechanism study, wherein a simian adenoviral vector for DNA delivery was repurposed as a robust intracellular delivery platform for a functional Cas9/guide RNA (gRNA) complex to recipient cells. In this system, the clinically relevant adenovirus was genetically engineered with a plug-and-display technology based on SpyTag003/SpyCatcher003 coupling chemistry (see e.g., FIG. 1). Under physiological conditions, an off-the-shelf mixture of viral vector with SpyTag003 incorporated into surface capsid proteins and Cas9 fused with SpyCatcher003 led to a rapid titration reaction yielding adenovirus carrying Cas9SpyCatcher003 on the virus surface. The Cas9 fusion protein-conjugated viruses in the presence of a reporter gRNA delivered gene-editing functions to cells with an efficiency comparable to that of a commercial CRISPR/Cas9 transfection reagent. The data fully validate the adenoviral "piggyback" approach to deliver an intracellularly acting enzyme cargo and, thus, warrant the prospect of engineering tissue-targeted adenovirus carrying Cas9/gRNA for in vivo gene editing.

Introduction

The recent advent of a group of genetic manipulation enzymes, the clustered regularly interspaced short palindromic repeats (CRISPR)-associated protein (Cas) systems, represents a revolutionary advancement in the technology of precise and versatile gene editing and holds the promise of treating a great variety of inherited and acquired diseases. The mainstay of Cas-mediated gene-editing strategies rely on introducing DNA sequences encoding an editor and guide RNA (gRNA) to the nucleus of target cells via viral or nonviral methods. The DNA delivery, however, runs the risk of insertional mutagenesis by some of the viral vector systems and plasmid DNA. Such DNA methods also result in production of Cas protein long after the on-target editing events are achieved, the undesired persistent Cas expression potentially increases off-target editing events and elicits a host adaptive immune response attacking the edited cells. The recently emerging mRNA delivery systems allow transient expression of editors, thus circumventing the concerns of the DNA approach. However, delivery of mRNA has the limitations of triggering innate immunogenicity against cells uptaking exogenous mRNA and susceptibility of mRNA to enzymatic degradation in blood and the periphery.

In this regard, protein-based formulations also offer one-time hit-and-run gene editing but, unlike mRNA, have a far smaller tendency of inducing an acute immune response, thus conferring improved specificity and enhanced safety over nucleic acid approaches. In this regard, Cas is a gRNA sequence-dependent DNA endonuclease, and purified Cas can directly bind in vitro transcribed or synthesized gRNA to form the active ribonucleoprotein (RNP) enzyme complex. Exogenous Cas RNP complex, however, like many other intracellularly acting protein and nucleic acid biologics, requires a delivery reagent to facilitate its intracellular uptake. To date, gene editor RNPs have been delivered mainly using nonviral methods. As an alternative, it was hypothesized that gene therapy viral vectors for DNA delivery could be repurposed as a powerful carrier platform for intracellular delivery of RNPs. In this regard, adenovirus, in particular, possesses a number of salient features relevant to its employ as a robust RNP carrier.

Adenoviral vectors have been engineered to efficiently infect a broad range of tissues with tissue specificity through the genetic capsid incorporation of targeting peptides or the use of targeting adapters. Importantly, adenovirus has naturally evolved an infection pathway that can efficiently deliver viral DNA as well as its major capsid proteins into the cytoplasm of host cells. This process involves the receptor-mediated endocytosis of whole virion particles by the host cell membrane followed by release of viral proteins and DNA to the cytoplasm through lysosomal mechanisms. In this regard, the adenoviral delivery of exogenous nucleic acids was previously demonstrated using a viral capsid conjugate system, where the adenovirus-bound nucleic acids were efficiently cointernalized and entered the cells along with other viral components, leading to therapeutic gene expression in target cells. On this basis, it was hypothesized that a preassembled Cas RNP complex conjugated on the surface of adenovirus would also be intracellularly delivered through the same mechanism.

Herein is described a proof-of-mechanism study that demonstrated highly efficient gene editing in cells infected with adenovirus carrying Cas9/gRNA on its capsid proteins. For this, a recombinant protein-virus crosslinking strategy was developed by employing a SpyTag003/SpyCatcher003 conjugation system. In this system, a nuclear localization signal-loaded Cas9 was fused with SpyCatcher003, and the Cas9SpyCatcher003 protein possessed CRISPR nuclease activity comparable to that of a marketed Cas9. The genetic incorporation of SpyTag003 to a simian adenovirus capsid fiber or hexon was further achieved. Both SpyTag003 viruses potentiated efficient conjugation of Cas9SpyCatcher003 in a rapid, spontaneous, and titratable fashion. Cas9SpyCatcher003-conjugated viruses in the presence of a reporter gRNA delivered gene-editing capacity to cells in a dose-dependent fashion. The efficiency attained by the viral delivery approach was comparable to that of a commercial CRISPR/Cas transfection reagent.

Results/Discussion

Recombinant Cas9SpC Retained CRISPR Nuclease Activity

Figures 2A, 2B:
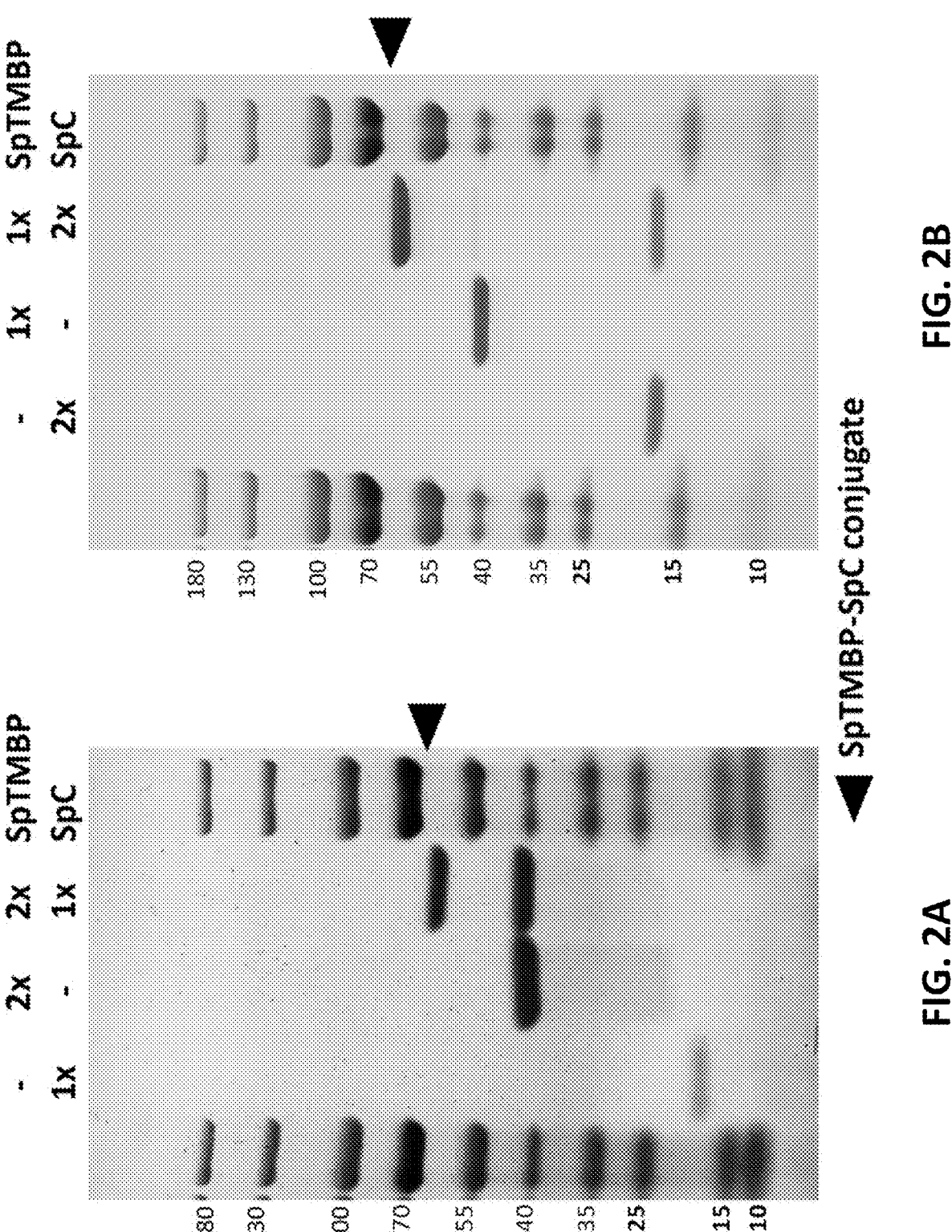
FIG. 2A-2B is an exemplary embodiment showing that the conjugation reaction of SpC and SpT was spontaneous and in a titratable fashion in accordance with the present disclosure. SpC and SpT fused with maltose binding protein (SpTMBP) were mixed in phosphate-buffered saline and incubated at 37° C. for two hours. 37.5 pmol of SpC and 75.0 pmol of SpTMBP (1:2 SpT:SpC ratio) were used in FIG. 2A and 150.0 pmol of SpC and 75.0 pmol of SpTMBP (2:1 SpT:SpC ratio) were used in FIG. 2B. SpC: SpyCatcher003; SpTMBP: SpyTag003MBP; Cas9SpC: SpCas9 fused with SpyCatcher003.
Figures 3, 4:
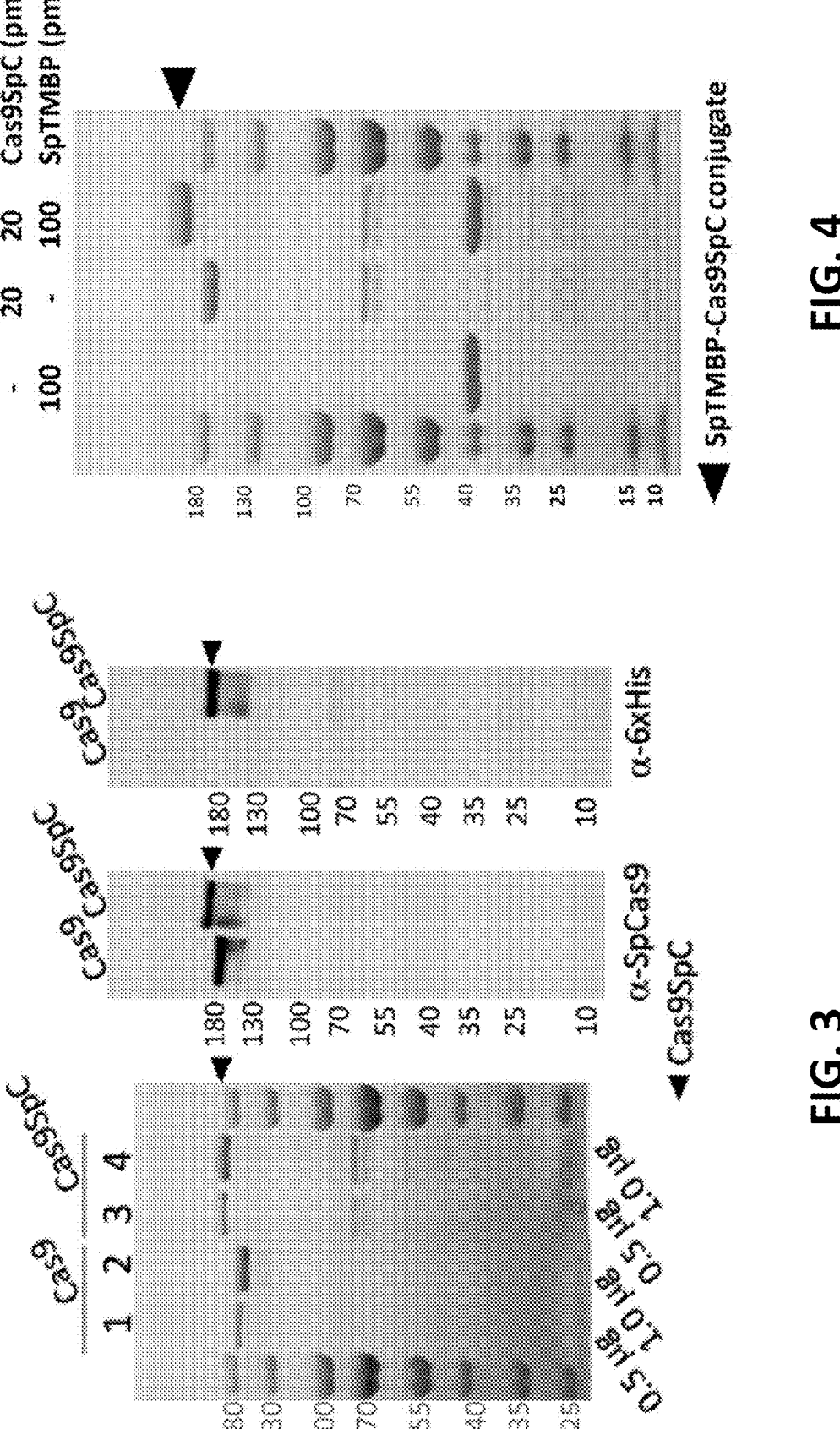
FIG. 3 is an exemplary embodiment showing Cas9SpC retained CRISPR nuclease activity in accordance with the present disclosure.
FIG. 4 is an exemplary embodiment showing that the conjugation reaction of SpC and SpT was spontaneous and in a titratable fashion in accordance with the present disclosure. 20.0 pmol of Cas9SpC and 100.0 pmol of SpTMBP (5:1 SpTMBP:Cas9SpC ratio) were mixed in phosphate-buffered saline and incubated at 37° C. for two hours. The reaction mixtures were boiled in SDS sample buffer and resolved by SDS-PAGE with Coomassie blue staining. SpC: SpyCatcher003; SpTMBP: SpyTag003MBP; Cas9SpC: SpCas9 fused with SpyCatcher003.

It was desired to conjugate recombinant *Streptococcus pyogenes* Cas9 (SpCas9) to adenovirus and explore the viral infection pathway as a "piggyback" route to deliver CRISPR genome editing to target cells. A third-generation SpyTag003/SpyCatcher003 system was chosen to develop the protein—virus cross-linking approach. As expected, the covalent ligation chemistry between SpyCatcher003 (SpC hereafter) and SpyTag003 (SpT hereafter) in phosphate-buffered saline at 37° C. was spontaneous, occurred in a titratable fashion, and reached completion within 1-2 h (see e.g., FIG. 2A-FIG. 2B). Next, SpCas9 incorporated with three nuclear localization signals (3×NLS_SpCas9) in fusion with SpC_6×His linked by a flexible peptide between the two moieties was designed and produced. The resultant 3×NLS_SpCas9_linker SpC_6×His (Cas9SpC hereafter) was about 20 kDa larger than the NLS-incorporated TrueCut SpCas9 v2 (ThermoFisher Scientific, see e.g., FIG. 3, left panel). Immunoblot analysis with SpCas9- and 6×His-specific antibodies confirmed the identity of the produced protein (see e.g., FIG. 3, middle and right panels). This protein, like SpC, showed complete accessibility for conjugation by SpT supplied in an excess amount, further confirming its identity as Cas9SpC (see e.g., FIG. 4)

Figure 5:
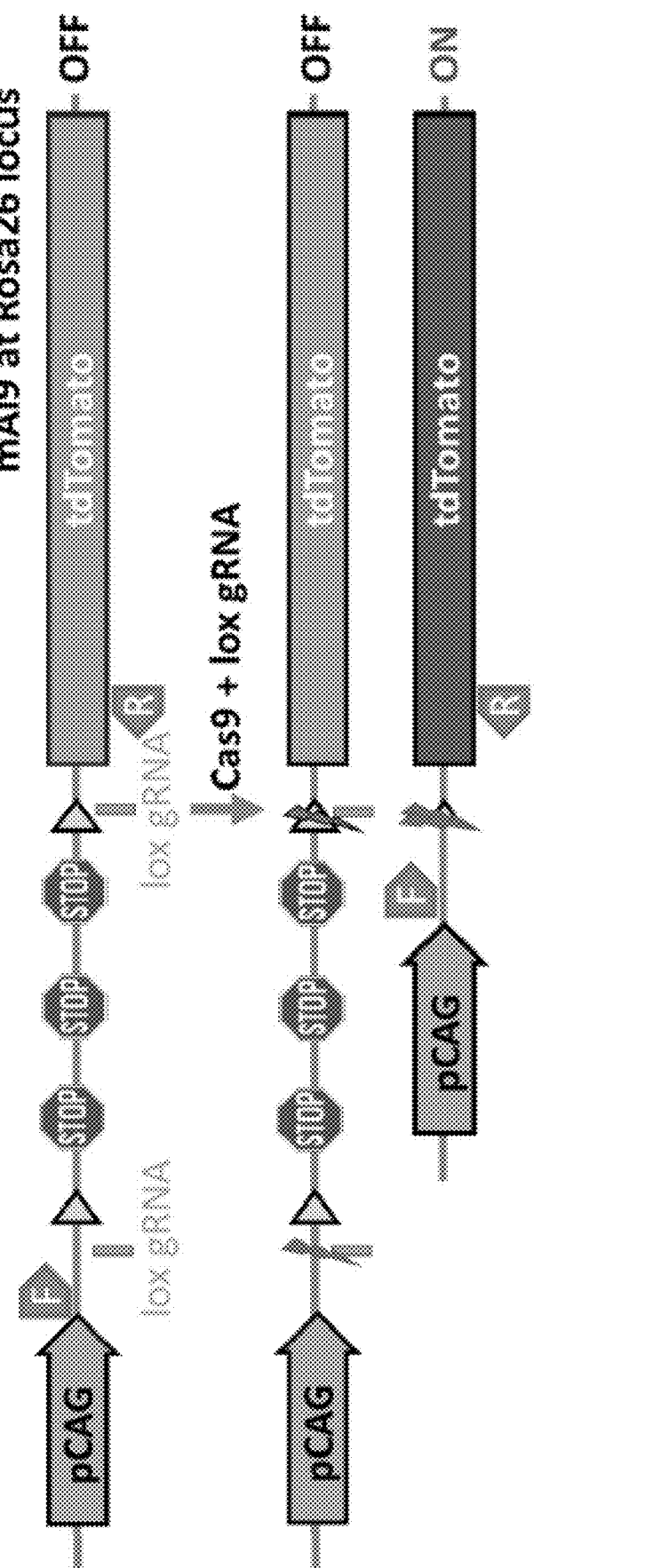
FIG. 5 is an exemplary embodiment showing Cas9SpC retained CRISPR nuclease activity in accordance with the present disclosure.
Figures 6A, 6B:
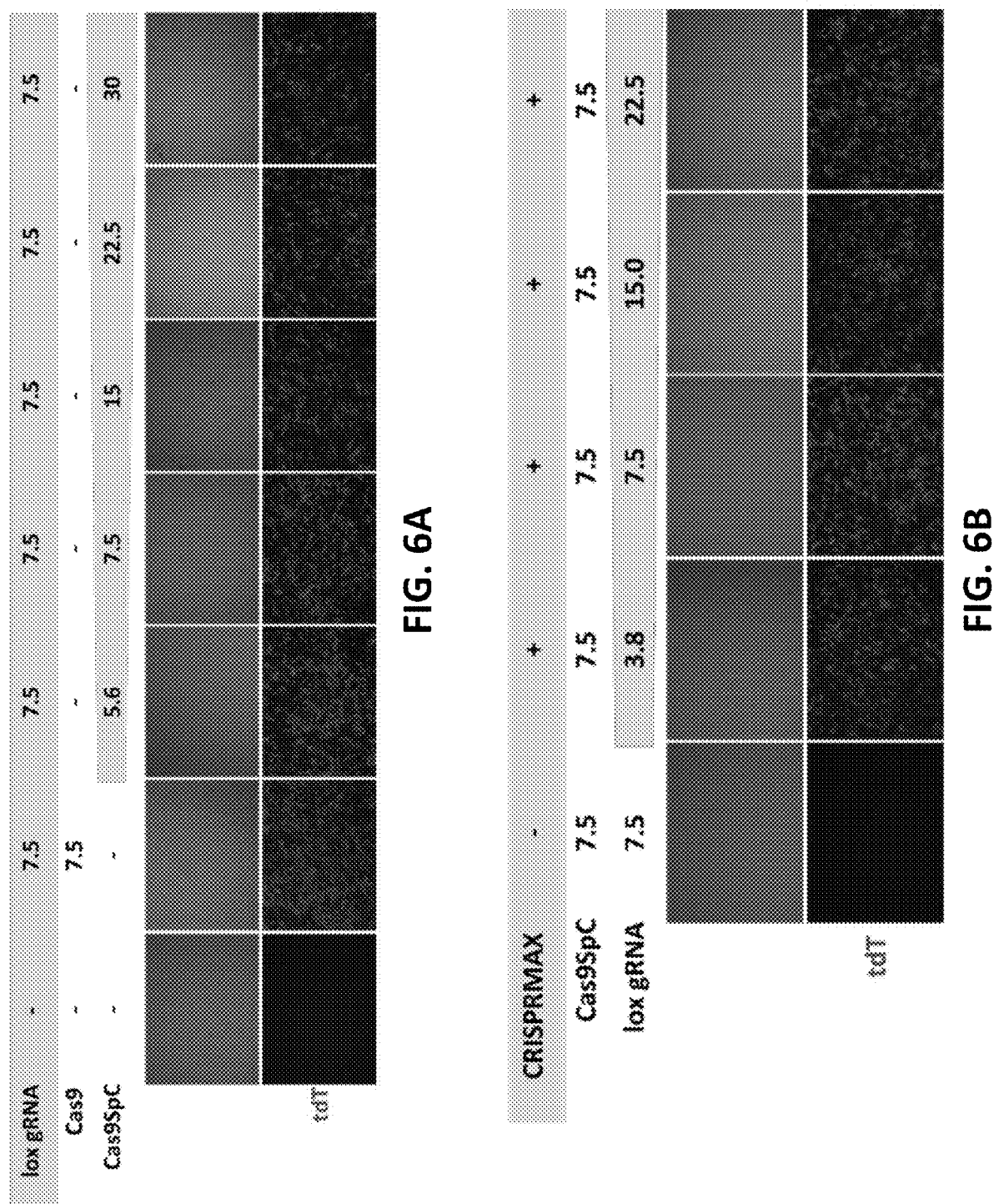
FIG. 6A-FIG. 6B is an exemplary embodiment showing Cas9SpC retained CRISPR nuclease activity in accordance with the present disclosure.
Figure 7A:
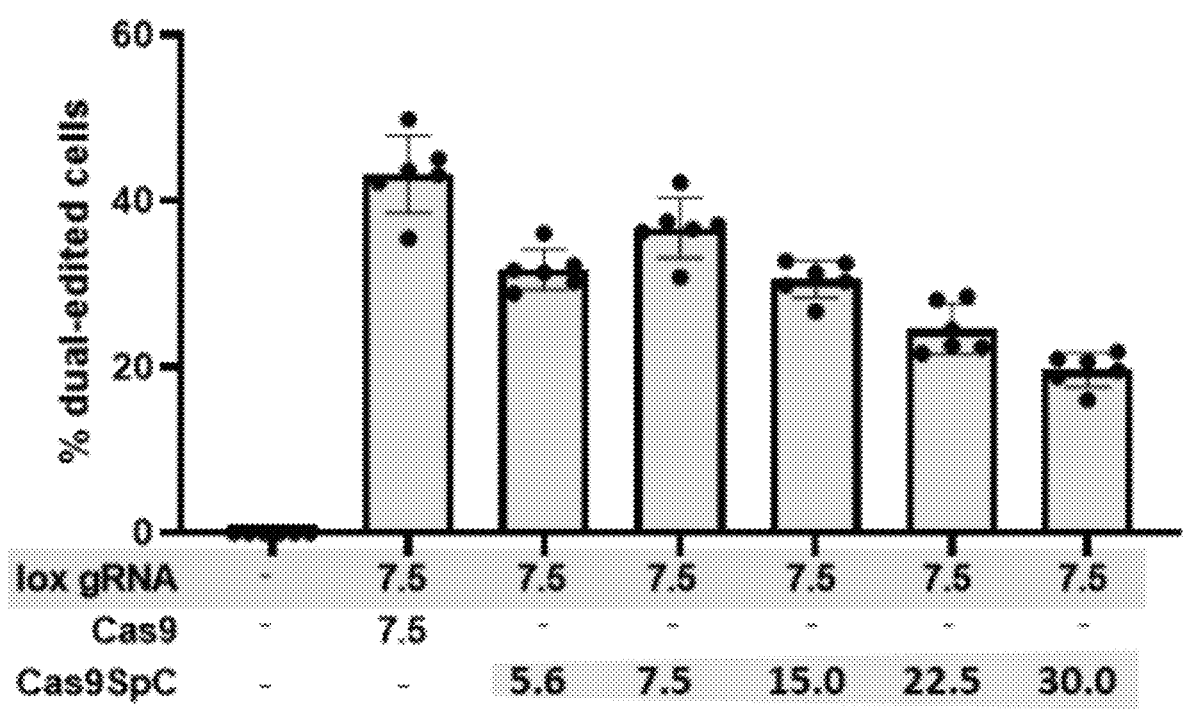
FIG. 7A-FIG. 7D is an exemplary embodiment showing Cas9SpC retained CRISPR nuclease activity in accordance with the present disclosure.
Figure 7B:
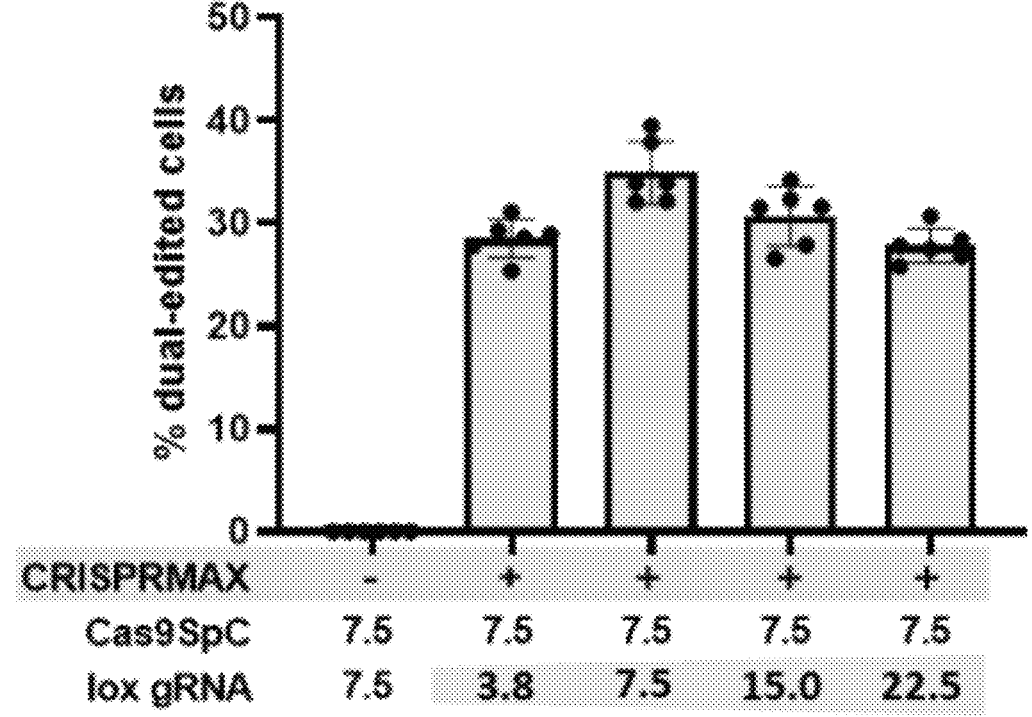
Figure 7C:
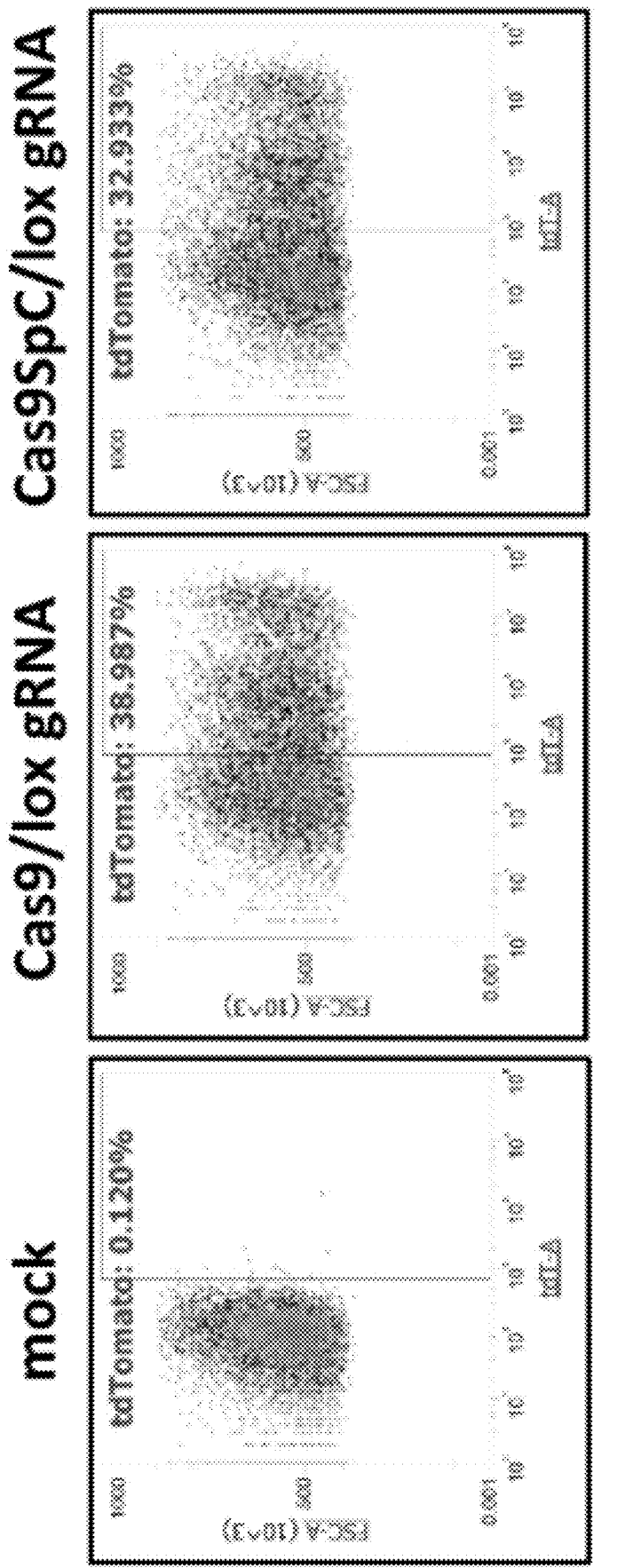
Figure 7D:
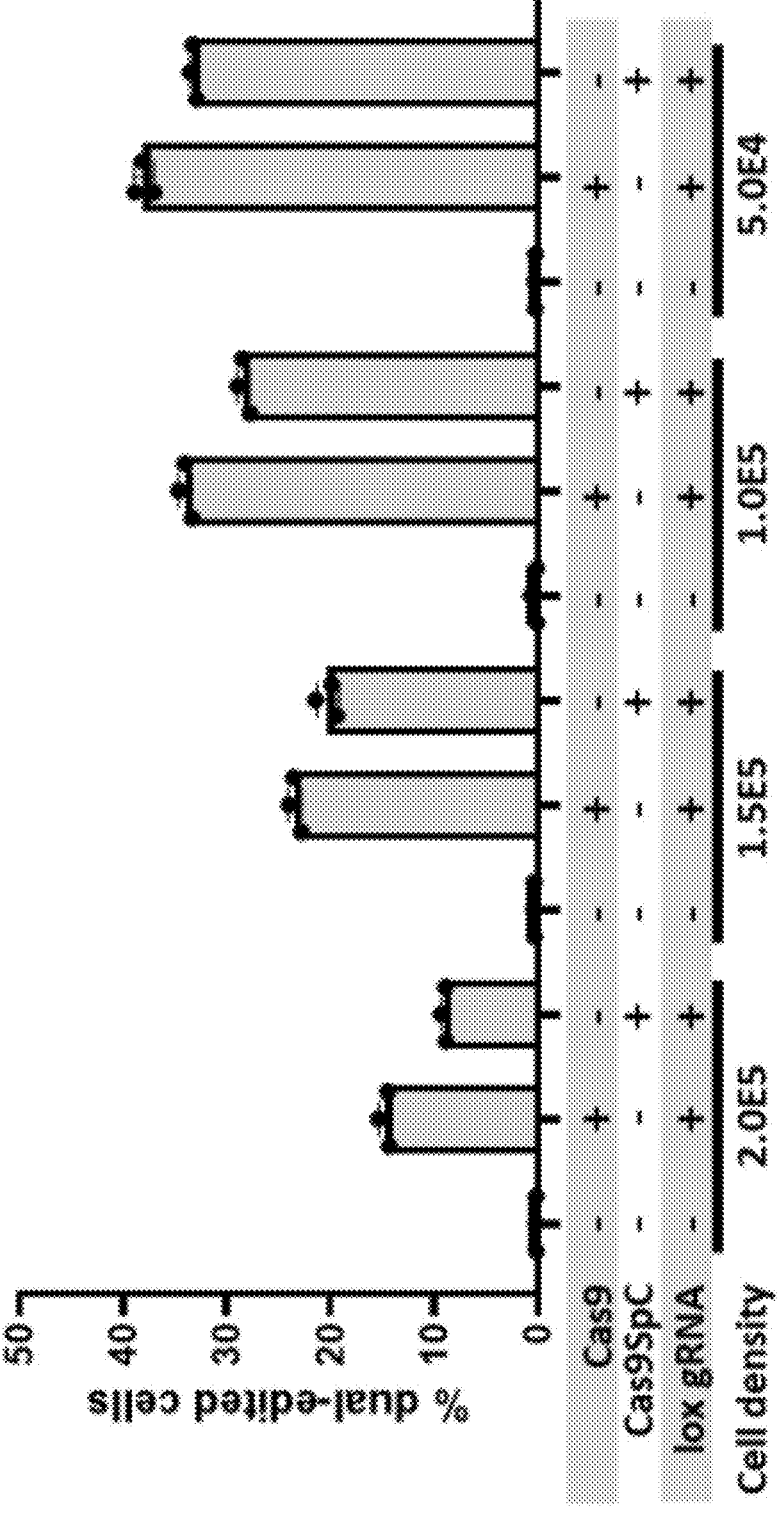

To test the CRISPR nuclease activity of Cas9SpC, an NIH somatic cell genome editing (SCGE) program-established modified Ai9 (Rosa26: Ai9-SauSpyCas9-tdTomato or mAi9) reporter system available in both mice and cell line (MGI reference ID: J:302103; see e.g., FIG. 5) was employed. In this system, a single guide RNA (lox gRNA) recognizing two sites flanking a transcriptional STOP cassette in the Rosa26-tdTomato locus directs Cas9-mediated dual cleavage and deletion of this cassette. The resultant dual-edited locus subsequently activates expression of downstream tdTomato gene, and as such, the red fluorescent protein signals serve as a surrogate marker for cells possessing the dual-edited allele. The TrueCut Cas9 v2 (Cas9 hereafter)/lox gRNA was included as a CRISPR nuclease activity reference control, and delivery of the editors to mAi9 mouse embryonic fibroblasts was achieved using lipofectamine CRISPRMAX reagent. Robust CRISPR gene editing was detected in cells receiving Cas9/lox gRNA as well as in cells receiving Cas9SpC/lox gRNA (see e.g., FIG. 6A-FIG. 6B and FIG. 7A-FIG. 7D). The dose response by varying the amount of both Cas9SpC (see e.g., FIG. 6A and FIG. 7A) and lox gRNA (see e.g., FIG. 6B and FIG. 7B) and by changing the seeding cell density (see e.g., FIG. 7C and FIG. 7D) defined an optimized dose regimen/cell density that produced 33.3%±9.3% (mean±SD hereafter) dual-edited cells by flow cytometry analysis. The equivalent molar dose of Cas9/gRNA yielded 38.0%±1.0% dual-edited cells, suggesting that Cas9SpC possessed about 88% of Cas9 nuclease activity.

Genetic Incorporation of SpT into Simian Adenovirus 36 Capsid Proteins for Functional Anchoring Simian (chimpanzee) adenovirus species E serotype 36 (SAd36) was chosen to engineer SpT-incorporated virus. SAd36 showed low prevalence of pre-existing neutralizing antibodies in human populations and has recently emerged as a vaccine platform in preclinical studies and clinical trials with a favorable safety profile. Importantly, SAd36 exhibited low native tropism in mice when systemically administered but achieved efficient vector targeting via genetic modification of capsid proteins, making it a promising vector for clinical targeted gene therapy applications (unpublished data). To this end, SAd36 with SpT incorporated into two capsid proteins, fiber and hexon, was successfully derived. In the former, the fiber knob domain with an inward C-terminus was replaced by a bacteriophage T4 fibritin fold-on domain with an outward C-terminus to display SpT, yielding the SAd36.fiber-T4 fibritin-SpT (SAd36.FFSpT) vector (see e.g., FIG. 8A). Importantly, the T4 fibritin domain also provided the fiber trimerization function of the knob domain, which was required for successful virion assembly. In the hexon, an outward, 9-residue hypervariable region 5 loop was identified via phylogenetic analysis of human and simian viral proteins and replaced with SpT flanked by two 15-residue flexible linkers, producing the SAd36.hexon-SpT (SAd36.HSpT) vector (see e.g., FIG. 8B).

The two SpT vectors differed significantly in the abundance of SpT displayed on the virion surface with 36 FFSpT monomers and 720 HSpT monomers per virion, respectively (see e.g., FIG. 9A-FIG. 9B, left panels). Viruses were successfully rescued from the two SpT viral genomes, and both viruses grew robustly during upscaling and yielded high-titer preparations. Viral protein composition analysis revealed the presence of protein bands with predicted molecular weights of the modified fiber and modified hexon in respective viral preparations (see e.g., FIG. 9A-FIG. 9B, right panels).

Efficient Covalent Attachment of Cas9SpC to Virus Capsid Via SpT Anchor

Figure 11B:
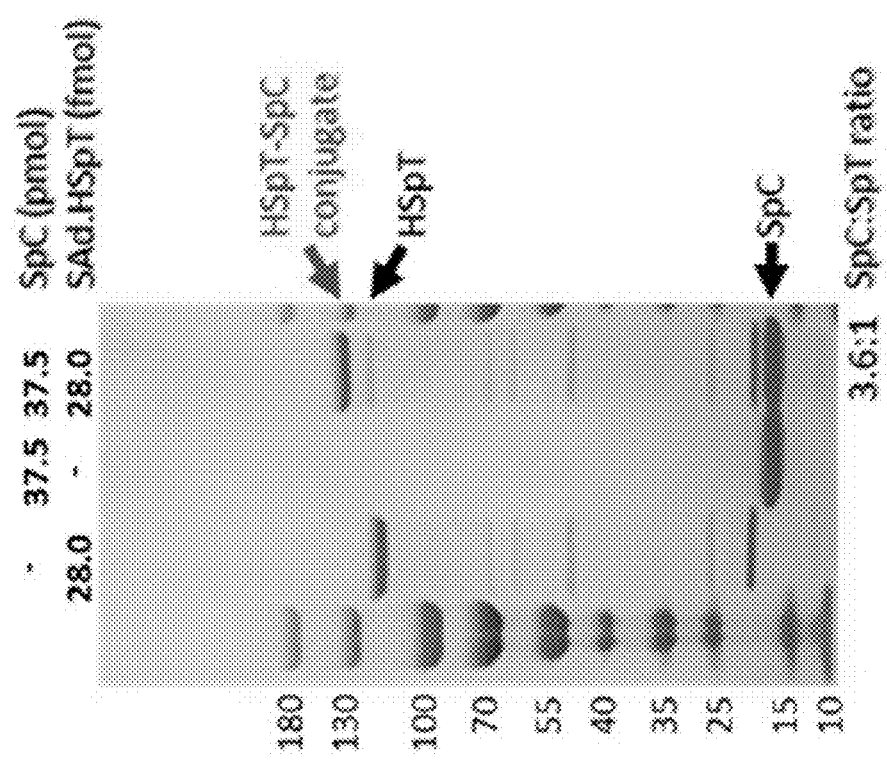
FIG. 11A-FIG. 11D is an exemplary embodiment showing covalent attachment of SpC and Cas9SpC to the SpT viruses in accordance with the present disclosure. SAd36.FFSpT (FIG. 11A) or SAd36.HSpT (FIG. 11B) was incubated with SpC at the designated amounts at 37° C. for 2 h followed by boiling in SDS sample buffer and SDS-PAGE analysis with Coomassie staining. SAd36.FFSpT (FIG. 11C) or SAd36.HSpT (FIG. 11D) was incubated with Cas9SpC at the designated amounts at 37° C. for 2 h followed by boiling in SDS sample buffer and SDS-PAGE analysis with Coomassie staining. The molar ratio of SpC or Cas9SpC versus virus-incorporated SpT in the protein-virus conjugation reaction is provided under each lane.
Figure 11A:
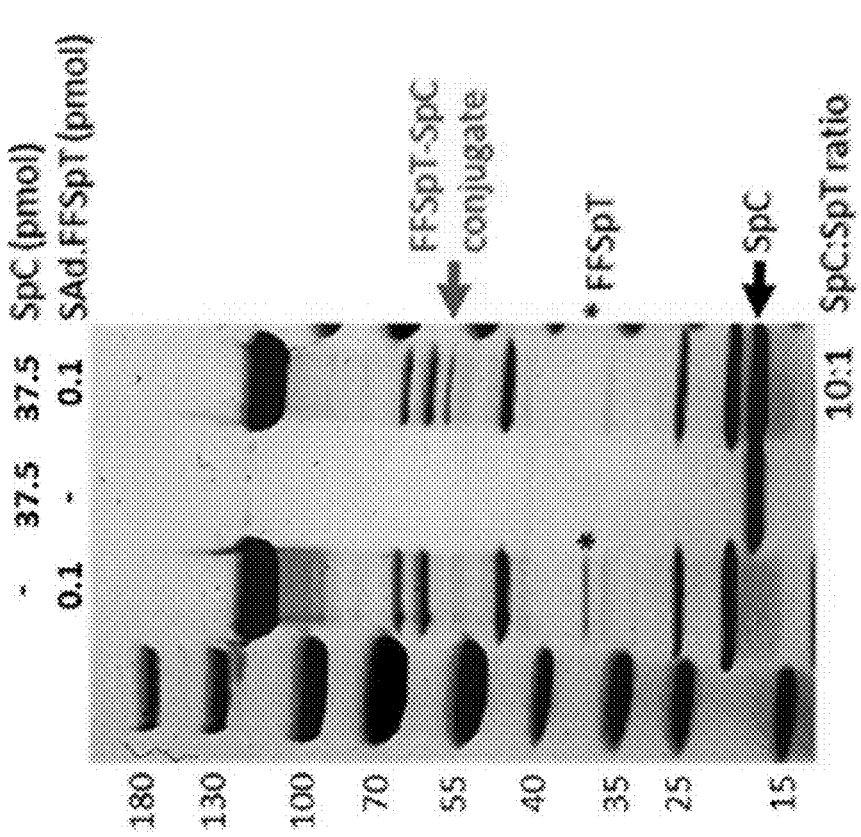
Figure 11D:
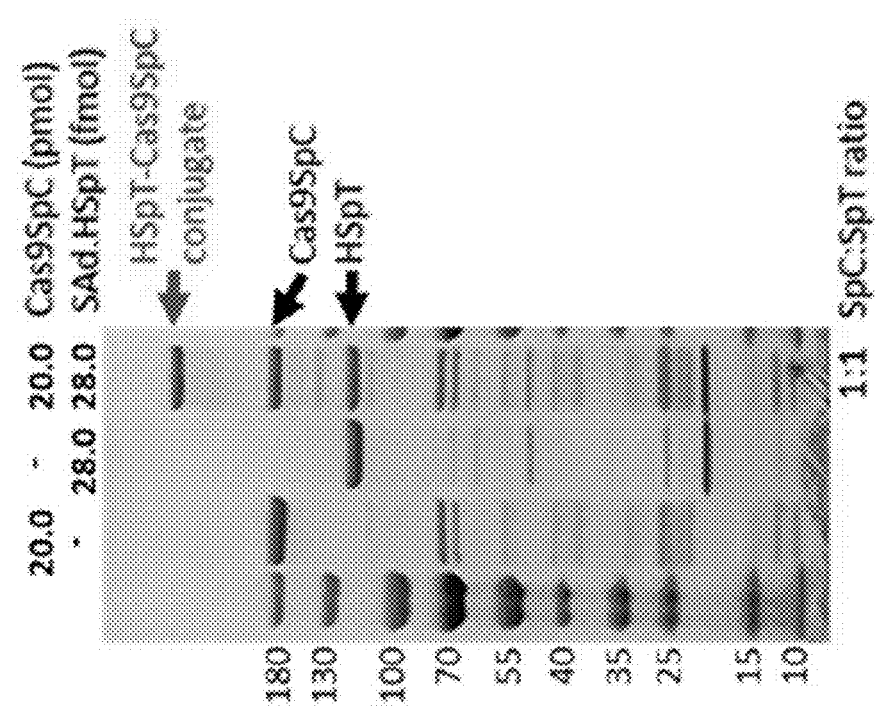
Figure 11C:
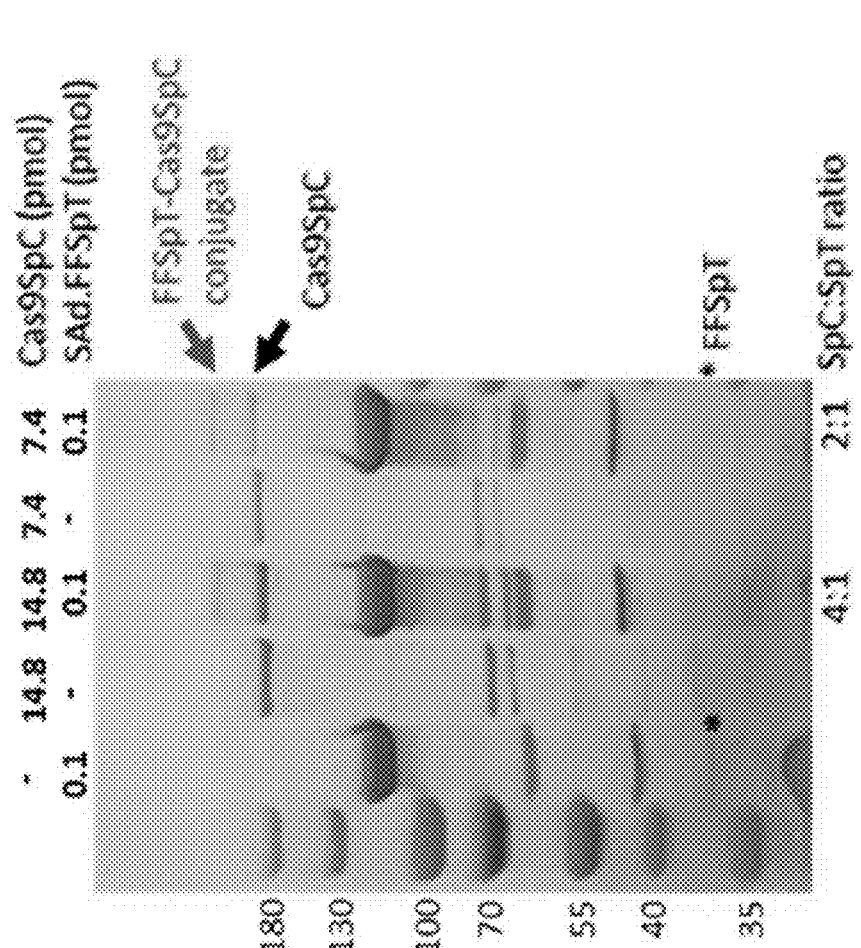
Figure 12:
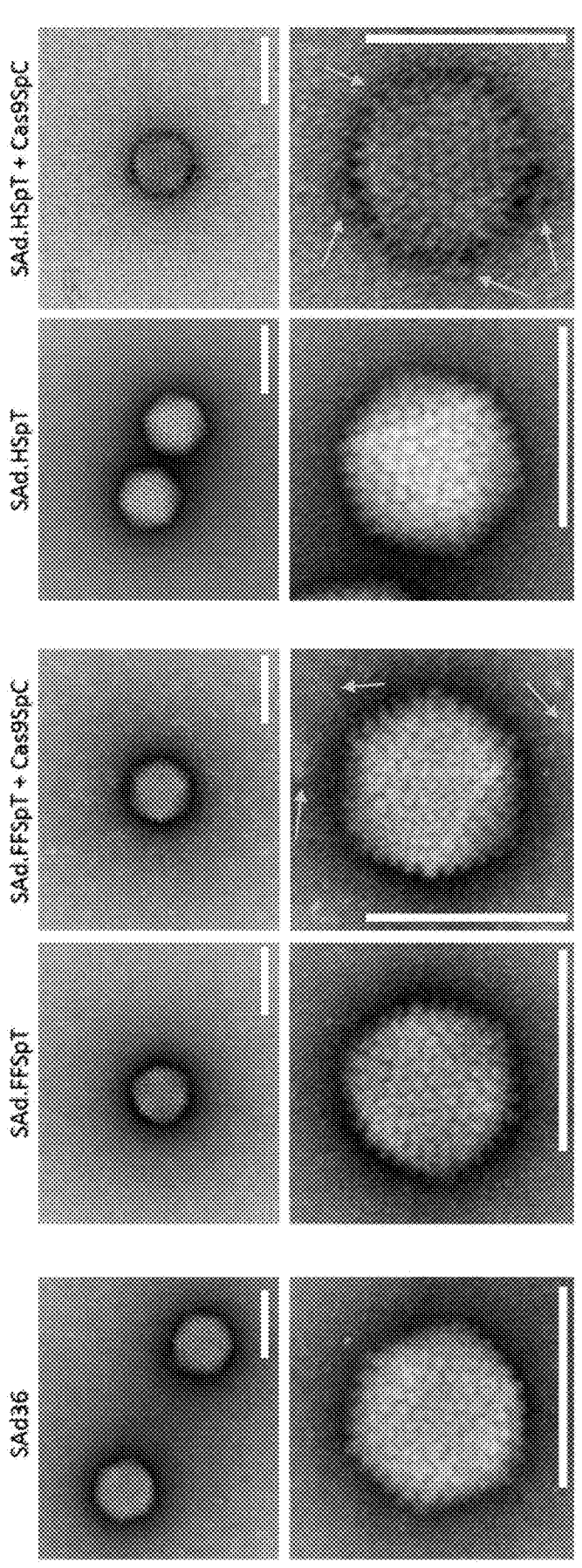
FIG. 12 contains images showing conjugation with Cas9SpC on SpT SAd36 capsid proteins maintained virus morphology in accordance with the present disclosure. Transmission electron micrograph of negatively stained viral particles of SAd36, SAd36.FFSpT, SAd36.FFSpT conjugated with Cas9SpC, SAd36.HSpT, and SAd36.HSpT conjugated with Cas9SpC. Arrows indicate the potential locations of conjugated Cas9SpC on viruses. Scale bar represents 100 nm.

The conjugation chemistry between SpT and SpC is highly specific. Consistent with this notion, there was a lack of detectable nonspecific covalent cross-linking between Cas9SpC and wild-type SAd36 viral proteins following a 2-h incubation (see e.g., FIG. 10). It was intended that SpT be incorporated into sites on the fiber and hexon for its optimal accessibility to SpC and, therefore, the reactivity of SpC to SAd36.FFSpT and SAd36.HSpT was tested using the same assay. An excess amount of SpC versus viral SpT abundance efficiently titrated FFSpT and HSpT to SpC conjugate forms (see e.g., FIG. 11A, FFSpT-SpC conjugate, and FIG. 11B, HSpT-SpC conjugate), thus validating the vector engineering design. Compared with the small SpC protein of 15 kDa, the molecular weight of Cas9SpC is 180 kDa. In this regard, the bulky Cas9SpC retained the capacity of conjugation with all 36 FFSpT sites on the virion (see e.g., FIG. 11C). The Cas9SpC also efficiently converted about half of the 720 HSpT sites to the Cas9SpC-conjugate form (see e.g., FIG. 11D), implying that steric hindrance between free and virus-conjugated Cas9SpC molecules prevented the conjugation of the rest of the viral HSpT sites. Transmission electron microscopy analysis revealed an indistinguishable virion morphology among SAd36, SAd36.FFSpT, and SAd36.HSpT and confirmed that conjugation of Cas9SpC on SAd36.FFSpT and SAd36.HSpT surfaces had a minimal impact on the virion morphology (see e.g., FIG. 12)

In aggregate, a modular synthetic approach was pioneered to efficiently derive adenoviral vectors carrying a large and complex functionality on the virus surface. Specifically, SpT was successfully introduced onto two different surface sites of SAd36 and cross-linking of a Cas9 moiety (160 kDa) fused with SpC (15 kDa) to the engineered viruses was subsequently achieved. Noticeably, the approach overcomes some of the limitations of current adenoviral engineering technologies. First, while the genetic capsid modification approach has made feasible the incorporation of peptide and, with some success, small proteins such as single-domain antibodies (~15 kDa) and even single-chain variable fragments (~27 Da) into capsid proteins, the rescuability of the modified viral genomes varies tremendously and needs to be experimentally determined. On the other hand, there has been no report yet on the use of the virus adapter strategy to add functionalities to rare human or nonhuman adenoviral vectors, largely due to the unavailability of viral serotype-specific capsid binders. In these regards, it was demonstrated herein that SpT-incorporated viral vectors as well as the SpC fusion protein could be produced and functionally validated before assembly, and an "off-the-shelf" mixing of the two components under physiological conditions led to a spontaneous titration reaction producing desired adenoviral vectors displaying the macromolecules on the surface. On this basis, it is anticipated that adenoviruses employing this protein-virus conjugation system will readily provide a versatile plug-and-play macromolecule display platform for broader applications including development of targeted delivery systems, adenoviral vectors with shielding against neutralizing antibodies, and protein-based vaccines.

Efficient Gene Editing in Cells Infected with SpT SAd36 Vectors Carrying Cas9SpC/gRNA on the Virion Surface The infectivity of SAd36, SAd36.FFSpT, and SAd36.HSpT to mAi9 cells was defined using a fixed $1.6 \times 10^4$ viral particle to cell (VP/C) ratio based on expression of viral green fluorescent protein (GFP) reporter gene driven by the major immediate-early promoter/enhancer of human cytomegalovirus (CMV).

Figure 13:
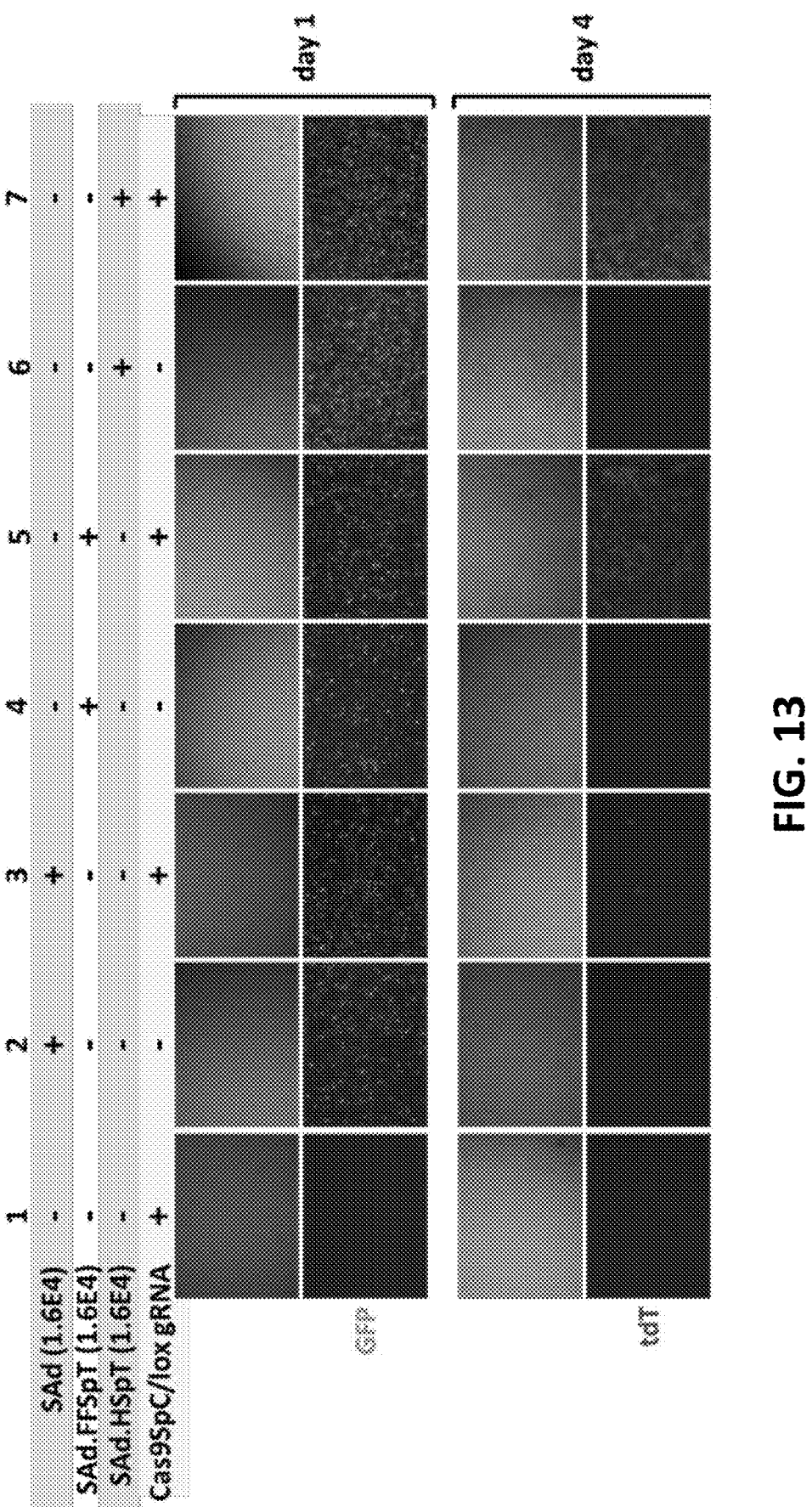
FIG. 13 is an exemplary embodiment showing efficient gene editing in cells infected with SpT SAd36 vectors carrying Cas9SpC/gRNA on capsid surface in accordance with the present disclosure. $2 \times 10^5$ mAi9 cells were incubated with SAd36, SAd36.FFSpT, and SAd36.HSpT at 1.6E4 viral particle per cell (VP/C) ratio (columns 2, 4, and 6). In parallel, the three viruses were also mixed with 7.5 pmol Cas9SpC/lox gRNA at 21° C. for 2 hours before application to mAi9 cell culture medium (columns 3, 5, and 7). Virus infectivity was reported by fluorescence microscopy analysis of GFP-positive cells on day 1 post virus infection. Gene editing events were reported 4 days later by fluorescence microscopy analysis of tdTomato-positive cells. The bright-field imaging confirmed that the cells grew into confluence at the time of tdTomato expression analysis. tdT: tdTomato.

Compared with 25% GFP$^+$ cells by the SAd36 on day 1 post infection, FFSpT virus produced slightly reduced 17% GFP$^+$ cells, and HSpT virus yielded a noticeable increase in GFP$^+$ cells to 33% (see e.g., FIG. 13, columns 2, 4, 6, GFP). These results indicated that the fiber knob domain played a minor role in shaping the SAd36 infectivity of mAi9 cells, and the molecular basis for the increased infectivity of the hexon-modified virus remains to be defined. All three viruses were also incubated with Cas9SpC for 2 h followed by addition of equal moles of lox gRNA, and the resultant reaction mixtures retained the infection levels of all three viruses without Cas9SpC/lox gRNA (see e.g., FIG. 13, 3 versus 2, 5 versus 4, and 7 versus 6, GFP). Importantly, these results suggested that the negatively charged Cas9SpC/lox gRNA complex conjugated on the virion surface affected little with respect to its infection of mAi9 cells.

Figures 14A, 14B:
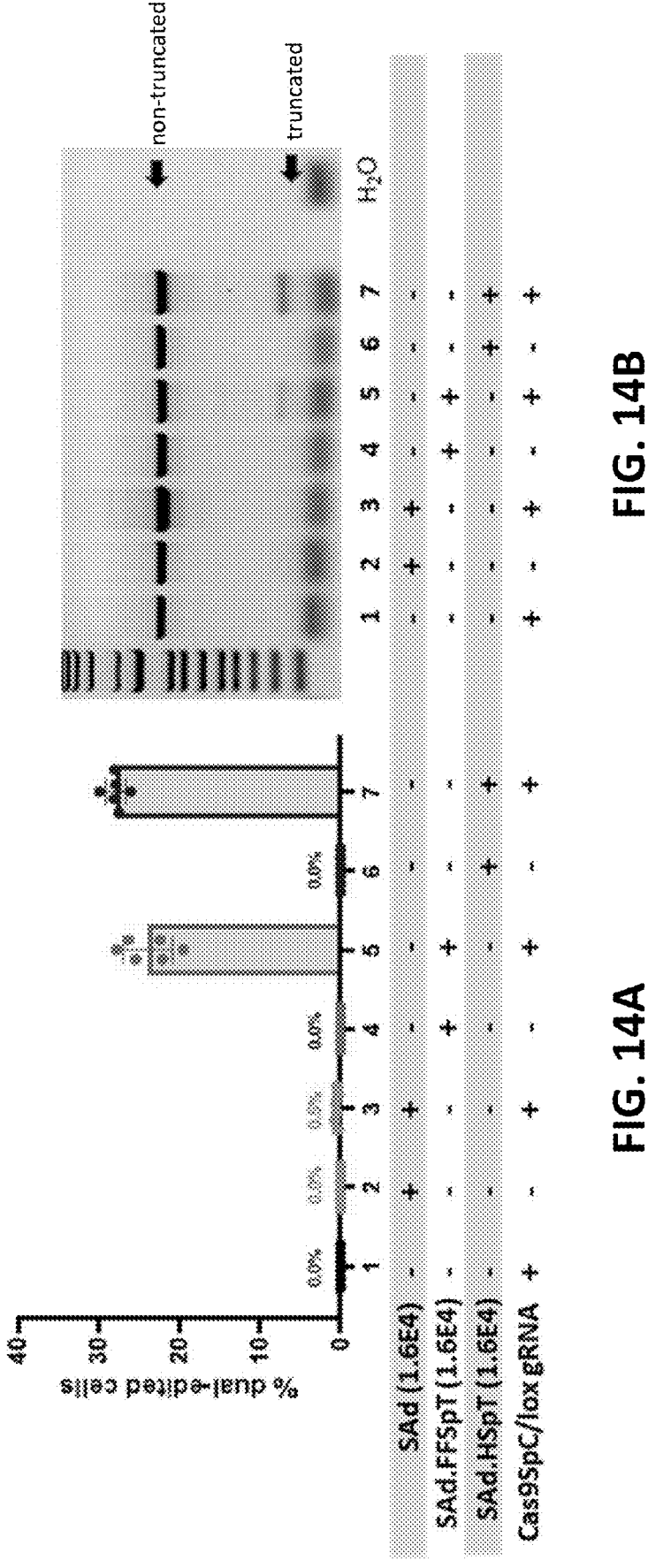
FIG. 14A-FIG. 14B is an exemplary embodiment showing efficient gene editing in cells infected with SpT SAd36 vectors carrying Cas9SpC/gRNA on capsid proteins in accordance with the present disclosure.
Figure 15:
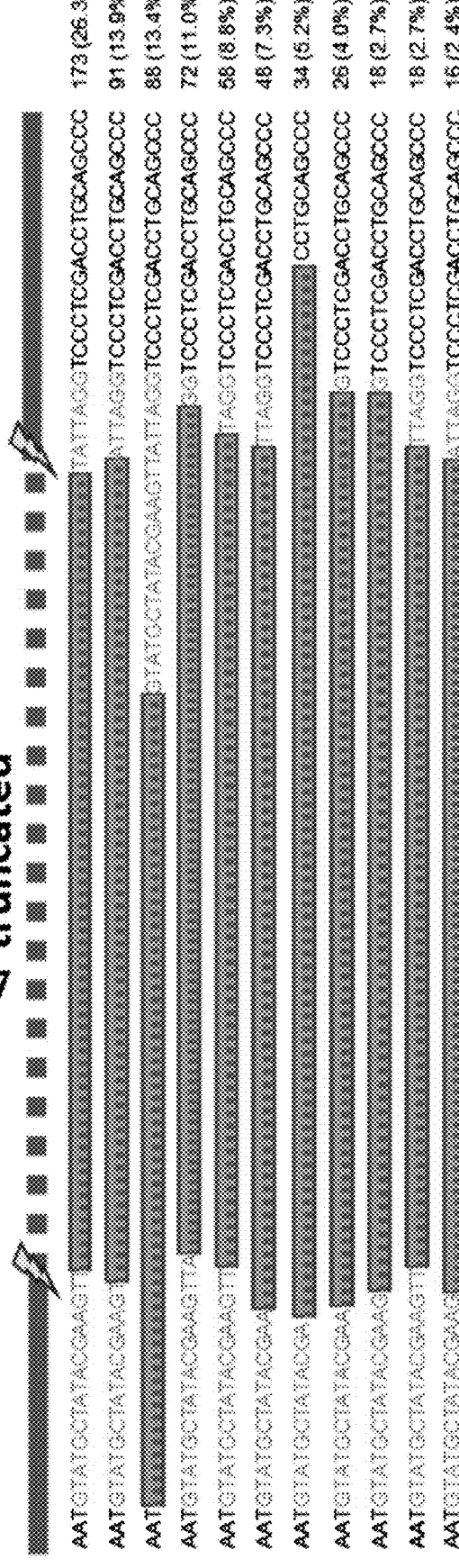
FIG. 15 is an exemplary embodiment showing characteristic SpCas9 nuclease-mediated indel patterns repaired by non-homologous end joining at two lox gRNA sites of Rosa26-tdTomato locus in accordance with the present disclosure.
Figure 16:
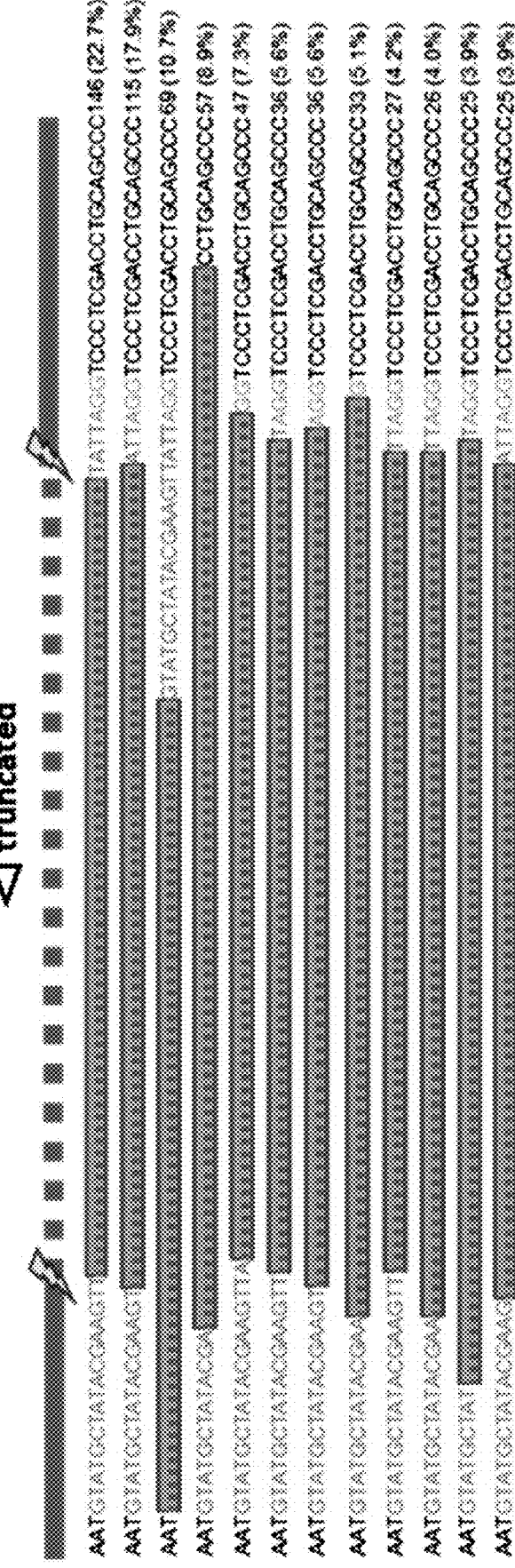
FIG. 16 is an exemplary embodiment showing efficient gene editing in cells infected with SpT SAd36 vectors carrying Cas9SpC/gRNA on capsid proteins in accordance with the present disclosure.
Figure 17:
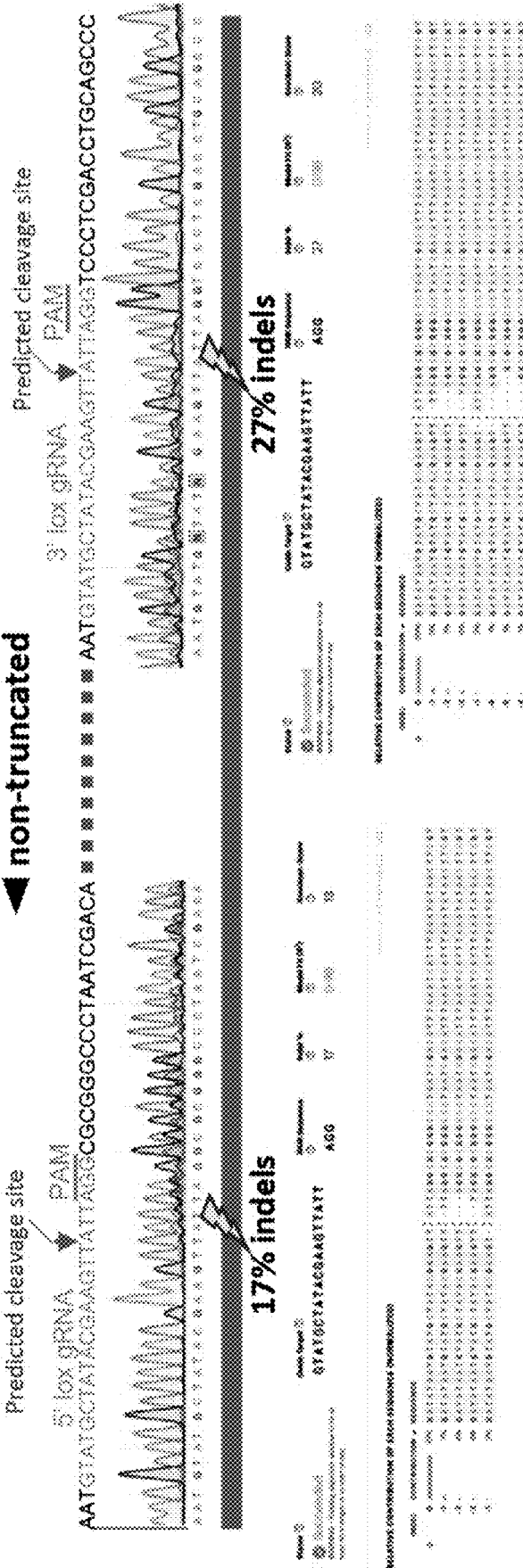
FIG. 17 is an exemplary embodiment showing characteristic SpCas9 nuclease-mediated indel patterns repaired by non-homologous end joining at two lox gRNA sites of Rosa26-tdTomato locus in accordance with the present disclosure.
Figure 18:
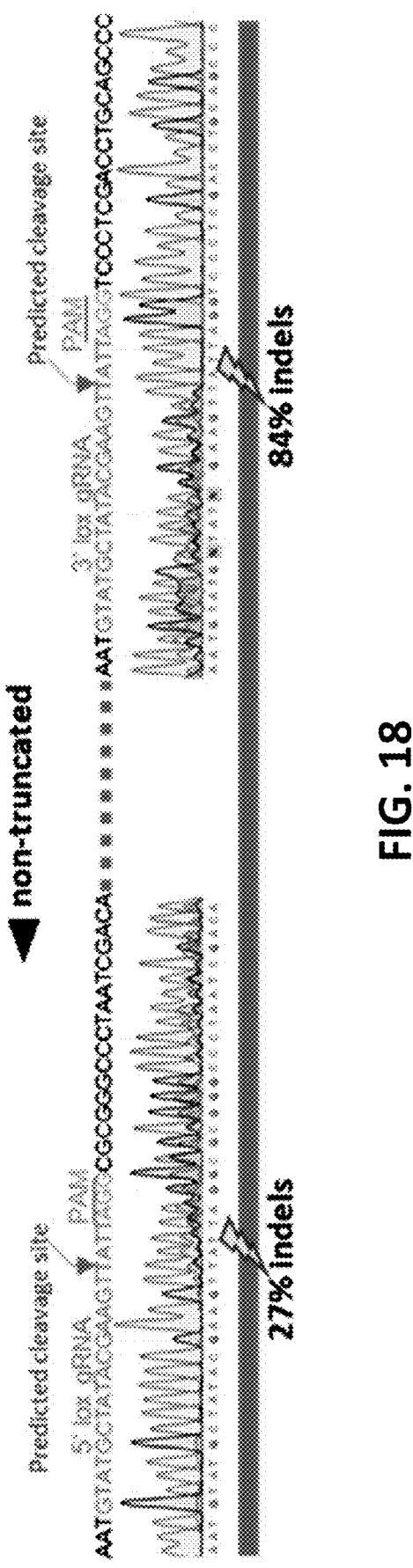
FIG. 18 is an exemplary embodiment showing efficient gene editing in cells infected with SpT SAd36 vectors carrying Cas9SpC/gRNA on capsid proteins in accordance with the present disclosure.
Figure 19:
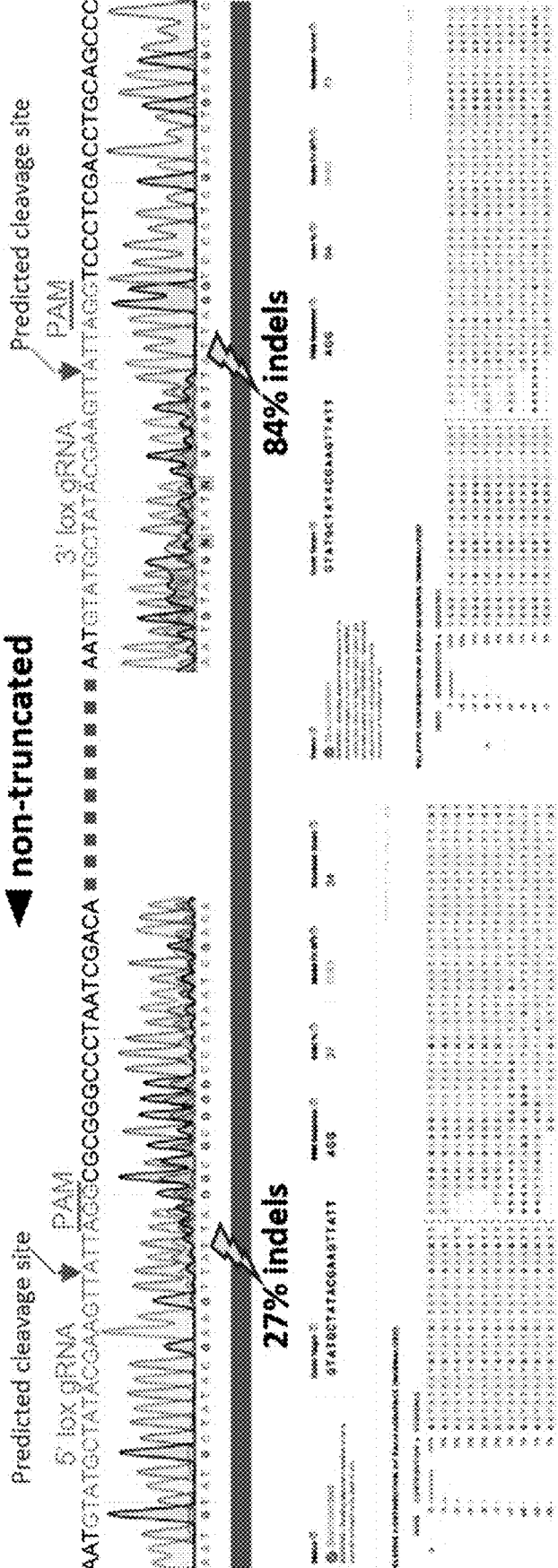
FIG. 19 is an exemplary embodiment showing characteristic SpCas9 nuclease-mediated indel patterns repaired by non-homologous end joining at two lox gRNA sites of Rosa26-tdTomato locus in accordance with the present disclosure.
Figures 20, 21A:
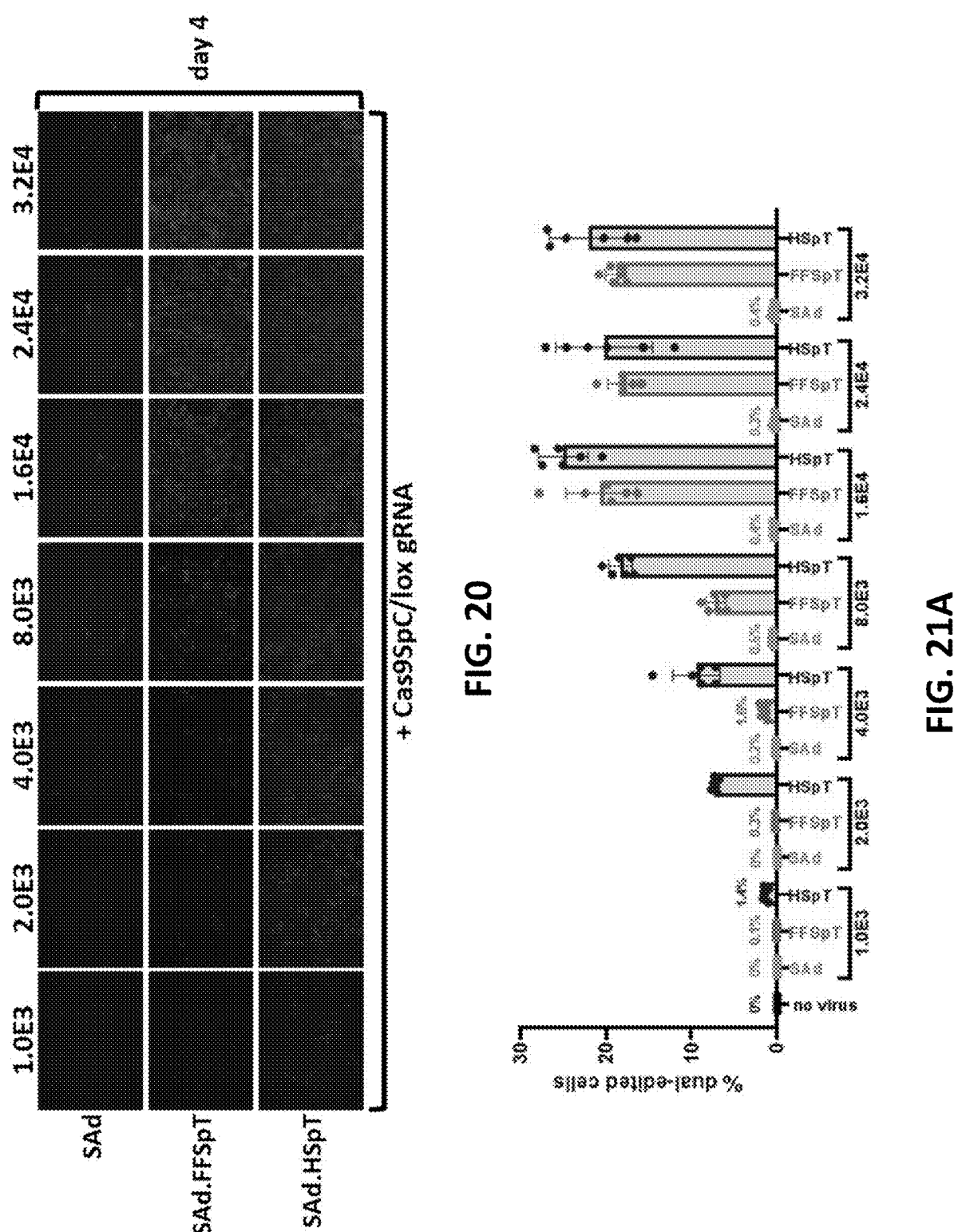
FIG. 20 is an exemplary embodiment showing efficient gene editing in cells infected with SpT SAd36 vectors carrying Cas9SpC/gRNA on capsid surface in accordance with the present disclosure. $2 \times 10^5$ mAi9 cells were incubated with varying amounts of SAd36, SAd36.FFSpT, and SAd36.HSpT in the presence of 7.5 pmol Cas9SpC/lox gRNA. Gene editing events were reported 4 days later by fluorescence microscopy analysis of TdTomato-positive cells. The VP/C ratios are provided on top of micrographs.
FIG. 21A-FIG. 21C is an exemplary embodiment showing viral dose and cell confluence level-dependent gene editing delivered by SpT SAd36 vectors carrying Cas9SpC/gRNA in accordance with the present disclosure.
Figure 21B:
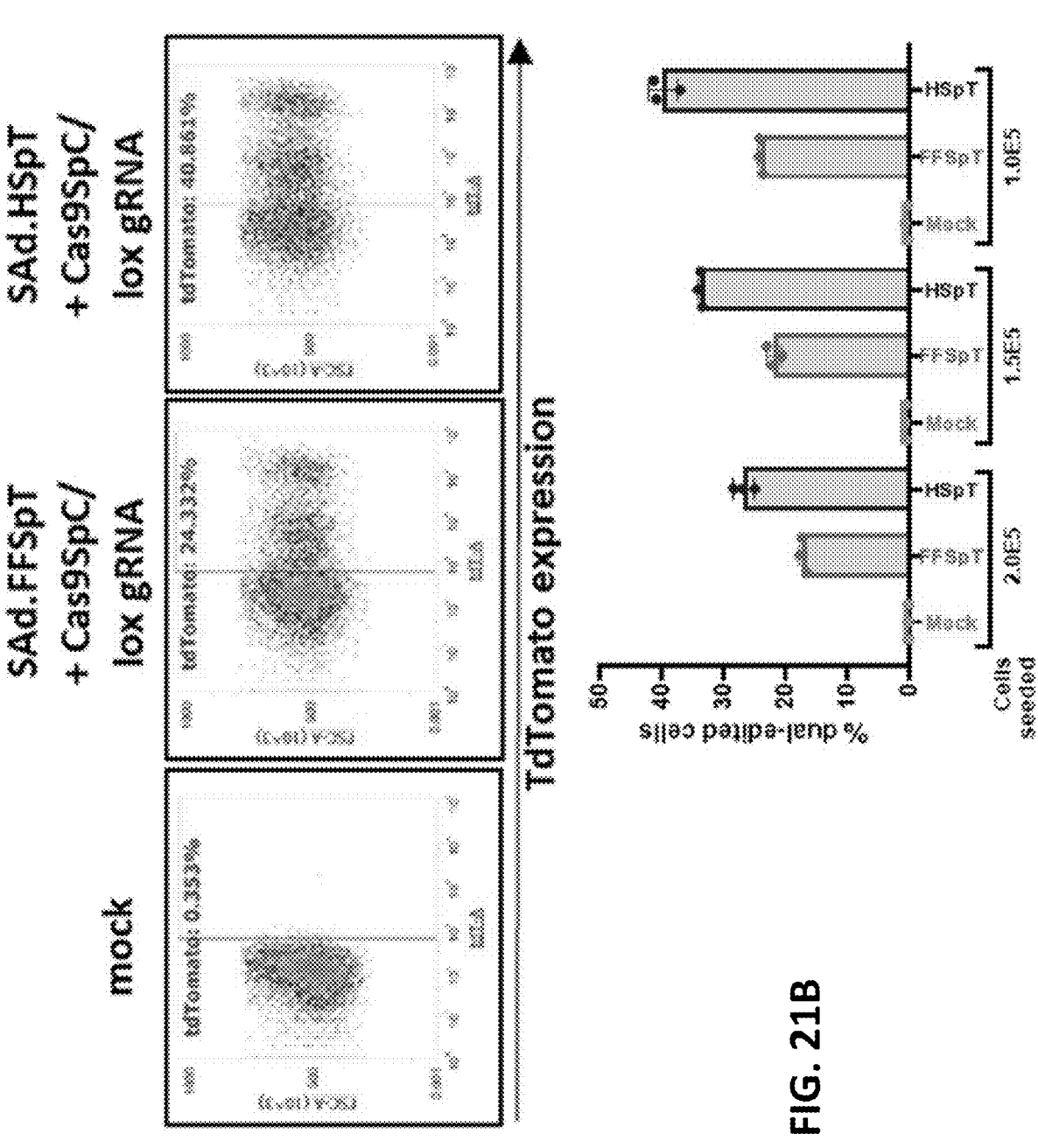
Figure 21C:
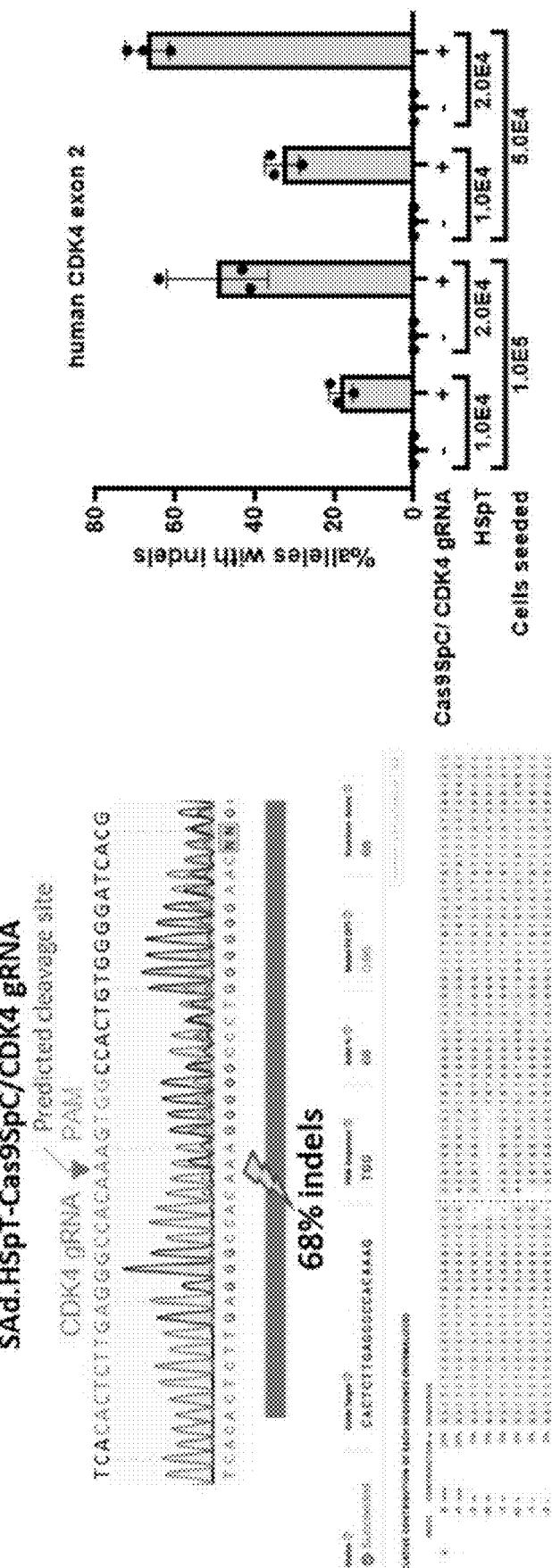

Next, it was determined whether the viral "piggyback" mechanism had the capacity of inducing genome editing in infected cells. First, the possibility that Cas9SpC/lox gRNA, alone or when added to cell culture medium, could produce any detectable gene editing at the Rosa26-tdTomato locus in mAi9 cells was ruled out (see e.g., FIG. 13, column 1-tdT and FIG. 14A, bar 1). Further, it was shown that infection of SAd36, SAd36.FFSpT, or SAd36.HSpT did not yield any detectable gene-editing events (see e.g., FIG. 13, columns 2, 4, and 6, tdT, and FIG. 14A, bars 2, 4, and 6). In contrast, premixing of SAd36.FFSpT or SAd36.HSpT with Cas9SpC/lox gRNA produced efficient gene editing at the Rosa26-tdTomato locus, leading to 23.9%±3.1% and 27.9%±1.3% dual-edited cells, respectively (see e.g., FIG. 13, columns 5 and 7, tdT and FIG. 14A, bars 5 and 7). Intriguingly, a very low yet highly reproducible 0.5%±0.1% dual-gene-editing level was detected in cells treated with the SAd36 and Cas9SpC/gRNA mixture (see e.g., FIG. 13, column 3-tdT, and FIG. 14A, bar 3), implying that, while mAi9 cells did not take up naked Cas9SpC/lox gRNA, uptake of SAd36 by the cells triggered a low-level codelivery of the RNP complex by an undefined mechanism. Next, a PCR genotyping analysis of the Rosa26-tdTomato locus (see e.g., FIG. 5, primers F and R) with genomic DNA derived from cells analyzed in FIG. 14A amplified a predicted nontruncated fragment in all samples (see e.g., FIG. 14B, all lanes, solid arrowhead). In addition, the assay detected truncated fragments in the two samples from cells infected with SAd36.FFSpT-Cas9SpC/lox gRNA and with SAd36.HSpT-Cas9SpC/lox gRNA (see e.g., FIG. 14B, lanes 5 and 7, truncated row). Next-generation DNA sequencing analysis of the truncated bands from the two groups confirmed Cas9-mediated double-stranded DNA cleavage at both lox gRNA sites resulting in deletion of the STOP cassette (see e.g., FIG. 15, SAd.FFSpT-Cas9SpC/lox gRNA, and FIG. 16, SAd.HSpT-Cas9SpC/lox gRNA). Furthermore, Sanger sequencing of the nontruncated band was performed followed by inference of CRISPR edits (ICE) analysis to measure the level of Cas9-induced DNA double-strand breaks repaired by nonhomologous end joining (NHEJ). Cells infected with SAd36.FFSpTCas9SpC/lox gRNA exhibited 17% and 27% small insertion/deletion (indel)-type Cas9 editing at the upstream and downstream lox RNA sites from all nontruncated alleles, respectively (see e.g., FIG. 17), while cells infected with SAd36.HSpT-Cas9SpC/lox gRNA showed 27% and 84% editing at the two sites (see e.g., FIG. 18 and FIG. 19). Taken together, the combined results from FIG. 16 and FIG. 18 suggested that cells infected with SAd36.FFSpT-Cas9SpC/lox gRNA exhibited 37% editing of all alleles at upstream and 45% at downstream lox RNA recognition sites, and cells infected with SAd36.HSpTCas9SpC/lox gRNA exhibited 47% editing of all alleles at upstream and 89% at downstream lox RNA recognition sites. Next, the virus dose response by varying the VP/C ratio to cells seeded at $2.0 \times 10^5$ per well in a 24-well format revealed superior gene-editing activity by SAd36.HSpT-Cas9SpC/lox gRNA over SAd36.FFSpT-Cas9SpC/lox gRNA at lower VP/C ratios (see e.g., FIG. 20 and FIG. 21A, FFSpT and HSpT/1.0-8.0×10³ VP/C). Thus, HSpT virus at a VP/C ratio of $8.0 \times 10^3$ attained an 18.4%±1.4% dual-editing level versus 7.2%±1.4% by the FFSpT equivalent. Both FFSpT and HpT viruses, however, reached a plateau of gene editing efficiency at VP/C ratios higher than $1.6 \times 10^4$ (see e.g., FIG. 20 and FIG. 21A, FFSpT and HSpT/$2.4 \times 10^4$ and $3.6 \times 10^4$ VP/C), implying that, at high VP/C ratios, nuclear entry of FFSpT-Cas9SpC/gRNA was almost as effective as HSpT-Cas9SpC/gRNA, although the FFSpT virus contained about 10 times less Cas9SpC than the HSpT virus. It was further shown that the capacity of the viral "piggyback" genome editing was also sensitive to the cell confluence level with cells seeded at $1.0 \times 10^5$ per well in a 24-well format supporting the most efficient gene editing by both SpT SAd36 vectors carrying Cas9SpC/lox gRNA. In this regard, FFSpT and HSpT viruses at $1.6 \times 10^4$ VP/C ratio produced 24.1%±0.4% and 39.7%±2.3% dual-editing, respectively, on day 4 following virus infection (see e.g., FIG. 21B, right panel, cells seeded: $1.0 \times 10^5$ per well). The effects of viral dose and seeding cell density on gene-editing efficiency by SAd36.HSpT-Cas9SpC at the CDK4 locus in human lung adenocarcinoma A549 cells were further investigated. A superior editing efficiency of 67.0%±5.6% (indels) of all CDK4 alleles was attained in cells seeded at $5.0 \times 10^4$ per well in a 24-well format and infected with SAd36.HSpT-Cas9SpC/CDK4 gRNA at a $2.0 \times 10^4$ VP/C ratio (see e.g., FIG. 21C). Taken together, these data fully validated the feasibility of achieving efficient gene editing by the adenoviral "piggyback" delivery route of the editor machinery in both murine and human cells.

To gain a mechanistic understanding of the adenoviral "piggyback" transport of the Cas9/gRNA complex, the fate of Cas9SpC conjugated on SpT viruses following infection of mAi9 cells was studied next. A tdTomato-specific gRNA instead of the lox gRNA was used in the following assays to allow the proper intranuclear localization of Cas9SpC/gRNA complex yet avoid the activation of tdTomato gene expression.

Figure 22A:
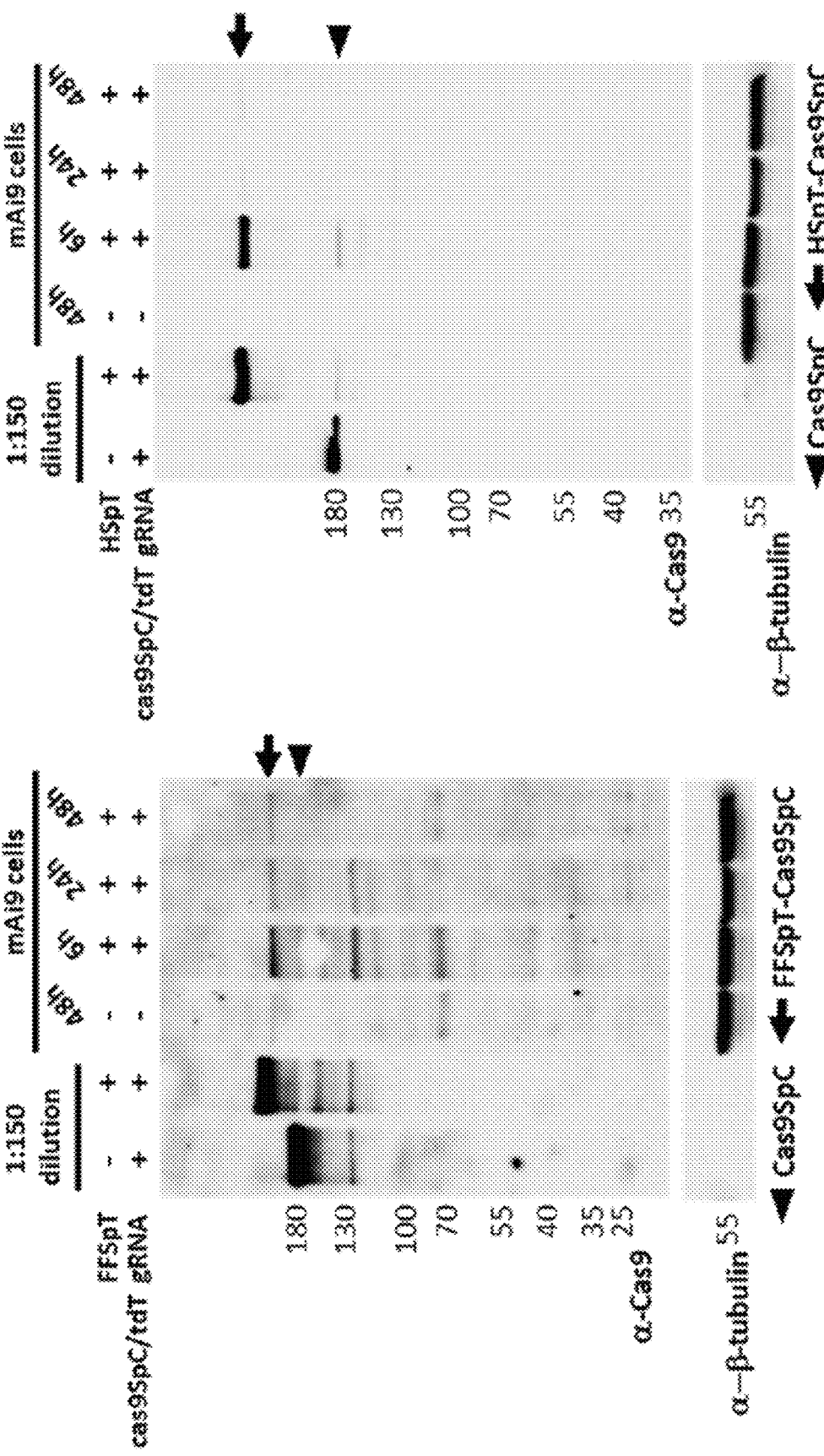
FIG. 22A-FIG. 22C is an exemplary embodiment showing intracellular delivery of conjugated "piggyback" Cas9SpC by SpT SAd36 viruses in accordance with the present disclosure.
Figures 22B, 22C:
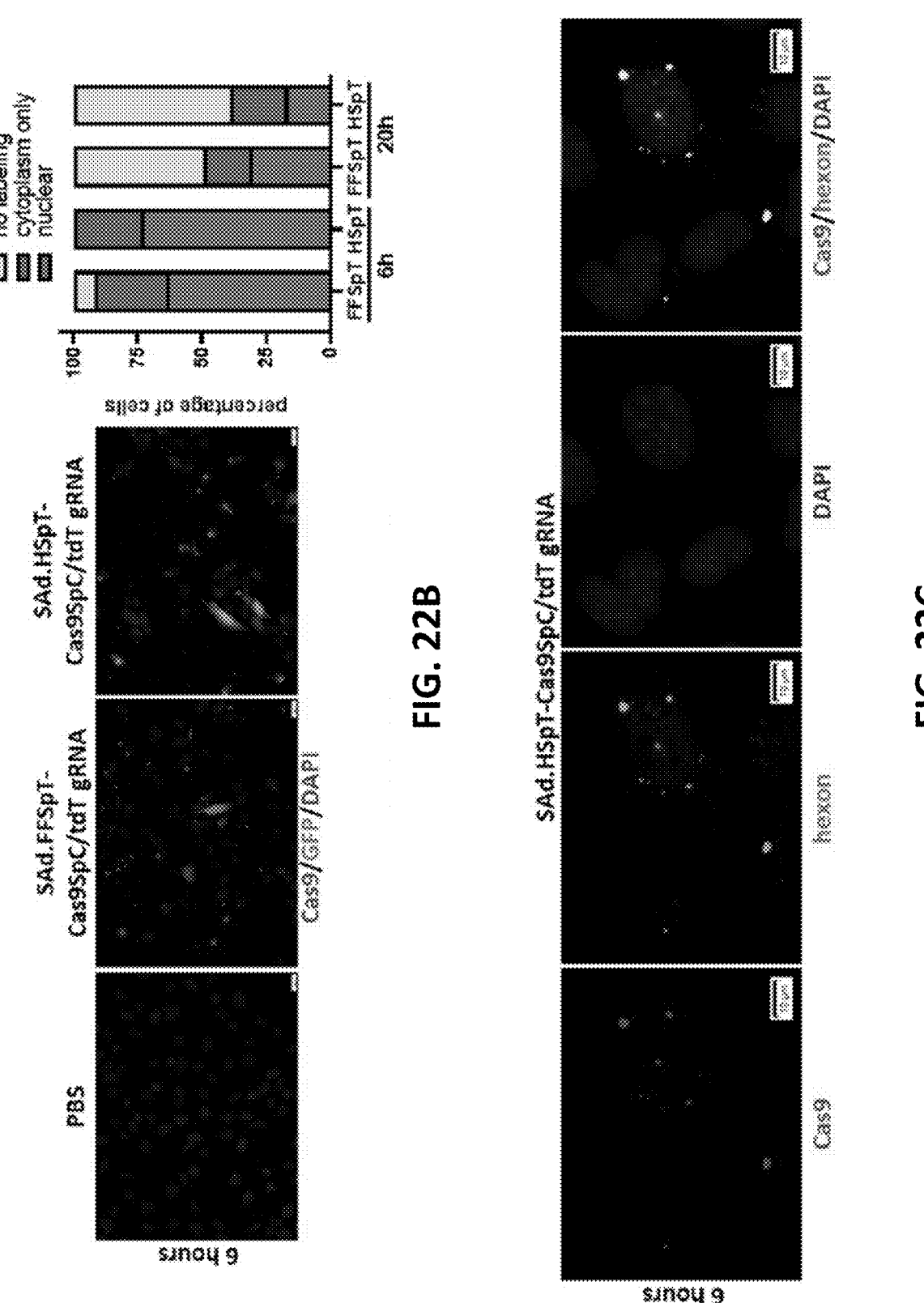
Figure 23A:
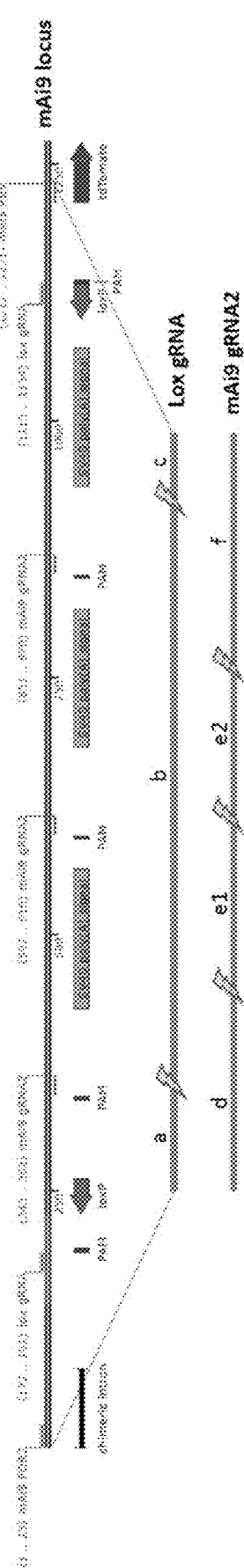
FIG. 23A-FIG. 23C is an exemplary embodiment showing Cas9SpC conjugated on SpT SAd36 virion surface retained CRISPR nuclease activity in an in vitro DNA cleavage assay in accordance with the present disclosure.
Figures 23B, 23C:
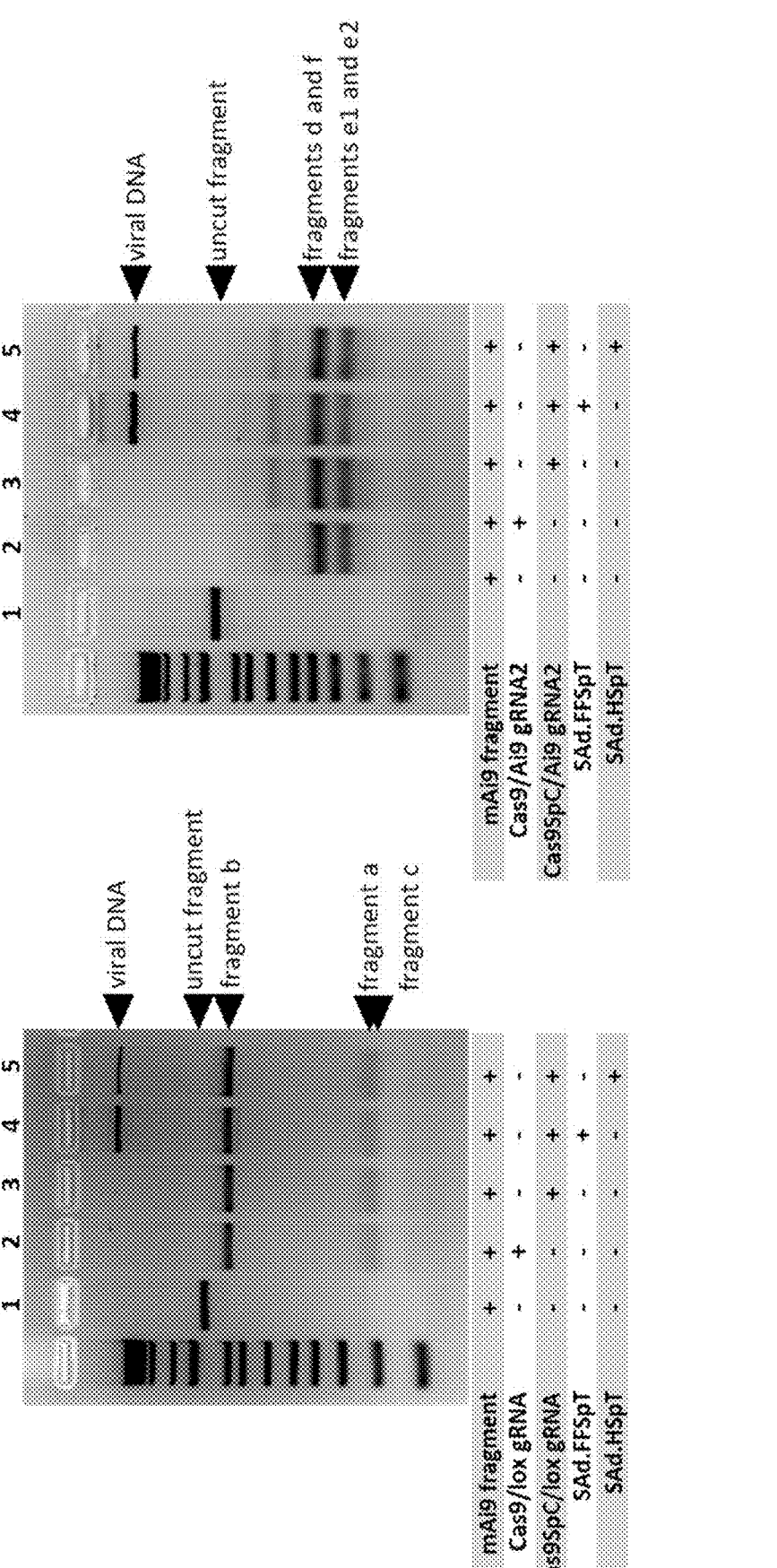

Immunoblot analysis with the SpCas9-specific antibody revealed abundant FFSpT-Cas9SpC (219.1 kDa) and HSpT-Cas9SpC (288.7 kDa) conjugates in cells at 6 h post infection with SAd36.FFSpT-Cas9SpC/tdT gRNA or SAd36.HSpTCas9SpC/tdT gRNA (see e.g., FIG. 22A-FIG. 22B, 6 h, arrows). The cellular levels of capsid-Cas9SpC conjugates reduced markedly by 24 h post infection but remained slightly above the detection threshold by 48 h post infection (see e.g., FIG. 22A-FIG. 22B, 24 h and 48 h, arrows). Immunofluorescence (IF) microscopy analysis revealed Cas9 staining in a majority of cells at 6 h post virus infection with greater than half of all assayed cells possessing nuclear Cas9 signals and a small portion of cells containing cytoplasm-only Cas9 presence (see e.g., FIG. 22B). In addition, the reactivity of a goat polyclonal antibody was validated against human adenovirus 5 hexon to the SAd36 equivalent by IF studies (data not shown). Consistent with the immunoblot results, costaining of cells at 6 h post virus infection with Cas9 and SAd36 hexon antibodies showed a striking colocalization of the two protein moieties within infected cells (see e.g., FIG. 22C). Together, these data raised the possibility that nuclear FFSpT-Cas9SpC/gRNA and HSpTCas9SpC/gRNA may retain the CRISPR nuclease activity that was responsible for gene editing in infected cells. Consistent with this notion, an in vitro DNA cleavage assay was performed on a PCR-generated Rosa26-tdTomato fragment using Cas9SpC/gRNA conjugated on both SpT viruses as shown in FIG. 22A (lane 2 of both immunoblot panels). The free Cas9SpC and two-capsid-linked Cas9SpC with the lox gRNA as well as with a second mAi9 gRNA (gRNA2) robustly cleaved the fragment to completion when compared with the free Cas9 (see e.g., FIG. 23A-FIG. 23C), suggesting that Cas9 in fusion with SpC (i.e., Cas9SpC) or Cas9SpC conjugated on SpT virus capsids did not affect nuclease activity when compared with free Cas9.

A salient finding of the present study was the utility of the adenoviral capsid conjugate approach to deliver an intracellularly acting macromolecule, the cas9/gRNA RNP complex. Till now, a number of attempts have been made to achieve intracellular delivery of protein and RNP biologics to human cells using nonviral carriers such as cationic liposomes, cell-penetrating peptide incorporation, anionic polymers, and nanocapsule polymers. A major limiting factor is presently the lack of a defined in vivo targeted delivery mechanism to arm these systems, which is the focus of current research. Unlike the emerging nonviral approaches, adenovirus is one of the commonly utilized gene therapy platforms due to the availability of a collection of vectors with diverse tissue tropism across a variety of disorders. As detailed in the introduction section, additional advantages have made the adenoviral vector an ideal exogenous protein and RNP delivery platform. Interestingly, adenovirus possesses a very efficient nuclear entry mechanism for viral DNA as well as capsid proteins. The data are consistent with the notion that the NLS-loaded gene editor conjugated on the adenoviral fiber or hexon can efficiently gain access to the host cell nuclear compartment and function normally as a gRNA sequence-mediated DNA endonuclease on chromatin DNA, revealing compatibility of the conjugated capsid proteins to subnuclear localization of NLS-Cas9 nuclease. However, to generalize the utility of the viral delivery platform for other cellular biologics, it is potentially important to provide a releasable function to the protein cargo moiety from the capsid conjugate within the cytoplasm or inside the nucleus. In this regard, the use of an integral viral protease-cleavable linker and intracellular biodegradable cross-linking scheme has been reported to attain the intracellular release of a protein cargo from its conjugate. Notably, as an integral core protein within mature adenoviral particles, adenovirus L3 protease (AVP) activity is believed to play a critical role in facilitating a series of viral capsid uncoating events in the endosome and cytoplasm. As such, an attractive hypothesis warranting further research is the introduction of an AVP preferential cleavage site at the linker between the protein cargo and SpC to facilitate the release of protein cargo in the cytoplasm.

An intriguing aspect of the adenoviral Cas9/gRNA RNP delivery is related to the question of whether a similar efficient RNP delivery can be achieved with viral particles composed of empty capsids without viral DNA in a potential adenoviral-like particle platform. In this regard, adenovirus assembly follows a sequential pathway in which the formation of empty capsids containing the major and minor capsid proteins and some core components such as AVP protease precedes genome packaging into the empty capsids to form mature full virions. The DNA-free empty capsids with a lower density are readily detectable and separable from the heavier full virions during a routine virus purification procedure. The hypothesis that the SpT-incorporated empty capsids may possess the full capacity of gene editor cargo conjugation and delivery to the reporter cells is currently under investigation.

Conclusion

The development of a plug-and-play adenoviral platform that can piggyback transport Cas9/gRNA complex on viral capsid surface into the nucleus of target cells is described herein, leading to robust genome editing. This viral intracellular delivery system works via a spontaneous titration reaction between the off-the-shelf engineered virus and a prevalidated Cas9/gRNA complex exploiting SpyTag003/Spycatcher003 coupling chemistry under physiological conditions. The resultant Cas9/gRNA-conjugated virus was employed directly to achieve robust gene editing in target cells. As such, the repurposed utility of a clinically relevant adenoviral vector establishes the technical basis for a range of interventional possibilities.

Materials and Methods

Materials

TrueCut Cas9 V2 was purchased from ThermoFisher Scientific. SpyCatcher003 and SpyTag003-MBP proteins were acquired from Kerafast, Inc. Lox sgRNA targets the DNA sequence 5'-GTATGCTATACGAAGTTATT-3' (SEQ ID NO: 1). mAi9 sgRNA2 targets 5'-AAGTAAAACCTC-TACAAATG-3' (SEQ ID NO: 2). The tdTomato gene knockout sgRNA recognizes 5'-GGC-CACGAGTTCGAGATCGA-3' (SEQ ID NO: 3). Human CD4 exon 2 sgRNA recognizes 5'-CACTCTTGAGGGC-CACAAAG-3' (SEQ ID NO: 4). The Cas9 sgRNAs were custom-synthesized using TrueGuide synthetic CRISPR gRNA technology with chemical modifications including 2'-O-methyl analogs and phosphorothioate linkages which increase editing efficiency and protect against nuclease degradation. Modified Ai9 (Ai9-SauSpyCas9 or mAi9) mouse embryonic fibroblasts were acquired from Baylor University.

Cas9SpC Cloning and Expression

The plasmid pET-21a_3× NLS_SpCas9_protein_expression was a gift (Addgene plasmid #114365; RRID:Addgene_114365). The SpCas9 cassette is armed with three nuclear localization signals and contains at its 5'-end the T7 phage gene 10 leader sequence that enhances translation of foreign mRNAs in E. coli. A digestion of pET-21a_3×NLS_SpCas9 plasmid with XhoI and DraIII released a 6×His tag-containing fragment. A 856 bp fragment with a TEV protease recognition site, Spy-Catcher003, and 6×His was synthesized and ligated via Gibson assembly to the XhoI/DraIII-digested pET-21a_3× NLS_SpCas9 backbone to yield the 3×NLS_SpCas9_SpyCatcher003_6×His fusion cassette. The resultant plasmid was introduced into protein expression BL21(DE3) E. coli cells. Single colonies were used to inoculate 100 mL of starter LB containing 100 μg/mL carbenicillin and grown at 37° C. with shaking at 250 rpm until the OD600 of the culture reached 1.9. A. Fresh LB (0.5 L) was inoculated with the starter culture with initial OD600 at 0.01 and was grown at 37° C. with shaking at 250 rpm until the OD600 reached 0.5-0.8. Recombinant protein expression was induced with 0.42 mM isopropyl β-D-1-thiogalactopyranoside (IPTG) in medium, and the cultures were incubated overnight at 21° C. with shaking at 250 rpm. Cultures were centrifuged, and cell pellets were resuspended in lysis buffer (0.5 mM Tris, 0.3 M NaCl, 10 mM imidazole, 0.2% Triton, 1 mg/mL lysozyme, 20 units/mL DNase 1, 1 mM PMSF, and one complete mini EDTA-free protease inhibitor cocktail tablet per 10 mL) and incubated at 37° C. for 30 min. The cell lysates were clarified by centrifugation at 32,000 rcf at 4° C. for 30 min, the 6×Histagged recombinant protein was purified using a HisPur Ni-NTA column with 20 mM imidazole washing buffer and 300 mM imidazole elution buffer, and eluted proteins were dialyzed in 10% glycerol in PBS with three buffer changes using 3.5 KDa molecular weight cutoff Slide-A-Lyzer Dialysis Cassettes. Protein concentration was measured using absorbance at 280 nM with extinction coefficient calculated by SnapGene software.

Construction of Recombinant SpT SAd36 Vectors pC36.000.cmv.PI.EGFP.BGH plasmid carrying the genome of chimpanzee adenovirus SAd36 from species/subgroup E was employed, in which the early E1 region was replaced by a CMV promoter-hybrid intron-eGFP cassette. The E3 region-deleted pC36.000.cmv.PI.EGFP.BGH viral genome was further engineered by removing a 4384 bp fragment from a BspEI site to the E3 14.7K stop codon, which includes seven genes: E3 CR1-α, E3 gp19K, E3 CR1-β, E3CR1-γ, E3 RID α, E3 RID β, and E3 14.7k.35 To engineer SAd36 fiber modification, a pSAd36 fiber shuttle vector was created, in which a 4642 bp fragment from the Swal site to the downstream ITR was cloned into an Amp-resistance plasmid backbone. The fiber knob region (sequences encoding codon 246 to the last codon 425) was replaced by the 285 bp bacteriophage T4 fibritin domain, 45 bp sequence encoding a flexible linker, and sequences encoding SpyTag003 to derive the pSAd36-FFSpT shuttle. The viral genome fragment within the pSad36FFSpT shuttle was released with two engineered restriction enzyme Sacll and Stul sites and ligated back to the rest of the pSAd36 viral backbone scarlessly via Gibson assembly to derive pSAd36.FFSpT. A pSAd36 hexon shuttle vector, in which a 4398 bp Clal-Sbfl fragment was cloned into the Amp-resistance plasmid backbone pre-engineered with adapter sequences containing Clal-Sbfl sites as well as flanking viral sequences, was also created. The hexon hypervariable region 5 (sequences encoding codon 257 to codon 301) was replaced by 48 bp SpyTag003 flanked by 45 bp at the 5' end and 42 bp at 3' sequences encoding flexible linkers to derive the pSAd36-HVR5-45AA-SpyTag shuttle. The viral DNA was released from the shuttle vector with Mlul and Hpal sites and reintroduced back to the rest of the viral genome cut with dual Clal-Sbfl via Gibson assembly to derive the pSAd36.HSpT viral genome. The constructed viral genomes were excised by restriction Pacl digestion and then transfected into 293F28 cells for SAd36.FFSpT or into 293 cells for SAd36.HSpT. The in-house 293F28 system was derived from HEK293 cells engineered to express wild-type Ad5 fiber protein, which was able to trans-complement pSAd36.FFSpT for the lack of wild-type SAd36 fiber function in virus rescue and upscaling. SAd36.FFSpT was subject to a final propagation in unmodified HEK293 cells to obtain viral particles containing only the chimeric FF-targeting peptide. Hexon-modified virus was upscaled with HEK293 cells. Viruses were purified by CsCl gradient centrifugation and dialyzed against 10% glycerol in PBS, and viral particle titer will be quantified by measuring the absorbance of the dissociated virus at 260 nm using a conversion factor of $1.1 \times 10^{12}$ viral particles (vp) per absorbance unit.

SDS-PAGE Coomassie Blue Staining and Immunoblot Analysis

Protein samples were mixed with 0.5 volume of 3×SDS sample buffer (187.5 mM Tris-HCl, pH 6.8, 6% SDS, 30% glycerol and 0.03% bromophenol blue, 0.125 M dithiothreitol) and heated at 97° C. or boiling for 8 min. Protein samples were also treated at room temperature for 8 min as a no-heating control. Treated protein samples were resolved by 4-15% gradient SDS-PAGE using a Criterion electrophoresis system (Bio-Rad), and gels were washed with water briefly and stained with GelCode blue stain reagent (FisherScientific) following the manufacturer's protocol. For immunoblotting, mAi9 cells in a 6-well plate were lysed with 1×RIPA buffer (20 mM Tris-HCl, pH 7.5, 150 mM NaCl, 1 mM Na₂EDTA, 1 mM EGTA, 1% NP-40, 1% sodium deoxycholate, 2.5 mM sodium pyrophosphate, 1 mM β-glycerophosphate, 1 mM Na₃VO4, 1 µg/mL leupeptin, 1 mM PMSF), protein concentration was quantified by the BCA protein assay kit (TheremoFisher), and cells were treated with 0.5 volume of 3×SDS sample buffer (187.5 mM Tris-HCl, pH 6.8, 6% SDS, 30% glycerol and 0.03% bromophenol blue, 0.125 M dithiothreitol) and heated at 97° C. or boiling for 8 min. Protein samples were separated on polyacrylamide gels and transferred to polyvinylidene difluoride (PVDF) membranes. Membranes were blocked in Tris-buffered saline (TBS, pH 7.6) containing 0.5% Tween 20 (TBST) and 5% nonfat dry milk and incubated in 5% BSA in TBST, containing rabbit polyclonal anti-SpCas9 (Cell Signaling Technology, #14697, 1:5,000) and mouse monoclonal anti-6×His (MilliporeSigma, H1029, 1:1,000) antibodies overnight. Membranes were washed three times with TBST and incubated in TBST containing 5% milk with the corresponding IgGhorseradish peroxidase conjugate, 1:5,000 (Santa Cruz Biotechnology and Cell Signaling Technology) for 1 h. After three TBST washes, peroxidase activity was revealed by enhanced chemiluminescence using ECL or ECL2 Western blotting substrate (both from Thermo Scientific) and imaged using a Chemidoc XRS imaging system (Bio-Rad Laboratories, Hercules, CA).

Conjugation of SpT and SpC

To conjugate SpT maltose-binding protein fusion protein with SpC, the two components at amounts designated in each figure were incubated in a standard phosphate-buffered saline (PBS) buffer at 21 or 37° C. for 1-2 h before the reaction content was subject to protein composition analysis by SDS-PAGE. To conjugate SpT-incorporated adenoviruses with SpC or with Cas9SpC/gRNA, viruses and SpC or Cas9SpC were incubated in PBS containing 10% glycerol at 21 or 37° C. for 2 h. Lox sgRNA at designated amounts was added to the reaction content, and the mixture was incubated at 21° C. for 10-15 min before application to cell culture medium or subject to protein composition analysis by SDS-PAGE.

CRISPR-Cas9 Gene-Editing Assay with mAi9 and A549 Cells.

For lipofectamine CRISPRMAX transfection of mAi9 cells, $1.0 \times 10^5$ cells were seeded in individual wells of a 24-well plate, and 16 h later, the cells were transfected using Lipofectamine CRISPRMAX according to the manufacturer's protocol. The amounts of TrueCut Cas9 v2 or Cas9SpC and lox gRNA are designated in FIG. 7B. For adenovirus transduction of mAi9 and A549 cells, $0.5 \times 10^4$ to $2.0 \times 10^5$ cells (designated in each experiment) were seeded in individual wells of a 24-well plate, and 18 h later, the cell culture was replaced with fresh medium containing various amounts of viruses premixed with or without 7.5 pmol of Cas9SpC/gRNA. CRISPR-Cas9 gene editing analyses were carried out in mAi9 cell cultures 4 days post transfection or virus transduction and in A549 cells 48 h post virus infection.

Immunofluorescence, Fluorescence Microscopy, and Flow Cytometry Analysis

For immunofluorescence staining, $2\times10^4$ mAi9 cells were seeded in Nunc Lab-Tek II 8-well chamber slides (ThermoFisher) and, 16 h later, were infected with SpT viruses conjugated with Cas9SpC/tdT gRNA, fixed in 4% paraformaldehyde for 30 min and then at 4° C. in protein block (5% donkey serum in PBS) containing primary antibodies overnight or longer. Primary antibodies used in this study included mouse anti-SpCas9 (Cell Signaling Technology, #14697, 1:400) and goat anti-Ad5 hexon. On day 2, the slides were washed three times in PBS, incubated with corresponding 1:400 diluted Alexa Fluor594- and Fluor647-conjugated secondary antibodies (Jackson ImmunoResearch Laboratories), and counterstained with SlowFade Gold Antifade mounting reagent with 4,6-diamidino-2 phenylindole (DAPI) (Thermo Fisher Scientific). White-light, fluorescence, and immunofluorescence microscope images were collected using an Olympus DP71 color microscope digital camera (Olympus America). The optimized camera acquisition time for tdTomato fluorescence was set a priori using cells without tdTomato expression in each experiment. The percentage of tdTomato-positive areas was quantified with CellSens Dimension imaging software (Olympus). A threshold defining the background signal intensity was set using micrographs collected from untreated mAi9 cells, and pixels with above the background red color intensity were identified and summed. The percentage of tdTomato-positive area to total micrograph area was calculated. The tdTomato expression in mAi9 cells was also analyzed by flow cytometry. Adherent mAi9 cells were detached into a single cell suspension by trypsin/EDTA and analyzed directly without fixation by an Attune NxT flow cytometer using a YL-1 laser (ThermoFisher).

Genomic DNA PCR and Sequencing Analysis of mAi9 Rosa26-tdTomato and Human CDK4 Loci Adherent mAi9 and A549 cells in individual wells of a 24-well plate were covered with 0.5 mL of lysis buffer (100 mM Tris-HCl, pH 8.5, 0.2% SDS, 5 mM EDTA, 200 mM NaCl, and 100 ug/mL proteinase K) and incubated at 55° C. for 4 h. The cell lysates were extracted once with equal volumes of phenol/chloroform/iso-amyl alcohol, pH 8.0, and then with chloroform, and DNA was precipitated with ethanol in the presence of sodium acetate. Dual-gene editing at the ROSA26-tdTomato locus was detected by PCR amplification of a fragment spanning the two loxP sites with the upper stream primer 5'-GCAACGTGCTGGTTATTGTG-3' (SEQ ID NO: 5) and downstream primer 5'-CTCAC-CATGGTGGCGGGATC-3' (SEQ ID NO: 6). PCR amplification yielded a 1137 bp fragment for the unedited sequence and approximately averaged truncated 194 bp fragments from the dual-edited allele with STOP cassette deletion. The truncated DNA bands were retrieved and submitted for next-generation sequencing by Genome Engineering & iPSC Center of Washington University School of Medicine. The human CDK4 exon region was amplified by PCR using the upper stream primer 5'-GCCGGCCC-CAAGGAAGACTGGGAG-3' (SEQ ID NO: 7) and downstream primer 5'-GCACAGACGTCCATCAGCC-3' (SEQ ID NO: 8). The nontruncated at ROSA26-tdTomato and CDK4 DNA bands were subject to Sanger sequencing. The inference of CRISPR editing (ICE) analysis, which is superior to TIDE analysis, was performed using the ICE calculator tool developed by the genome engineering company Synthego.

Transmission Electron Microscopy Analysis of Adenovirus Vectors

Adenovirus samples were diluted to a concentration of $1.0\times10^{10}$ vp/ml in PBS, absorbed onto freshly glow discharged formvar/carbon-coated copper electron microscopy grids for 10 minutes, then floated in a drop of fixative (1.25% glutaraldehyde/2% paraformaldehyde in PBS) for 30 minutes, washed with deionized water, and negatively stained with 1% uranyl acetate. Images were taken at 30,000× and 75,000× magnifications using a JEOL 1200EX transmission electron microscope (JEOL USA, Peabody, MA) equipped with an AMT 8 megapixel digital camera (Advanced Microscopy Techniques, Woburn, MA). Sample processing and imaging were carried out by Molecular Microbiology Imaging Facility of Washington University School of Medicine in St Louis.

In Vitro Cas9 DNA Cleavage Assay

A 1231 bp Rosa26-tdTomato DNA fragment was amplified using genomic DNA derived from mAi9 cells by PCR with primers shown in Supplemental FIG. 8B. Within this fragment, DNA sequences that are recognized by lox gRNA and by mAi9 gRNA2 are shown in TABLE 1.

TABLE 1

Sequences of PCR primers, lox gRNA/PAM, and mAi9 gRNA2/PAM.

| Primers for mAi9 locus PCR amplification | |
| --- | --- |
| mAi9 FOR2 | mAi9 ReV |
| 5'-GGTTCGGCTTCTGGCGTGTGACC-3' (SEQ ID NO: 9) | 5'-CTCGCCCTTGCTCACCATGG-3' (SEQ ID NO: 10) |

| mAi9 gRNAs | | |
| --- | --- | --- |
| gRNA name | gRNA recognition sequence | PAM sequence |
| Lox gRNA | 5'-GTATGCTATACGAAGTTATT-3' (SEQ ID NO: 1) | 5'-AGG-3' |
| mAi9 gRNA2 | 5'-AAGTAAAACCTCTACAAATG-3' (SEQ ID NO: 2) | 5'-TGG-3' |

Cas9SpC/SpT virus conjugation was carried out before cleavage assay. For this, 0.5 pmol of Cas9SpC was incubated with $1\times10^{10}$ vp SAd36.FFSpT (0.75 pmol viral SpT) or with $3.6\times10^9$ vp SAd36.HSpT (1.5 pmol viral SpT) at room temperature for 2 hours. Cas9, Cas9SpC, and virus-conjugated Cas9SpC and single gRNA were constituted in a volume of 29 μl by following a New England Biolabs' protocol: 1× NEBuffer r3.1, 0.5 pmol of Cas9, Cas9SpC, or Cas9SpC conjugated by FFSpT or by HSpT virus, and 0.5 pmol single gRNA at 25° C. for 10 minutes. Following addition of 50 fmol Rosa26-tdTomato DNA fragment, the reaction carried out 37° C. for 15 minutes, treated with 1 ul of 20 mg/ml proteinase K at room temperature for 10 minutes followed by fragment analysis on 2% agarose gels.

Example 2: A Novel Ad-mRNA Vaccine Platform

Significance

Described herein is a highly original program of bioengineering and technology development to capture the full promise of mRNA and adenoviral vectors to improve neoantigen cancer vaccines. Neoantigen cancer vaccines represent a unique personalized approach to cancer immunotherapy. One unique requirement of neoantigen vaccines is the ability to rapidly identify tumor antigens, and then seamlessly integrate these antigens into effective vaccine platforms. The mRNA vaccine platform provides clear advantages in terms of the ability to rapidly target genetic alterations present in patient tumors. However, mRNA vaccines are not as effective as adenovirus vaccines in inducing CD4/CD8 T cell responses. The novel Ad-mRNA vaccine platform described herein has been specifically designed for effective delivery of mRNA. The combination of the two vaccine platforms exploits the ability of mRNA for rapid neoantigen derivation and the effectiveness of adenovirus for antitumor T cell induction. On this basis, described herein is proof of concept data to develop and test an Ad-mRNA-based neoantigen cancer vaccine approach.

In summary, the ability of mRNA vaccines to rapidly target genetic alterations in viruses and cancers highlights the exceptional flexibility of the mRNA vaccine platform for emerging viruses and neoantigen cancer vaccines. Application in the cancer vaccine space requires the orchestration of both CD4 and CD8 T cells responses. This is an inherent weakness of the mRNA vaccine platform.

The design of the Ad-mRNA vaccine platform exploits the ability to engineer adenovirus. Two key components of the Ad-mRNA vaccine platform modular design are explored herein (1) The Ad-mRNA vaccine platform will be engineered to achieve optimal complexing of mRNA and adenovirus, using novel "molecular glue" technology, thereby leveraging the intrinsic properties of Ad to induce robust CD4/CD8 T cell responses. (2) The Ad-mRNA vaccine platform allows engineering to redirect the native tropism of Ad, allowing specific targeting of DCs. The Ad-mRNA vaccine platform will be further engineered to address this goal.

The proof of concept studies described herein will establish the basic feasibility of the Ad-mRNA approach, informing future strategies to further improve vaccine efficacy. These future studies are possible given the modular nature of the Ad-mRNA vaccine platform which can be expanded in the future.

Innovation

The Ad-mRNA vaccine platform is highly original. Facets of the approach are novel from several perspectives:

From a vector design perspective—the vaccine platform integrates non-viral and viral elements as a composite system. Such a non-viral/viral design is highly original within the vaccine and vector science spaces.

From the vaccine perspective—the novel vaccine platform exploits the recently developed SpyTag/SpyCatcher "molecular glue" system for effective complexing of mRNA to the Ad capsid. Although this system has been employed for design of vaccines centered on virus-like particles (VLP), the Ad-mRNA vaccine platform is the first to apply this promising technology for the modification of adenovirus.

From the mRNA vector perspective—As noted, mRNA lipid nanoparticles have limited ability to induce CD4/CD8 T cell responses, and have limited potential for targeting the key antigen presenting cells relevant to orchestrating effective antitumor immunization. The novel vaccine platform thus represents a paradigm shift in the design of vectors capable of gene delivery of mRNA to key target sites for maximized induction of antitumor immunity.

Approach

Introduction

The strategy leverages key feasibilities established herein. In this regard, Ad-polylysine-mRNA vaccines have been designed and created (see e.g., FIG. 24). Polylysine is a polycationic molecule allowing it to form soluble complexes with negatively charged molecules. Polylysine has been widely used for delivery of DNA/RNA molecules. In this strategy, Ad virus is biotinylated, and then streptavidin conjugated to polylysine is bound to the Ad virus, allowing mRNA to complex with the Ad virus. The proof of concept data is presented herein that the Ad-pL-mRNA vaccines can achieve high efficiency gene transfer in vitro and in vivo (see e.g., FIG. 25A-FIG. 25B). The complexing of mRNA to Ad viruses will be optimized using an innovative bioengineering approach that leverages novel "molecular glue" methods. In this approach, SpyTag or DogTag is incorporated into adenovirus capsid to protein IX or the hexon. In this configuration SpyTag/DogTag serves as an anchor for Spy-Catcher/DogCatcher fusion proteins with candidate mRNA-binding domains (see e.g., FIG. 26A-FIG. 26B).

This strategy allows the complexing of mRNA at specific sites on the Ad capsid. This is superior to complexing at nonspecific sites associated with biotinylation of Ad. Indeed, preliminary studies have shown that the molecular glue method allows the realization of Ad-mRNA vectors which embody the capacity for highly efficient gene transfer (see e.g., FIG. 27A-FIG. 27B). Thus, the design of the novel vector will be optimized by comparing the utility of the SpyTag/SpyCatcher system vs the DogTag/DogCatcher approach. A range of candidate mRNA-binding domains will also be considered. In addition, the utility of conventional linear mRNA species versus the newly evolved circular mRNA vectors (cirRNA) will be evaluated. Several variables will be evaluated to derive an optimized vector species for piggyback transport of mRNA. The novel vaccine vector will be evaluated in murine models of cancer immunotherapy.

Preliminary Studies (1) Ad-pL-mRNA vaccines: An approach based on "adenovirus-polylysine" (Ad-pL) to link plasmid DNA to adenovirus vectors was previously pioneered (see e.g., Curiel D T et al. *Hum Gene Ther.* 1992, 3(2):147-154). This approach is adapted herein to mRNA. The preliminary studies demonstrate that Ad-pL-mRNA can accomplish high efficiency gene transfer of the mRNA encoded genes in vitro and in vivo (see e.g., FIG. 25A-FIG. 25B). As noted above, the clear advantage of the Ad-pL-mRNA platform compared to recombinant adenovirus is the flexibility of targeting genetic alterations using the linked mRNA, making it uniquely suitable for applications in personalized medicine such as neoantigen vaccines.

Engineering the Ad-mRNA Vector Platform for Augmented Complexing of mRNA

Introduction

Ad-mRNA vaccine platforms will be designed, engineered, and tested with the goal of identifying the platform that achieves the most efficient delivery of mRNA. Design strategies will be utilized whereby mRNA is complexed and attached using linkers in a "piggyback" fashion to the adenovirus capsid. As noted above, an approach based on "adenovirus-polylysine" (Ad-pL) was previously used to accomplish this goal with plasmid DNA (see e.g., Curiel D T et al. *Hum Gene Ther.* 1992, 3(2):147-154 and Conry R M et al. *Cancer research* 1995, 55(7):1397-1400) and this has been successfully transitioned to Ad-pL-mRNA (see e.g., FIG. 24 and FIG. 25A-FIG. 25B).

These data support a planned evaluation of Ad-pL-mRNA and related strategies in the field of neoantigen cancer vaccines. Of note, the current approach for deriving Ad-pL-mRNA vaccines employs a direct chemical cross-linking method using biotin and streptavidin. The Ad virus is biotinylated in a nonspecific fashion allowing the attachment of streptavidin-polylysine fusions. In this strategy, polylysine serves as the nucleic acid-binding component. Although the Ad-pL-mRNA strategy appears to be able to a level of in vitro and in vivo gene transfer, biotinylation is potentially deleterious to retaining the full infectivity functions of the adenovirus component. Specifically, biotinylation can affect the fiber binding protein and thereby impair infectivity/native tropism.

It is hypothesized that it may be feasible to employ alternative mRNA linkers to improve the Ad-mRNA platform's delivery capacity. On this basis, methods will be explored allowing precise construction of the platform that allow capsid attachment of an optimized mRNA-binding domain without perturbation of its infectivity functions. To this end, methods to precisely modify specific adenovirus capsid proteins not critical to adenovirus infectivity have been developed (see e.g., Li J et al. *Genome Med.* 2021, 13(1):56; Dmitriev I P et al. *J Virol* 2002, 76(14):6893-6899; Le L P et al. *Mol Imaging.* 2004, 3(2):105-116; Wu H et al. *J Virol* 2005, 79(6):3382-3390; and Matthews Q L *Virol J.* 2008, 5:98). Such modifications can serve as "anchors" for mRNA linkers. Candidate mRNA binding domains will be attached to specific capsid loci (either hexon or protein IX). Of note, the utility of the SpyTag/SpyCatcher and DogTag/DogCatcher systems of "molecular glue" has recently been explored. In proof of concept studies, the ability to utilize the SpyTag/SpyCatcher system to achieve directed linkages to the adenovirus capsid has been validated. In these initial studies SpyTag has been engineered into the fiber knob, and it was demonstrated that these engineered SpyTag anchors can successfully bind to SpyCatcher-GFP fusion molecules (see e.g., FIG. 28).

These studies validate that the molecular glue methods may be utilized to attach functional linkers to specific sites on the adenovirus capsid. However, engineering the SpyTag anchor onto the fiber knob impacts Ad vector tropism. To preserve native tropism, SpyTag and DogTag anchors will be engineered into the hexon or protein IX proteins (see e.g., FIG. 28) as these will allow improved complexing of mRNA while retaining the native tropism of Ad.

It may be noted, however, that the Ad-pL-mRNA vaccine platform has already demonstrated a level of gene transfer and vaccine efficacy that justifies further study of this platform. Further, the current design of the Ad-pL vector species has been successfully employed in human clinical trials in Europe, underscoring its direct translation potential. Nonetheless, the availability of new methods for exquisitely specific macromolecular coupling provides a unique opportunity to realize an Ad-mRNA platform with improved function, and enhanced manufacture/upscale characteristics more amenable to regulatory approval.

Experimental Design

Rationale: It was established in FIG. 27A-FIG. 27B that Ad-mRNA vectors constituted via molecular glue methods can achieve high efficiency gene transfer. Herein will be investigated strategies to achieve optimized vector design by: (1) evaluating two candidate attachment sites in the Ad capsid; (2) evaluating the utility of the SpyTag/SpyCatcher vs DogTag/DogCatcher molecular glue systems; (3) evaluating candidate mRNA-binding domains with district physiologies; (4) evaluating RNA coding molecular of district structure. TABLE 1 provides on overview of the variables that will be considered towards achieving an Ad-mRNA with an optimized gene transfer capacity.

TABLE 1

| Strategies to optimize mRNA delivery via Ad-mRNA nanoparticle platform. | | | |
| --- | --- | --- | --- |
| Capsid locale | Conjugation strategy | mRNA binding protein | mRNA species |
| Protein IX Hexon | SpyTag/SpyCatcher DogTag/Dog/Catcher SnoopTag/ SnoopCatcher | Polylysine Protamine RALA | Linear mRNA Circular mRNA Self-replicating mRNA |

Figure 24:
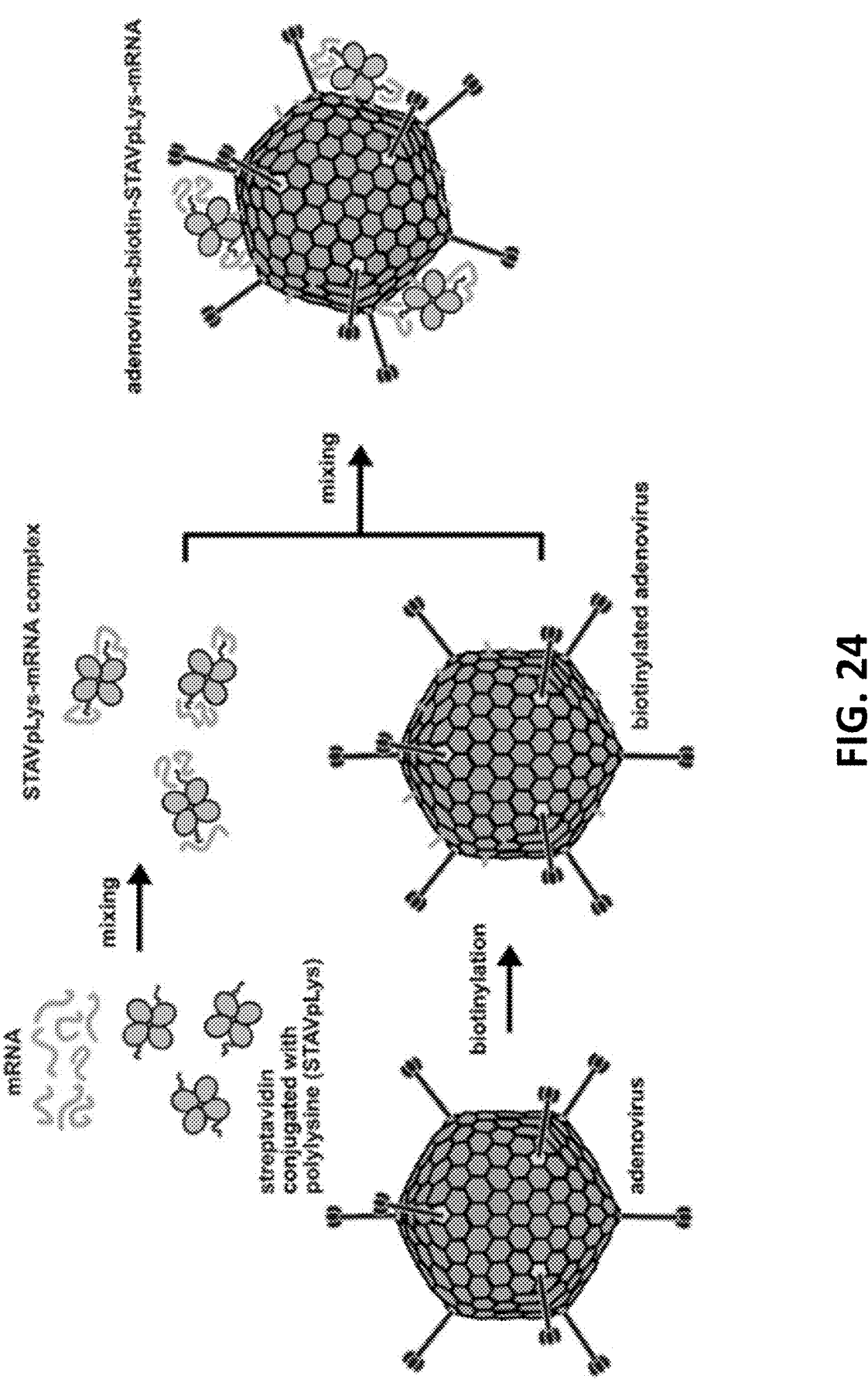
FIG. 24 is a schematic illustration of a novel Ad-mRNA vector (AdpL-mRNA) for mRNA delivery in accordance with the present disclosure. In this study, a straight-forward three step approach was employed to prepare AdpL-mRNA complexes. Anionic mRNA was first mixed with cationic streptavidin tagged polylysine to form complexes capable of binding with biotin. In parallel, the adenovirus was biotinylated via chemical labelling of accessible amine groups using the EZ-Link kit. Lastly, the complexed STAVpLys-mRNA was conjugated to the biotinylated virus via simple mixing. This strategy allows for rapid generation of a functional mRNA vector using a pre-prepared adenovirus.
Figures 26A, 26B:
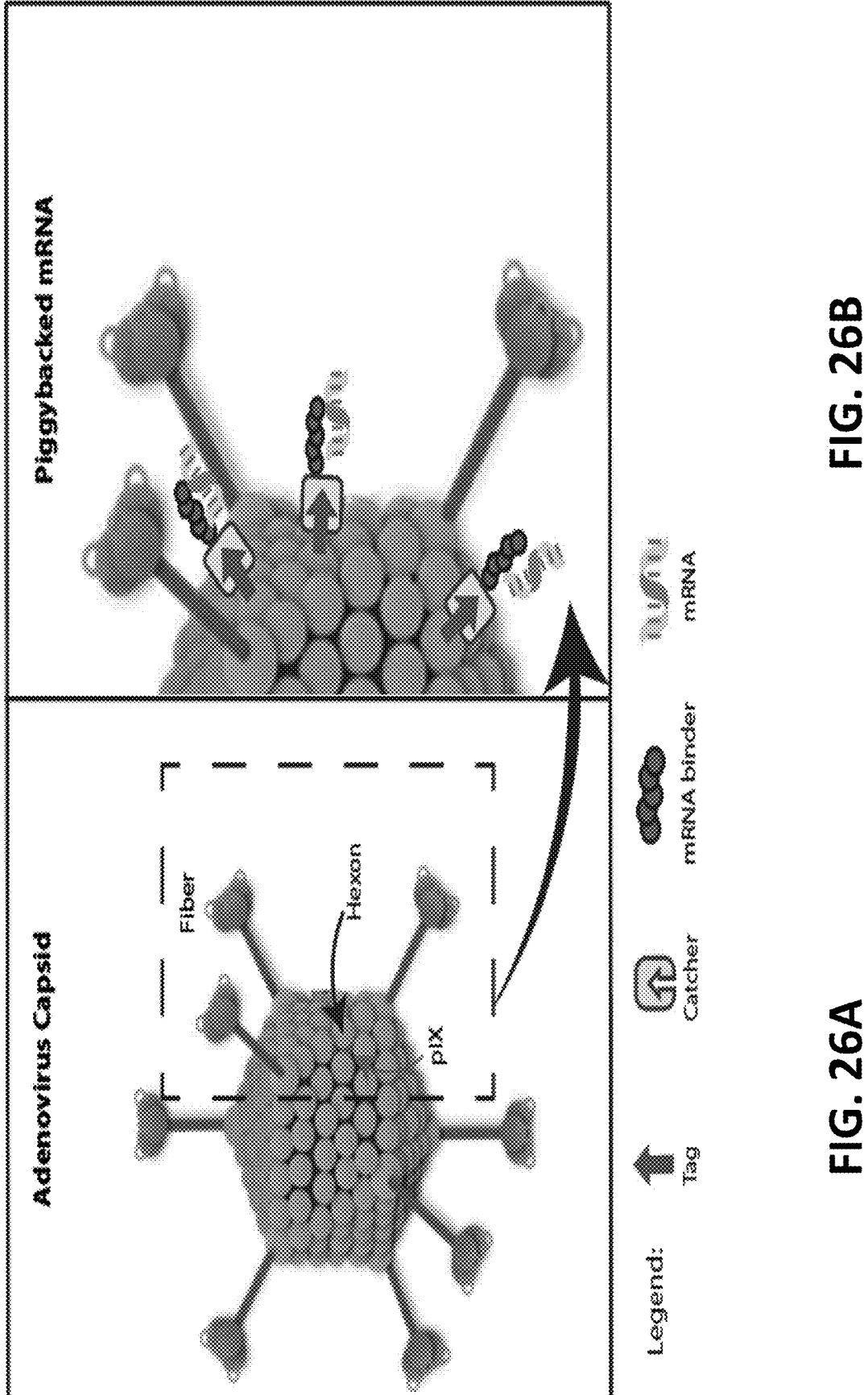
FIG. 26A-FIG. 26B include schematics showing adenovirus capsid with fiber and surface capsid proteins hexon and pIX (FIG. 26A) and mRNA piggyback onto adenovirus capsid via molecular glue (FIG. 26B) in accordance with the present disclosure. A Tag is engineered onto either capsid proteins hexon or pIX. mRNA is piggybacked onto adenovirus capsid via a catcher-linked mRNA binder.
Figures 27A, 27B:
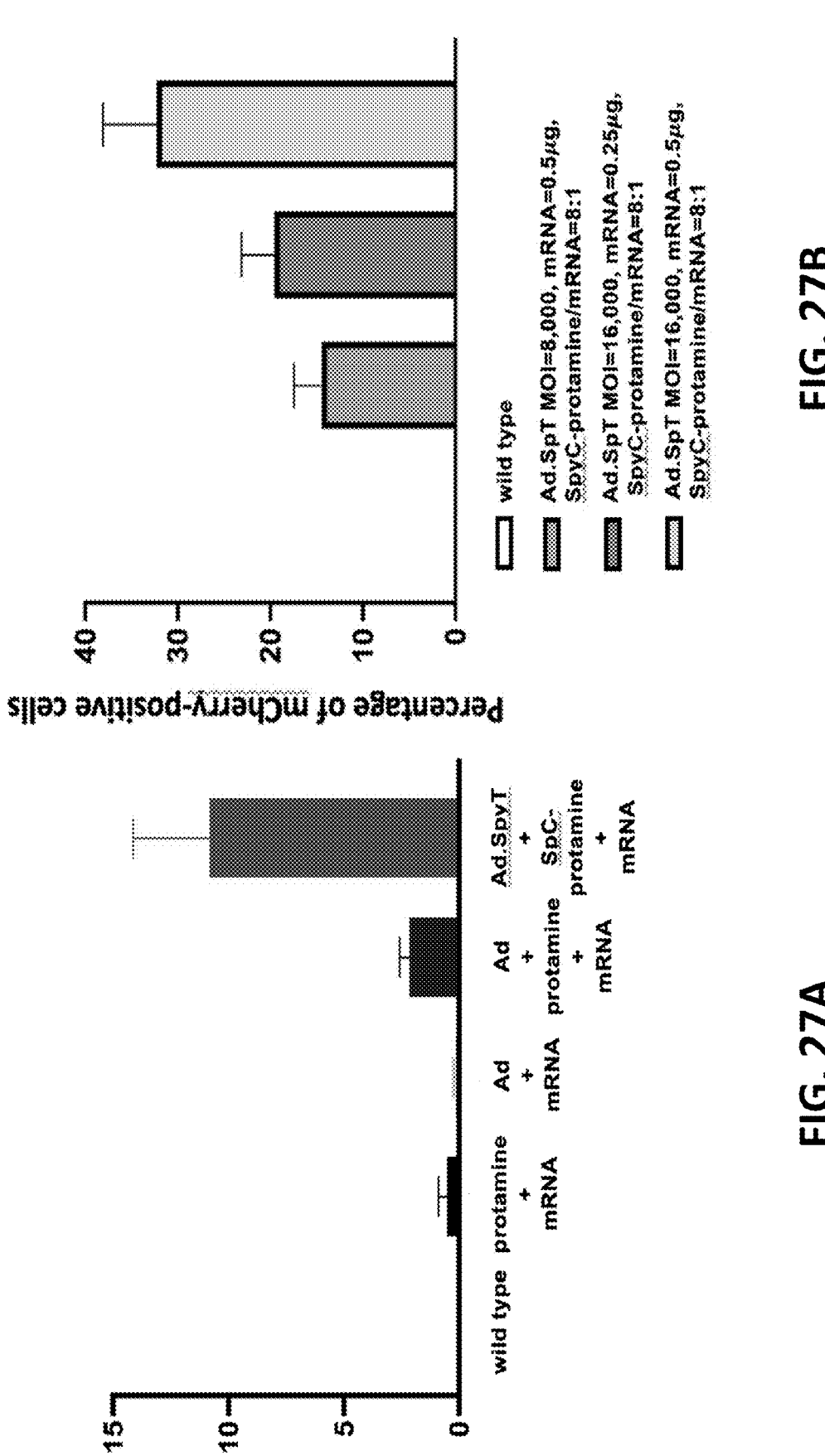
FIG. 27A-FIG. 27B is an exemplary embodiment showing engineered Ad with SpyTag incorporated into the hexon locales on the capsid protein serves as an anchoring platform for SpyCatcher-protamine-mRNA to attach in accordance with the present disclosure.
Figure 28:
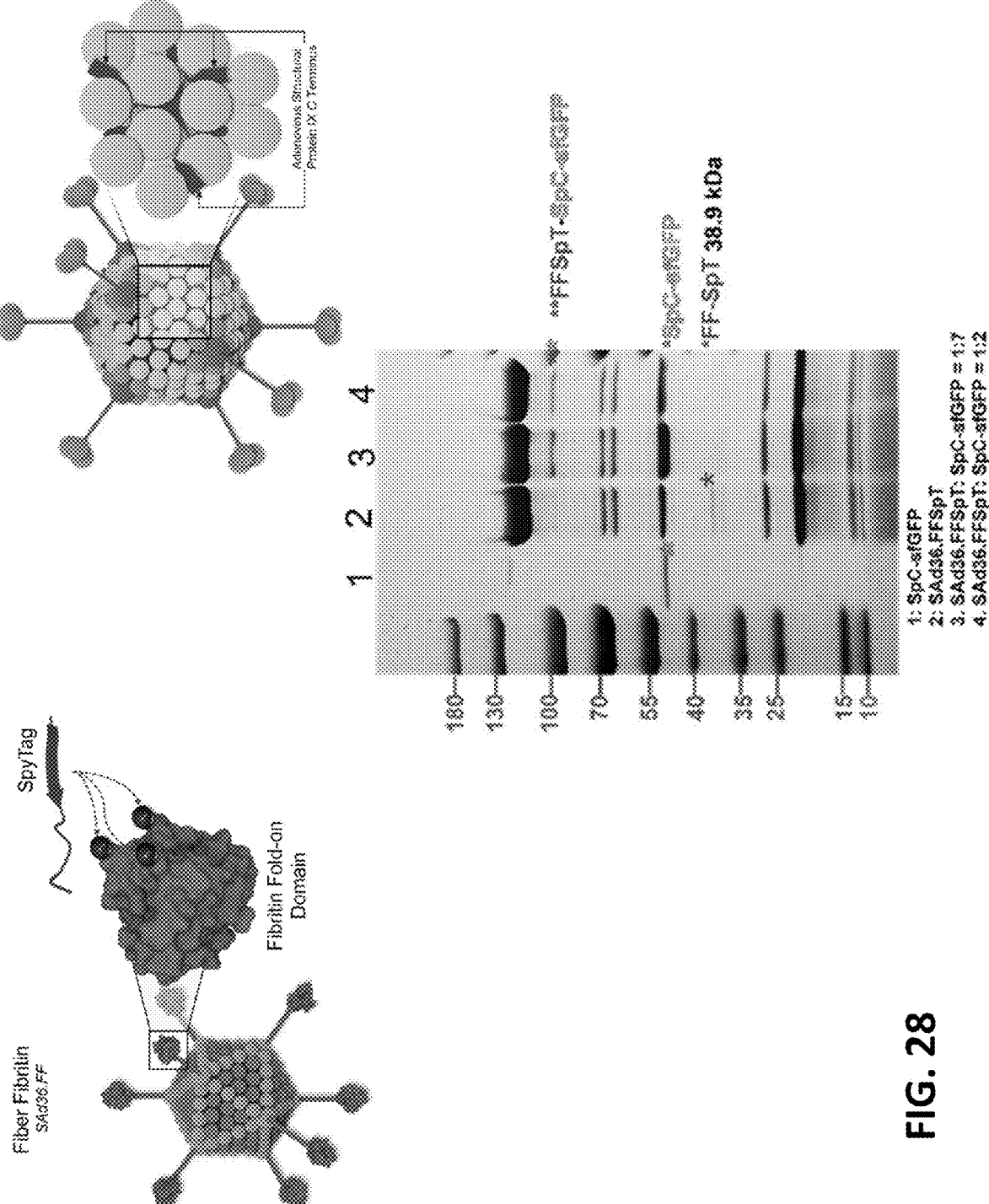
FIG. 28 is an exemplary embodiment showing SpyTag/SpyCatcher strategy for complexing mRNA to the adenovirus capsid in accordance with the present disclosure. Proof of concept studies of a fiber replacement method substitutes the terminus of adenovirus fiber protein with T4 fibritin (top left). This chimera is fused with SpyTag003 and incorporated into the capsid. The modified virus was conjugated with a SpyCatcher003-sGFP fusion. Successful integration of the SpyTag, and conjugation with the SpyCatcher003-sGFP fusion is documented by gel electrophoresis (bottom middle). Lane 1: 6.8 pmole of Spycatcher003-sfGFP; Lane 2: 4.9×10¹⁰ vp of SAd36.fiber-fibritin-SpyTag003; Lanes 3 and 4: 4.9×10¹⁰ vp of SAd36.fiber-fibritin-SpyTag003 was mixed with 1.24×10¹³ molecules (20.5 pmole; lane 3) or 4.1×10¹² molecules (6.8 pmole; lane 4) of Spycatcher003-sfGFP in PBS. The reaction was incubated for 2 hours at 37° C. before boiling in SDS-loading buffer and analysis by SDS-PAGE with Coomassie staining. Structure and organization of protein IX molecules in human Ad5 capsid are also shown (top right). The Ad5 capsid containing 240 protein IX molecules shown (red) relative to the icosahedral cage (yellow). The zoomed-in view of an icosahedral facet showing the coiled-coil helices structures depicting the protein IX C-Terminus (red) located between the interacting hexon trimer subunits (yellow circles).

OBJECTIVE 1: To construct adenovirus vectors containing molecular glue tags incorporated within adenoviral capsid proteins hexon or pIX. Methods have been established to insert SpyTag into an adenovirus protein in the fiber knob. Herein, a similar approach will be endeavored to insert SpyTag or DogTag at two adenoviral capsid loci best suited for attachment of an mRNA-binding domain—the pIX minor capsid protein and the hexon major capsid protein (see e.g., FIG. 26A-FIG. 26B). Whereas the modification of the fiber validated technical feasibility, the alternate capsid proteins offer advantages in terms of minimizing any negative impact on infectivity. Earlier work has established the methods to incorporate heterologous ligands at the COOH terminus of the pIX protein (see e.g., Dmitriev I P *J Virol.* 2002, 76(14):6893-6899). In addition, studies have been previously performed to define the optimal hexon structural loop in which to place heterologous peptide ligands (see e.g., Matthews Q L *PLoS One* 2010, 5(7): e11815). These methods will be used herein to modify an adenoviral vector genome base that is E1A/B-deleted for replication-incompetence and also encodes the RFP reporter. This reporter will allow differential tracking of the Ad vector component (encoding RFP) and the transported mRNA (neoantigens or GFP), as shown in FIG. 24 and FIG. 27A-FIG. 27B. Adenoviral vectors will be rescued and upscaled utilizing standard methods. Harvested viruses will be assayed for infectivity vs unmodified control Ad. In addition, Western blot analysis of the viruses will confirm the capsid incorporation and locale of the incorporated SpyTag. Probing with SpyCatcher-GFP or DogCatcher-GFP can accomplish this analysis, as shown in FIG. 28.

OBJECTIVE 2: To evaluate the accessibility of tag peptide incorporated into the viral capsid for binding of mRNA binding domain. Here the molecular glue-tagged Ad will be attached to the mRNA binding domains utilizing the "Catcher" fusion molecular coupling approach. Three candidate mRNA binding domains will be evaluated: poly-L-lysine (pL), protamine (PT), and RALA. These compounds have been shown to non-covalently associate with mRNA via electrostatic interactions. In addition, these agents have been shown to effectively condense mRNA within a compact toroid-type configuration. Furthermore, both of these agents have been used as vehicles to accomplish mRNA transduction of eukaryotic cells. For the RALA peptide, superior properties of endosome release have suggested its utility in nanoparticle design. To achieve this goal, fusions corresponding to SpyCatcher or DogCatcher in linkage to the mRNA-binding domains will be synthesized and purified. These endeavors will involve standard recombinant protein production/purification methods corresponding to published reports. Successful coupling of the fusions to the tagged Ad will be confirmed, as noted in FIG. 28.

Figures 25A, 25B:
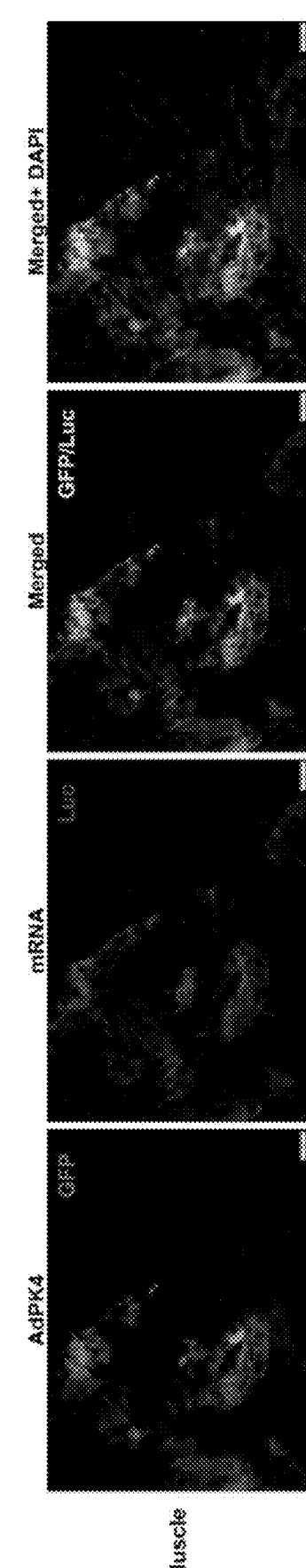
FIG. 25A-FIG. 25B is an exemplary embodiment showing in vitro gene transfer mediated by Ad-pL-mRNA in accordance with the present disclosure.

OBJECTIVE 3: To generate mRNA-loaded "piggyback" adenoviral vectors and evaluate their gene transfer capacity in vitro and in vivo. For construction of the control Ad-pL species (see e.g., FIG. 25A-FIG. 25B) biotin-labelled Ad, Streptavidin-pL and mRNA are combined. Ratios for optimization of gene delivery are determined empirically. For the gene transfer agents derived herein similar methods will be used—Tag-Ad plus fusions of SpyCatcher or DogCatcher and the various mRNA-binding domain and mRNA. The constituted complexes will be derived with either Luc or GFP reporters, for initial analysis of gene transfer. This analysis will include study of reporter encoding linear or circular RNA. In vitro studies will be endeavored as shown in FIG. 25A-FIG. 25B. In vivo gene transfer studies will be endeavored as shown in FIG. 25A-FIG. 25B and FIG. 27A-FIG. 27B. For vaccination studies discussed below, the optimal vector design defined herein will be employed for loading with tumor antigen encoding mRNA.

ALTERNATIVE APPROACHES: Central to the vector engineering endeavors is the ability to link an mRNA-binding domain to a specific adenovirus capsid site. In this regard, the utility of mRNA-binding domains of very distinct structure will be explored. In addition, molecular tags have been successfully engineered into the candidate capsid proteins targeted here for anchoring the mRNA-binding domains. Thus, key feasibilities have been established relevant to this step. However, alternative linkage methods fully consonant with the directed engineering goals have also been used. In this regard, an approach for molecular coupling based upon leucine zippers has previously been exploited (see e.g., Glasgow J N *PLoS One.* 2009, 4(12): e8355). In addition, a method utilizing camelid antibodies (sdAb) to cross-link molecules to the adenovirus capsid in a targeted manner has also been previously described (see e.g., Hangalapura B N *Cancer research* 2011, 71(17):5827-5837).

Testing the Derived Ad-mRNA Nanoparticle Vaccine Platform in Murine Models of Neoantigen Cancer Immunotherapy.

Introduction

Herein will be determined if vaccination with the novel Ad-mRNA vaccines can enhance anti-tumor vaccine potency in murine models. These studies build on previous work to identify cancer neoantigens in patients and murine tumors, and perform analysis of neoantigen-specific immune responses. Several Ad-mRNA vaccine constructs are already available, and permit this work performed alongside the optimization studies described herein. The use of E0771 breast cancer and pancreas adenocarcinoma, KP2-OxParp clone E (referred to as "Clone E") models, both syngeneic to C57BL/6 mice, is proposed. Neoantigens in these murine tumors have previously been identified. Vaccination of mice against neoantigens using either synthetic long peptides (SLPs) of 20-25 amino acids or comparable neoantigen encoding poly-epitope plasmid DNA elicits neoantigen specific T cell responses that offers modest, but statistically significant reduced tumor growth.

Experimental Design

A tiered process for determination of in vivo efficacy of Ad-mRNA constructs is proposed. All constructs will be tested for induction of neoantigen-specific T cell responses, and the most promising will be selected for assessment of their ability to elicit tumor protection. The experimental schema and process is outlined in FIG. 29.

OBJECTIVE 1: To assess immunogenicity of Ad-mRNA vectors expressing cancer neoantigens.

Ad-mRNA constructs will encode either three E0771 neoantigen epitopes (each 60-75 nucleotides) or six neoantigens from Clone E. Mice will be vaccinated two times one week apart, with functional read-outs starting one week later. Specifically, splenocytes will be tested for their ability to produce interferon-gamma (IFNγ) after stimulation with individual neoantigen peptide in an IFNγ ELISpot assay (see e.g., FIG. 29). As positive control, ovalbumin (OVA) mRNA complexed to Ad will be used with testing of splenocytes against the immunodominant MHC I and II OVA epitopes. Negative controls include Ad without mRNA and mRNA without Ad. Neoantigen-specific T cell responses will also be assessed through intracellular cytokine analysis after in vitro stimulation of splenocytes with neoantigen encoding peptides. Flow cytometry analysis will include analysis of IL-2, IFNγ, and the cytotoxicity marker, CD107a/b in both CD4 and CD8 T cells. Since a noted benefit of the adenovirus is its ability to elicit long-lasting immunity, memory responses will be assessed ~35 days after the first vaccination for those constructs that elicit a robust primary immune response. Neoantigen-specific cytotoxicity will be assessed in vivo by injecting mice with a 50-50 mix of neoantigen-pulsed, CSFE$^{hi}$-labeled cells and unpulsed CFSE$^{lo}$ cells. After 24 hrs, the proportions of CFSE$^{hi}$ vs CFSE$^{lo}$ will be determined by flow cytometry using isolated splenocytes. Any Ad-mRNA construct that elicits primary and memory neoantigen-specific immune responses above the negative controls will be selected for further studies.

Figure 29:
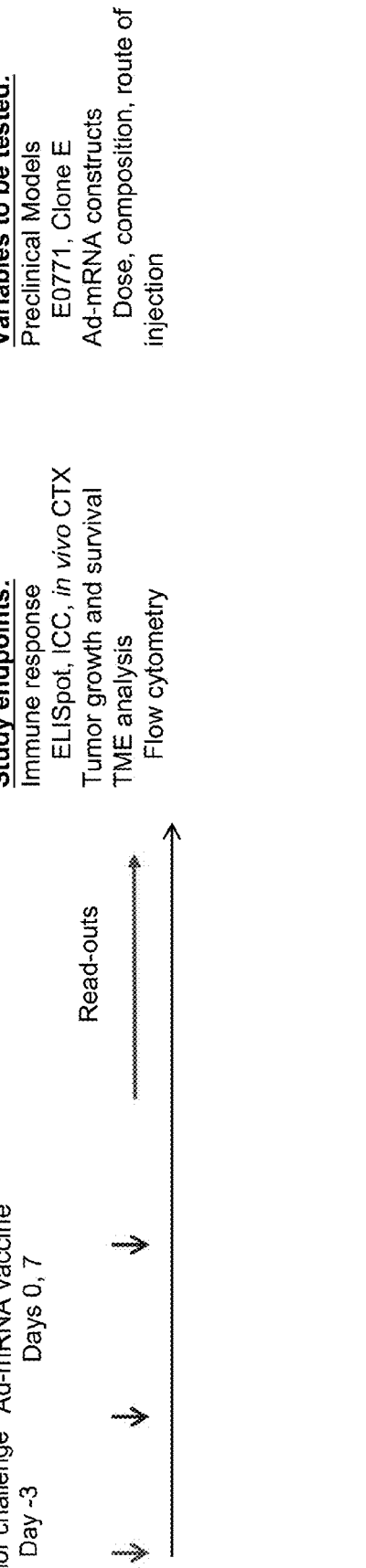
FIG. 29 is a schematic of a representative experiment in accordance with the present disclosure. Groups of mice will be vaccinated with an individual Ad-mRNA construct. Based on analysis of an immune response, constructs eliciting an immune response will be tested further for tumor protection. E0771 or Clone E tumors will be established subcutaneously prior to vaccination, and tumor growth and survival will be determined. ICC=intracellular cytokine analysis CTX=cytotoxicity.

OBJECTIVE 2: To determine the impact of Ad-mRNA vaccination on tumor growth and survival. In this objective, whether induction of primary and memory immunity translates into better tumor protection and survival will be tested. Vaccination will be performed after subcutaneous tumor inoculation, as indicated in FIG. 29. Growth of tumors will be tracked through caliper measurements every 3 days. Ad-mRNA constructs that significantly reduce tumor growth will be further tested for their ability to prolong survival. In case complete tumor regression is observed, mice will be re-challenged with a similar tumor inoculate on the opposite flank to confirm tumor-specific immunity is induced. For those Ad-mRNA constructs that elicit significant tumor protection, the immune subset composition in tumors will be determined at three time points after vaccination, when tumors are small (0.3-0.4 cm in one diameter), intermediate size (0.7-1.0 cm) or large (>1.3 cm). Single cell suspensions of tumors will be subjected to multi-parameter flow cytometry using markers for both immune cell subsets (e.g., CD45, CD3, CD4, CD8, CD27, FoxP3, CD11b, CD11c, F4/80, Ly6C, Ly6G) as well as functional markers (MHC II, granzyme B, CD25, PD-1, TIGIT, LAG3, CD44, and CD69, as previously described.

ALTERNATIVE APPROACHES: The preliminary data as well as reports in the literature suggest that mRNA vaccine delivered through an Ad is a potent strategy for effective immunization. It is anticipated that the rationalized optimization studies discussed above will provide a number of promising candidates to test in vivo. Nonetheless, analysis of the tumor microenvironment (TME) may provide further insight into any pathways that may restrain T cell responses in the TME. Vaccine therapy may be combined with strategies targeting immunosuppressive myeloid cells and/or immune checkpoints as desired.

What is claimed is:

1. A conjugate system comprising:
   (i) an adenovirus comprising an exterior surface, wherein the exterior surface comprises a hexon protein surface and a fiber knob surface; and
   (ii) at least one polypeptide comprising a first domain and a second domain, wherein the first domain comprises a binding partner and the second domain comprises a Cas protein; and
   wherein the hexon protein surface and/or the fiber knob surface comprises a peptide tag capable of binding to the binding partner.

2. The conjugate system of claim 1, wherein the peptide tag is a SpyTag and the binding partner is a SpyCatcher.

3. The conjugate system of claim 1, wherein the at least one polypeptide further comprises at least one nuclear localization signal (NLS), affinity tag, or flexible peptide linker.

4. The conjugate system of claim 1, wherein the binding partner and the peptide tag are covalently bound.

5. The conjugate system of claim 1, wherein the adenovirus is a simian adenovirus.

6. The conjugate system of claim 5, wherein the adenovirus is simian adenovirus species E serotype 36 (Sad36).

7. The conjugate system of claim 1, wherein the fiber knob surface comprises a fibritin T4 fold-on domain.

8. The conjugate system of claim 1, wherein the peptide tag is associated with a hypervariable region of the hexon protein surface.

9. The conjugate system of claim 1, wherein the peptide tag is fused to a flexible linker.

10. The conjugate system of claim 1, wherein the adenovirus comprises at least about 30 fiber knob surfaces comprising the peptide tag.

11. The conjugate system of claim 1, wherein the adenovirus comprises at least about 300 hexon protein surfaces comprising the peptide tag.

12. The conjugate system of claim 1, further comprising a guide RNA (gRNA).

13. The conjugate system of claim 1, wherein the at least one polypeptide or the peptide tag further comprises a protease-cleavable linker or a biodegradable linker.

14. The conjugate system of claim 13, wherein the protease-cleavable linker comprises an adenovirus L3 protease (AVP) preferential cleavage site.

15. The conjugate system of claim 1, wherein the adenovirus does not comprise viral DNA.

16. The conjugate system of claim 1, further comprising targeting peptides or targeting adapters.

17. A method of genetically engineering a cell, the method comprising delivering the conjugate system of claim 1 to the cell.

18. A conjugate system comprising:
   (i) an adenovirus comprising an exterior surface comprising a hexon protein surface and a protein IX surfacer, and
   (ii) at least one polypeptide comprising a first domain and a second domain, wherein the first domain comprises a binding partner and the second domain comprises an mRNA-binding domain; and
   wherein the hexon protein surface and/or the protein IX surface comprises a peptide tag capable of binding to the binding partner.

19. The conjugate system of claim 18, wherein
   the peptide tag is a SpyTag and the binding partner is a SpyCatcher;
   the peptide tag is a DogTag and the binding partner is a DogCatcher; or
   the peptide tag is a SnoopTag and the binding partner is a SnoopCatcher.

20. The conjugate system of claim 18, further comprising an mRNA.

21. The conjugate system of claim 20, wherein the mRNA is a linear mRNA, a circular mRNA, or a self-replicating mRNA.

22. The conjugate system of claim 20, wherein the mRNA-binding domain comprises polylysine, protamine, or RALA.

23. The conjugate system of claim 20, wherein the mRNA encodes a cancer neoantigen.

24. A method of treating cancer in a subject in need thereof, the method comprising administering to the subject the conjugate system of claim 23.

25. A method of providing gene therapy to a subject in need thereof, the method comprising administering to the subject the conjugate system of claim 18.

* * * * *

```
                         SEQUENCE LISTING

Sequence total quantity: 10
SEQ ID NO: 1             moltype = DNA  length = 20
FEATURE                  Location/Qualifiers
source                   1..20
                         mol_type = other DNA
                         organism = synthetic construct
SEQUENCE: 1
gtatgctata cgaagttatt                                         20

SEQ ID NO: 2             moltype = DNA  length = 20
FEATURE                  Location/Qualifiers
source                   1..20
                         mol_type = other DNA
                         organism = synthetic construct
SEQUENCE: 2
aagtaaaacc tctacaaatg                                         20

SEQ ID NO: 3             moltype = DNA  length = 20
FEATURE                  Location/Qualifiers
source                   1..20
                         mol_type = other DNA
                         organism = synthetic construct
SEQUENCE: 3
ggccacgagt tcgagatcga                                         20

SEQ ID NO: 4             moltype = DNA  length = 20
FEATURE                  Location/Qualifiers
source                   1..20
                         mol_type = other DNA
                         organism = synthetic construct
SEQUENCE: 4
cactcttgag ggccacaaag                                         20

SEQ ID NO: 5             moltype = DNA  length = 20
FEATURE                  Location/Qualifiers
source                   1..20
                         mol_type = other DNA
                         organism = synthetic construct
SEQUENCE: 5
gcaacgtgct ggttattgtg                                         20

SEQ ID NO: 6             moltype = DNA  length = 20
FEATURE                  Location/Qualifiers
source                   1..20
                         mol_type = other DNA
                         organism = synthetic construct
SEQUENCE: 6
ctcaccatgg tggcgggatc                                         20

SEQ ID NO: 7             moltype = DNA  length = 24
FEATURE                  Location/Qualifiers
source                   1..24
                         mol_type = other DNA
                         organism = synthetic construct
SEQUENCE: 7
gccggcccca aggaagactg ggag                                    24

SEQ ID NO: 8             moltype = DNA  length = 19
FEATURE                  Location/Qualifiers
source                   1..19
                         mol_type = other DNA
                         organism = synthetic construct
SEQUENCE: 8
gcacagacgt ccatcagcc                                          19

SEQ ID NO: 9             moltype = DNA  length = 23
FEATURE                  Location/Qualifiers
source                   1..23
                         mol_type = other DNA
                         organism = synthetic construct
SEQUENCE: 9
```

-continued

```
ggttcggctt ctggcgtgtg acc                                              23

SEQ ID NO: 10          moltype = DNA   length = 20
FEATURE                Location/Qualifiers
source                 1..20
                       mol_type = other DNA
                       organism = synthetic construct
SEQUENCE: 10
ctcgcccttg ctcaccatgg                                                  20
```